(12) United States Patent
Sheehan et al.

(10) Patent No.: US 9,073,912 B2
(45) Date of Patent: Jul. 7, 2015

(54) AZETIDINE DERIVATIVES AS ANTIPARASITIC AGENTS

(71) Applicant: Zoetis LLC, Florham Park, NJ (US)

(72) Inventors: Susan M. K. Sheehan, Kalamazoo, MI (US); Valerie A. Vaillancourt, Kalamazoo, MI (US)

(73) Assignee: Zoetis Services LLC, Florham Park, NJ (US)

( * ) Notice: Subject to any disclaimer, the term of this patent is extended or adjusted under 35 U.S.C. 154(b) by 0 days.

(21) Appl. No.: 14/399,084

(22) PCT Filed: May 6, 2013

(86) PCT No.: PCT/US2013/039638
§ 371 (c)(1),
(2) Date: Nov. 5, 2014

(87) PCT Pub. No.: WO2013/169622
PCT Pub. Date: Nov. 14, 2013

(65) Prior Publication Data
US 2015/0119377 A1    Apr. 30, 2015

Related U.S. Application Data

(60) Provisional application No. 61/644,512, filed on May 9, 2012.

(51) Int. Cl.
| | | |
|---|---|---|
| C07D 401/14 | (2006.01) | |
| C07D 403/10 | (2006.01) | |
| C07D 413/14 | (2006.01) | |
| C07D 413/10 | (2006.01) | |
| A61K 31/4025 | (2006.01) | |
| A61K 31/422 | (2006.01) | |
| A61K 31/4155 | (2006.01) | |
| A61K 31/4439 | (2006.01) | |
| A61K 31/444 | (2006.01) | |
| C07D 409/14 | (2006.01) | |
| A61K 45/06 | (2006.01) | |
| A01N 43/44 | (2006.01) | |
| A01N 43/82 | (2006.01) | |
| A01N 43/56 | (2006.01) | |
| A01N 43/76 | (2006.01) | |

(52) U.S. Cl.
CPC ............ *C07D 413/14* (2013.01); *C07D 403/10* (2013.01); *A61K 31/4025* (2013.01); *A61K 45/06* (2013.01); *A01N 43/44* (2013.01); *C07D 413/10* (2013.01); *A61K 31/422* (2013.01); *A01N 43/82* (2013.01); *A61K 31/4155* (2013.01); *A01N 43/56* (2013.01); *C07D 401/14* (2013.01); *A61K 31/4439* (2013.01); *A01N 43/76* (2013.01); *C07D 409/14* (2013.01); *A61K 31/444* (2013.01)

(58) Field of Classification Search
None
See application file for complete search history.

(56) References Cited

U.S. PATENT DOCUMENTS

2014/0213572 A1*   7/2014   Allen et al. .............. 514/210.18

FOREIGN PATENT DOCUMENTS

| JP | 2012-031148 | 2/2012 |
|---|---|---|
| WO | 2007/075459 | 7/2007 |
| WO | 2011/101229 | 8/2011 |
| WO | 2012/017359 | 2/2012 |
| WO | 2012/035011 | 3/2012 |

OTHER PUBLICATIONS

PCT International Search Report, PCT/US2013/039638, mailed Oct. 24, 2013 (5 pages).

* cited by examiner

*Primary Examiner* — Michael Barker
(74) *Attorney, Agent, or Firm* — Paul M. Misiak

(57) ABSTRACT

This invention recites substituted azetidine derivatives of Formula (1) stereoisomers thereof, veterinarily acceptable salts thereof, compositions thereof, and their use as a parasiticide in animals. The substituents A, B, $R^{1a}$, $R^{1b}$, $R^{1c}$, $R^2$, $R^3$, $R^4$, $R^6$, and n are as described herein.

(1)

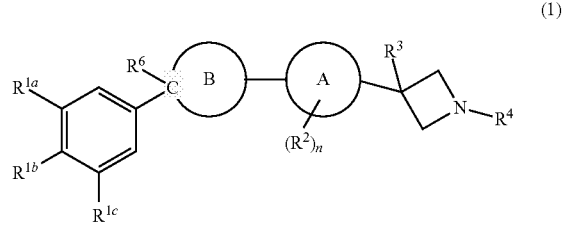

15 Claims, No Drawings

AZETIDINE DERIVATIVES AS ANTIPARASITIC AGENTS

FIELD OF THE INVENTION

This invention relates to azetidine derivatives having parasiticidal activity. The compounds of interest are heterocyclic derivatives substituted with phenylazetidines, naphthyl-azetidines, or heteroaryl azetidines. The invention also relates to compositions and methods of use thereof.

BACKGROUND

There is a need for improved antiparasitic agents for use with animals, and in particular there is a need for improved long-acting (i.e., 6-months) insecticides and acaricides. Furthermore there is a need for improved topical and oral products with convenient administration and which contain one or more of such antiparasitic agents which can be used to effectively treat ectoparasites, such as insects (e.g., fleas, lice, and flies) acarids (e.g., mites and ticks), and copepods (e.g., sea lice). The compounds of the present invention can also be used as an endoparasiticide to effectively treat helminthes, for example, cestodes (tapeworms), nematodes (roundworms), and trematodes (flukes). Such products would be particularly useful for the treatment of animals (e.g., cat, dog, horse, cattle, swine, sheep, goats, birds, and fish).

The compounds currently available for insecticidal, acaricidal, and helminth treatment of companion animals and livestock do not always demonstrate good activity, good speed of action, or a long duration of action. Most treatments contain hazardous chemicals that can have serious consequences, including lethality from accidental ingestion. Persons applying these agents are generally advised to limit their exposure. Pet collars and tags have been utilized to overcome some problems, but these are susceptible to chewing, ingestion, and subsequent toxicological affects to the animal. Thus, current treatments achieve varying degrees of success which depend partly on toxicity, method of administration, and efficacy. Currently, some agents are actually becoming ineffective due to parasitic resistance.

Diphenyl-3,4-dihydro-2H-pyrrole derivatives and 1,3-diphenylpyrrolidine derivatives have been disclosed in the art as having insecticidal and acaricidal activity. For example, JP2012031148 and WO2012/035011. Further, WO2007/075459 discloses phenyl isoxazolines substituted with 5- to 6-membered heterocycles. WO2011/101229 discloses certain dihydrofuran derivatives as antiparasitic agents. Certain isoxazoline-azetidine derivatives were disclosed in WO2012/017359. However, the citations do not describe the non-isoxazole azetidine derivatives of the instant invention, nor does the prior art indicate that such compounds would be useful against a spectrum of parasitic species, regardless of morphological lifecycle stages, in animals.

Despite the availability of effective, broad spectrum antiparasitic agents, there remains a need for a safer, convenient, efficacious, and environmentally friendly product that will overcome the ever-present threat of resistance development.

The present invention overcomes one or more of the various disadvantages of, or improves upon, the properties of existing compounds. In particular the present invention develops new azetidine derivatives which demonstrate such properties.

SUMMARY

The present invention provides Formula (1) compounds, stereoisomers thereof, pharmaceutical or veterinarily acceptable salts thereof, which act as long-acting (i.e., 6 months) parasiticides, in particular, ectoparasiticides; therefore may be used to treat acarines and insect infection and infestation in animals. In addition, the invention contemplates the control and prevention endoparasites in animals. The present invention also contemplates the control and treatment of tick borne diseases, for example, Lyme disease, canine and bovine anaplasmosis, canine ehrlichiosis, canine rickettsiosis, canine and bovine babesiosis, epizootic bovine abortion, and theileriosis, as well as leishmaniasis, demodicosis and sarcoptic mange resulting from biting flies and mites. Thus, according to the invention, there is provided a compound of Formula (1)

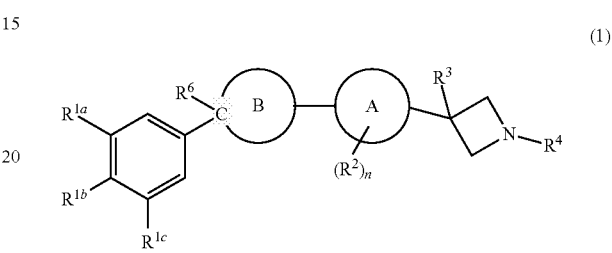

(1)

wherein
A is phenyl, naphthyl, or heteroaryl where said heteroaryl contains 1 to 4 heteroatoms each independently selected from N, O and S;
B is

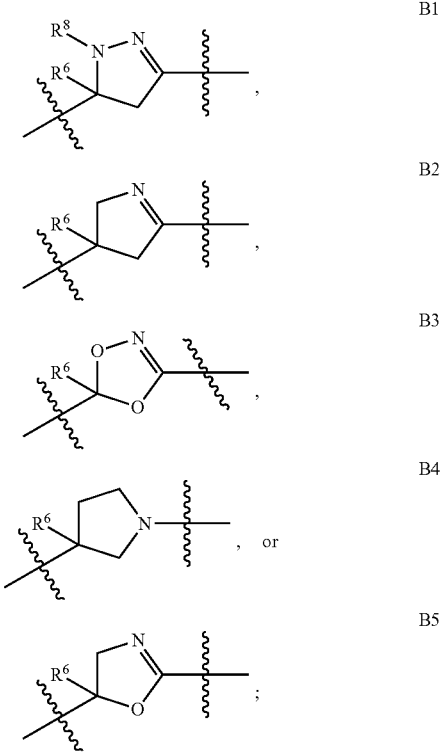

wherein "~~~" represents the point of attachment;
$R^{1a}$, $R^{1b}$, and $R^{1c}$ are each independently hydrogen, halo, hydroxyl, cyano, nitro, $C_1$-$C_6$alkyl, $C_1$-$C_6$haloalkyl, $C_1$-$C_6$alkoxy, $C_0$-$C_3$alkyl$C_3$-$C_6$cycloalkyl, $C_1$-$C_6$haloalkoxy, —C(O)NH$_2$, —SF$_5$, or —S(O)$_p$R;

$R^2$ is halo, cyano, $C_1$-$C_6$alkyl, $C_1$-$C_6$haloalkyl, nitro, hydroxyl, —C(O)NR$^a$R$^b$, $C_2$-$C_6$alkenyl, $C_2$-$C_6$alkynyl, —S(O)$_p$R, or —OR;

$R^3$ is hydrogen, halo, hydroxyl, cyano, $C_1$-$C_6$alkyl, $C_1$-$C_6$haloalkyl, $C_0$-$C_3$alkylC$_3$-C$_6$cycloalkyl, —C(O)NH$_2$, nitro, —SC(O)R, —C(O)NR$^a$R$^b$, $C_0$-$C_3$alkylNR$^a$R$^4$, —NR$^a$NR$^b$R$^4$, —NR$^a$OR$^b$, —ONR$^a$R$^b$, N$_3$, —NHR$^4$, —OR, or —S(O)$_p$R;

$R^4$ is hydrogen, $C_1$-$C_6$alkyl, $C_0$-$C_6$alkylC$_3$-$C_6$cycloalkyl, —C(O)R$^5$, —C(S)R$^5$, —C(O)NR$^a$R$^5$, —C(O)C(O)NR$^a$R$^5$, —S(O)$_p$R$^c$, —S(O)$_2$NR$^a$R$^5$, —C(NR$^7$)R$^5$, —C(NR$^7$)NR$^a$R$^5$, $C_0$-$C_6$alkylphenyl, $C_0$-$C_6$alkylheteroaryl, or $C_0$-$C_6$alkylheterocycle;

$R^5$ is hydrogen, $C_1$-$C_6$alkyl, $C_2$-$C_6$alkenyl, $C_0$-$C_6$alkylC$_3$-$C_6$cycloalkyl, $C_0$-$C_6$alkylphenyl, $C_0$-$C_6$alkylheteroaryl, or $C_0$-$C_6$alkylheterocycle;

$R^6$ is cyano, $C_1$-$C_6$alkyl, $C_1$-$C_6$haloalkyl, —C(O)NR$^a$R$^b$, $C_2$-$C_6$alkenyl, $C_2$-$C_6$alkynyl, $C_2$-$C_6$haloalkenyl, or $C_2$-$C_6$haloalkynyl;

$R^7$ is hydrogen, $C_1$-$C_6$alkyl, hydroxyl, cyano, nitro, —S(O)$_p$R$^c$, or $C_1$-$C_6$alkoxy;

$R^8$ is hydrogen, $C_1$-$C_6$alkyl, hydroxyl, cyano, —S(O)$_p$R$^c$, or $C_1$-$C_6$alkoxy;

R is $C_1$-$C_6$alkyl or $C_3$-$C_6$cycloalkyl each optionally substituted by at least one halo;

$R^a$ is hydrogen, $C_1$-$C_6$alkyl, or $C_0$-$C_3$alkylC$_3$-$C_6$cycloalkyl; wherein the alkyl and alkylcycloalkyl is optionally substituted by cyano or at least one halo substituent;

$R^b$ is hydrogen, $C_1$-$C_6$alkyl, $C_3$-$C_6$cycloalkyl, $C_0$-$C_3$alkylphenyl, $C_0$-$C_3$alkylheteroaryl, or $C_0$-$C_3$alkylheterocycle, each optionally substituted, where chemically possible, with at least one substituent selected from hydroxyl, cyano, halo, or —S(O)$_p$R;

$R^c$ is $C_1$-$C_6$alkyl, $C_1$-$C_6$haloalkyl, $C_1$-$C_6$haloalkylC$_3$-$C_6$cycloalkyl, $C_0$-$C_3$alkylC$_3$-$C_6$cycloalkyl, $C_0$-$C_3$alkylphenyl, $C_0$-$C_3$alkylheteroaryl, or $C_0$-$C_3$alkylheterocycle each optionally substituted with at least one substituent selected from cyano, halo, hydroxyl, oxo, $C_1$-$C_6$alkyl, $C_1$-$C_6$alkoxy, $C_1$-$C_6$haloalkoxy, $C_1$-$C_6$haloalkyl, —S(O)$_p$R, —SH, —S(O)$_p$NR$^a$R$^b$, —NR$^a$R$^b$, —NR$^a$C(O)R$^b$, —SC(O)R$^b$, —SCN, or —C(O)NR$^a$R$^b$;

each of $R^4$ and $R^5$ $C_1$-$C_6$alkyl or $C_0$-$C_6$alkylC$_3$-$C_6$cycloalkyl can be optionally and independently substituted by at least one substituent selected from $C_1$-$C_6$alkyl, cyano, halo, hydroxyl, $C_1$-$C_6$hydroxyalkyl, oxo, $C_1$-$C_6$alkoxy, $C_1$-$C_6$haloalkoxy, $C_1$-$C_6$alkyl, $C_1$-$C_6$haloalkyl, —S(O)$_p$R$^c$, —SH, —S(O)$_p$NR$^a$R$^b$, —NR$^a$R$^b$, —NR$^a$C(O)R$^b$, —SC(O)R$^c$, —SCN, or —C(O)NR$^a$R$^b$; and wherein $R^4$ and $R^5$ $C_0$-$C_6$alkylphenyl, $C_0$-$C_6$alkylheteroaryl, or $C_0$-$C_6$alkylheterocycle moiety can be further optionally substituted with at least one substituent selected from $C_1$-$C_6$alkyl, cyano, halo, oxo, =S, =NR$^7$, hydroxyl, $C_1$-$C_6$hydroxyalkyl, $C_1$-$C_6$alkoxy, $C_1$-$C_6$alkyl, $C_1$-$C_6$haloalkyl, —SH, —S(O)$_p$R, and $C_1$-$C_6$haloalkoxy;

n is the integer 0, 1, or 2, and when n is 2, each $R^2$ may be identical or different from each other; and p is the integer 0, 1, or 2, stereoisomers thereof, and pharmaceutically or veterinarily acceptable salts thereof.

In another aspect of the invention, A is phenyl, naphthyl, pyridinyl, pyrimidinyl, pyrazolyl, imidazolyl pyrrolyl, furanyl, thiophenyl, triazolyl, tetrazolyl, thiazolyl, isoxazolyl, oxazolyl, oxadiazolyl, thiadiazolyl, pyridazinyl, pyrazinyl, benzofuranyl, benzothiophenyl, indolyl, benzimidazolyl, indazolyl, benzotriazolyl, thieno[2,3-c]pyridine, thieno[3,2-b]pyridine, and benzo[1,2,5]thiadiazole. In another aspect of the invention, A is phenyl, naphthyl, pyridinyl, pyrimidinyl, pyrazolyl, triazolyl, tetrazolyl, thiazolyl, isoxazolyl, benzofuranyl, benzothiophenyl, indolyl, and benzo[1,2,5]thiadiazole. In another aspect of the invention, A is phenyl, naphthyl, pyridinyl, pyrazolyl, triazolyl, isoxazolyl, benzofuranyl, and benzo[1,2,5]thiadiazole. In another aspect of the invention, A is phenyl, naphthyl, pyridinyl, pyrazolyl, and benzo[1,2,5]thiadiazole. In another aspect of the invention, A is phenyl, pyridinyl, naphthyl, or benzo[1,2,5]-thiadiazole. In another aspect of the invention A is phenyl, naphthyl, or pyridinyl. In another aspect of the invention A is phenyl. In another aspect of the invention A is pyridinyl. In another aspect of the invention, A is naphthyl. In yet another aspect of the invention, A is benzo[1,2,5]thiadiazole.

In another aspect of the invention are Formula (2), (3), (4), (5), and (6) compounds

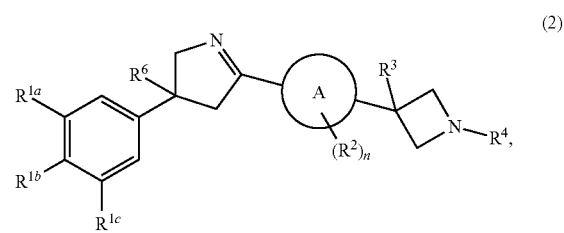

(2)

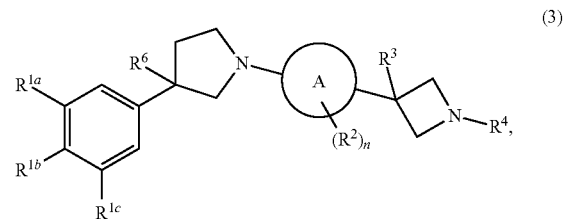

(3)

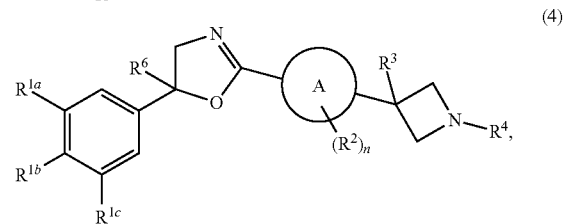

(4)

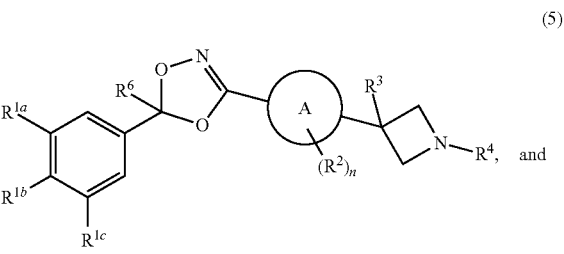

(5) and

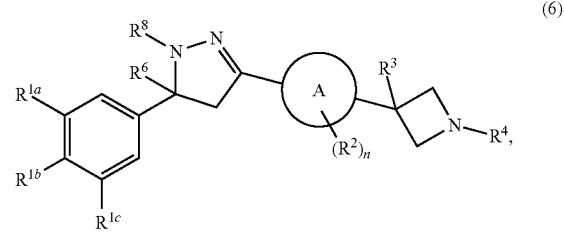

(6)

wherein $R^{1a}$, $R^{1b}$, $R^{1c}$, $R^2$, $R^3$, $R^4$, $R^6$, A, and n are as defined herein.

In yet another aspect of the invention are Formula (2a), (2b), and (2c) compounds

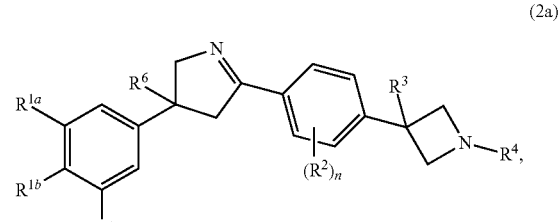
(2a)

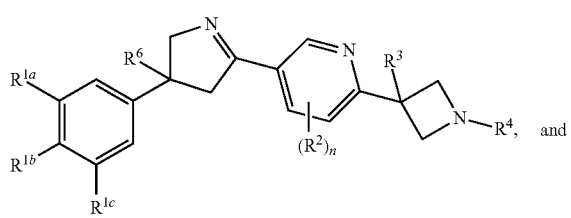
(2b)

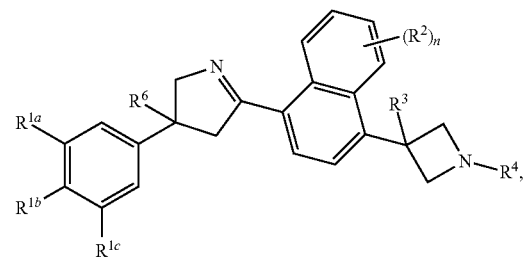
(2c)

wherein $R^{1a}$, $R^{1a}$, $R^{1b}$, $R^{1c}$, $R^2$, $R^3$, $R^4$, $R^6$, and n are as defined herein. It should be noted that when n is the integer 1 or 2 for the naphthyl moiety, the $R^2$ substituent can be located on any one of the carbon atoms, where chemically possible.

In yet another aspect of the invention is a Formula (2a) compound. In yet another aspect of the invention is a Formula (2b) compound. In yet another aspect of the invention is a Formula (2c) compound.

In yet another aspect of the invention are Formula (3a), (3b), and (3c) compounds

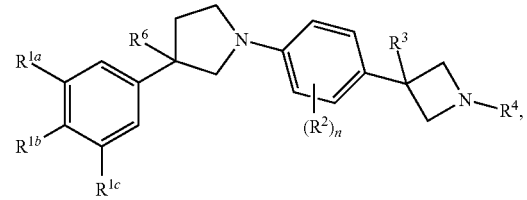
(3a)

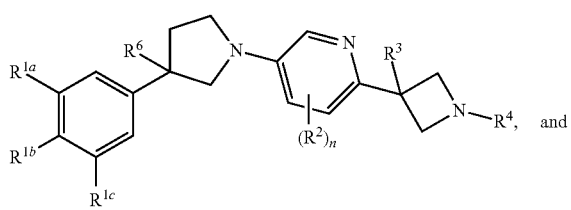
(3b)

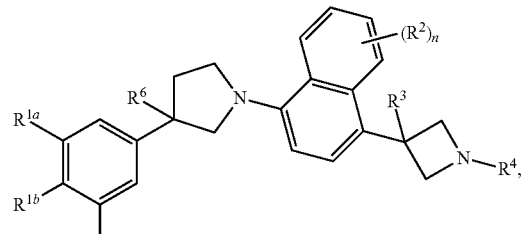
(3c)

wherein $R^{1a}$, $R^{1b}$, $R^{1c}$, $R^2$, $R^3$, $R^4$, $R^6$, and n are as defined herein. It should be noted that when n is the integer 1 or 2 for the naphthyl moiety, the $R^2$ substituent can be located on any one of the carbon atoms, where chemically possible.

In yet another aspect of the invention is a Formula (3a) compound. In yet another aspect of the invention is a Formula (3b) compound. In yet another aspect of the invention is a Formula (3c) compound.

In yet another aspect of the invention are Formula (4a), (4b), and (4c) compounds

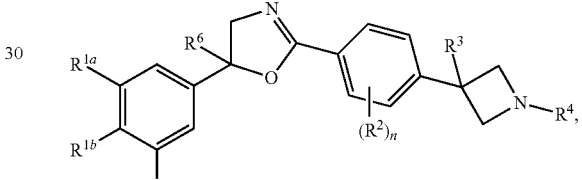
(4a)

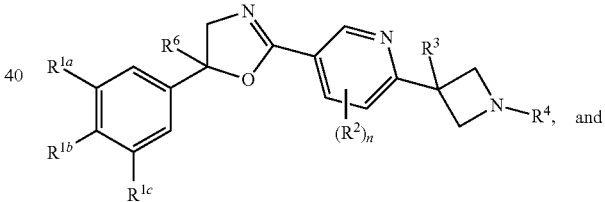
(4b)

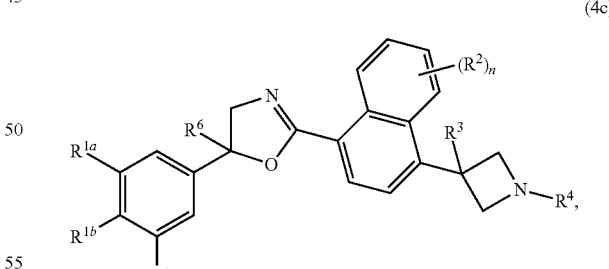
(4c)

wherein $R^{1a}$, $R^{1b}$, $R^{1c}$, $R^2$, $R^3$, $R^4$, $R^6$, and n are as defined herein. It should be noted that when n is the integer 1 or 2 for the naphthyl moiety, the $R^2$ substituent can be located on any one of the carbon atoms, where chemically possible.

In yet another aspect of the invention is a Formula (4a) compound. In yet another aspect of the invention is a Formula (4b) compound. In yet another aspect of the invention is a Formula (4c) compound.

In yet another aspect of the invention are Formula (5a), (5b), and (5c) compounds (5a)
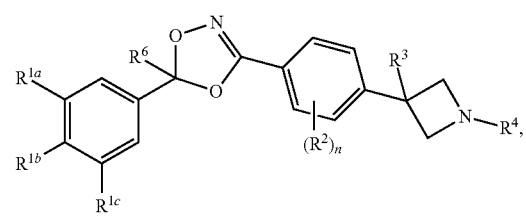

(5b)
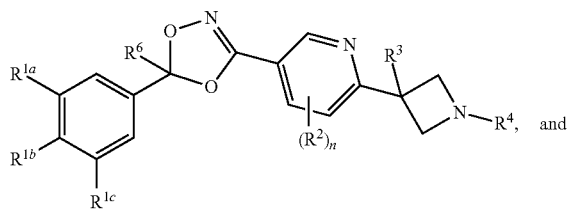

(5c)
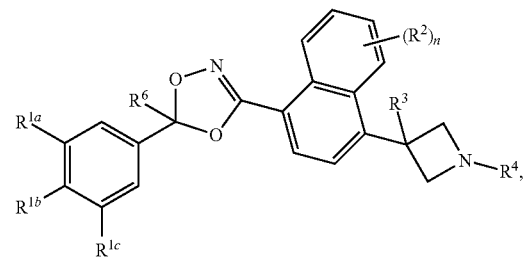

wherein $R^{1a}$, $R^{1b}$, $R^{1c}$, $R^2$, $R^3$, $R^4$, $R^6$, and n are as defined herein. It should be noted that when n is the integer 1 or 2 for the naphthyl moiety, the $R^2$ substituent can be located on any one of the carbon atoms, where chemically possible.

In yet another aspect of the invention is a Formula (5a) compound. In yet another aspect of the invention is a Formula (5b) compound. In yet another aspect of the invention is a Formula (5c) compound.

In yet another aspect of the invention are Formula (6a), (6b), and (6c) compounds (6a)
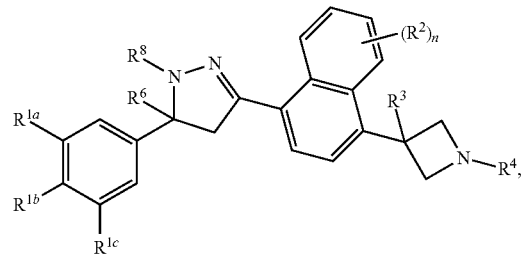

(6b)

(6c)

wherein $R^{1a}$, $R^{1b}$, $R^{1c}$, $R^2$, $R^3$, $R^4$, $R^6$, and n are as defined herein. It should be noted that when n is the integer 1 or 2 for the naphthyl moiety, the $R^2$ substituent can be located on any one of the carbon atoms, where chemically possible.

In yet another aspect of the invention is a Formula (6a) compound. In yet another aspect of the invention is a Formula (6b) compound. In yet another aspect of the invention is a Formula (6c) compound.

In yet another aspect of the invention are Formula (2d), (2e), and (2f) compounds (2d)

(2e)
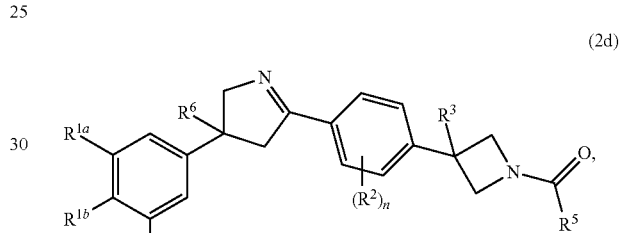

(2f)

wherein $R^{1a}$, $R^{1b}$, $R^{1c}$, $R^2$, $R^3$, $R^4$, $R^6$, and n are as defined herein. It should be noted that when n is the integer 1 or 2 for the naphthyl moiety, the $R^2$ substituent can be located on any one of the carbon atoms within the fused ring, where chemically possible.

In yet another aspect of the invention is a Formula (2d) compound. In yet another aspect of the invention is a Formula (2d) compound wherein $R^6$ is trifluoromethyl and n is the integer 0 that is a Formula (2d1) compound.

In yet another aspect of the invention is a Formula (2e) compound. In yet another aspect of the invention is a Formula (2e) compound wherein $R^6$ is trifluoromethyl and n is the integer 0 that is a Formula (2e1) compound.

In yet another aspect of the invention is a Formula (2f) compound. In yet another aspect of the invention is a Formula (2f) compound wherein $R^6$ is trifluoromethyl and n is the integer 0 that is a Formula (2f1) compound.

In yet another aspect of the invention are Formula (3d), (3e), and (3f) compounds (3d)

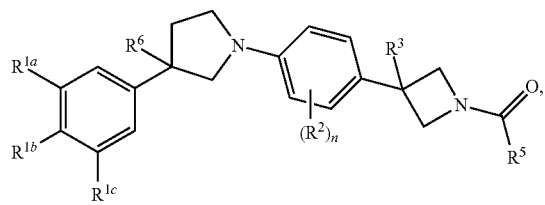

(3e)

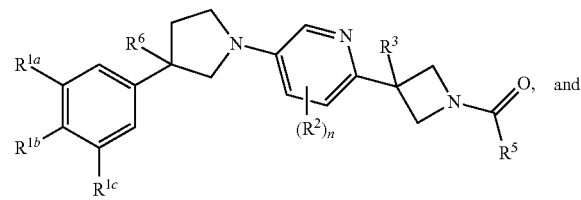

(3f)

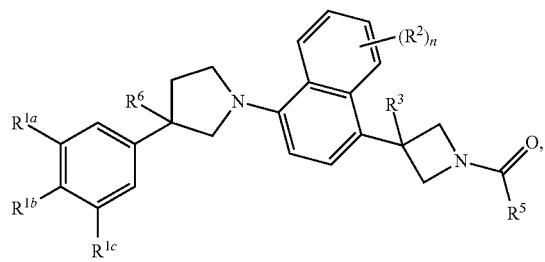

wherein $R^{1a}$, $R^{1b}$, $R^{1c}$, $R^2$, $R^3$, $R^4$, $R^6$, and n are as defined herein. It should be noted that when n is the integer 1 or 2 for the naphthyl moiety, the $R^2$ substituent can be located on any one of the carbon atoms, where chemically possible.

In yet another aspect of the invention is a Formula (3d) compound. In yet another aspect of the invention is a Formula (3d) compound wherein $R^6$ is trifluoromethyl and n is the integer 0 that is a Formula (3d1) compound.

In yet another aspect of the invention is a Formula (3e) compound. In yet another aspect of the invention is a Formula (3e) compound wherein $R^6$ is trifluoromethyl and n is the integer 0 that is a Formula (3e1) compound.

In yet another aspect of the invention is a Formula (3f) compound. In yet another aspect of the invention is a Formula (3f) compound wherein $R^6$ is trifluoromethyl and n is the integer 0 that is a Formula (3f1) compound.

In yet another aspect of the invention are Formula (4d), (4e), and (4f) compounds (4d)

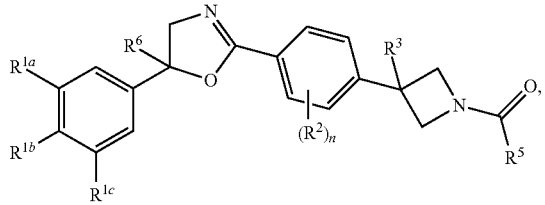

(4e)

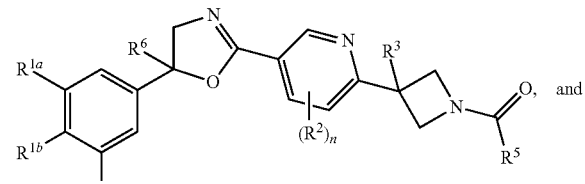

(4f)

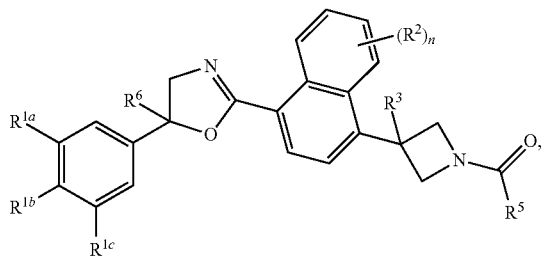

wherein $R^{1a}$, $R^{1b}$, $R^{1c}$, $R^2$, $R^3$, $R^4$, $R^6$, and n are as defined herein. It should be noted that when n is the integer 1 or 2 for the naphthyl moiety, the $R^2$ substituent can be located on any one of the carbon atoms, where chemically possible.

In yet another aspect of the invention is a Formula (4d) compound. In yet another aspect of the invention is a Formula (4d) compound wherein $R^6$ is trifluoromethyl and n is the integer 0 that is a Formula (4d1) compound.

In yet another aspect of the invention is a Formula (4e) compound. In yet another aspect of the invention is a Formula (4e) compound wherein $R^6$ is trifluoromethyl and n is the integer 0 that is a Formula (4e1) compound.

In yet another aspect of the invention is a Formula (4f) compound. In yet another aspect of the invention is a Formula (4f) compound wherein $R^6$ is trifluoromethyl and n is the integer 0 that is a Formula (4f1) compound.

In yet another aspect of the invention are Formula (5d), (5e), and (5f) compounds (5d)

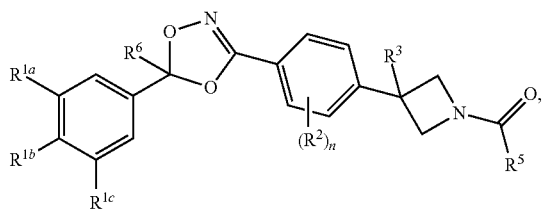

-continued (5e)

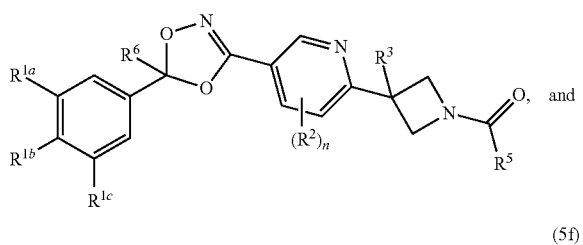

and (5f)

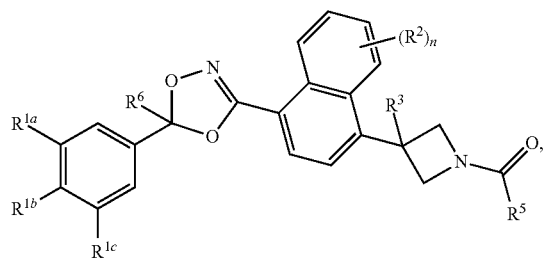

wherein $R^{1a}$, $R^{1b}$, $R^{1c}$, $R^2$, $R^3$, $R^4$, $R^6$, and n are as defined herein. It should be noted that when n is the integer 1 or 2 for the naphthyl moiety, the $R^2$ substituent can be located on any one of the carbon atoms, where chemically possible.

In yet another aspect of the invention is a Formula (5d) compound. In yet another aspect of the invention is a Formula (5d) compound wherein $R^6$ is trifluoromethyl and n is the integer 0 that is a Formula (5d1) compound.

In yet another aspect of the invention is a Formula (5e) compound. In yet another aspect of the invention is a Formula (5e) compound wherein $R^6$ is trifluoromethyl and n is the integer 0 that is a Formula (5e1) compound.

In yet another aspect of the invention is a Formula (5f) compound. In yet another aspect of the invention is a Formula (5f) compound wherein $R^6$ is trifluoromethyl and n is the integer 0 that is a Formula (5f1) compound.

In yet another aspect of the invention are Formula (6d), (6e), and (6f) compounds (6d)

(6e)

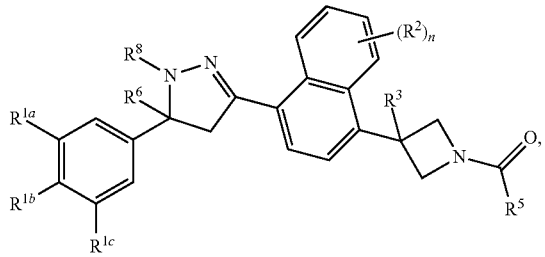

and (6f)

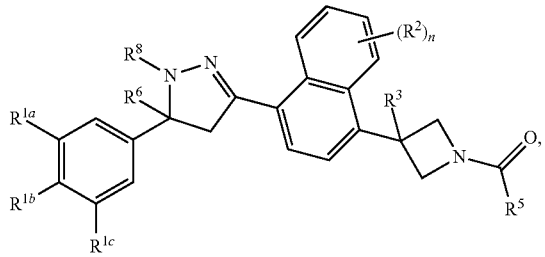

wherein $R^{1a}$, $R^{1b}$, $R^{1c}$, $R^2$, $R^3$, $R^4$, $R^6$, and n are as defined herein. It should be noted that when n is the integer 1 or 2 for the naphthyl moiety, the $R^2$ substituent can be located on any one of the carbon atoms, where chemically possible.

In yet another aspect of the invention is a Formula (6d) compound. In yet another aspect of the invention is a Formula (6d) compound wherein $R^6$ is trifluoromethyl and n is the integer 0 that is a Formula (6d1) compound.

In yet another aspect of the invention is a Formula (6e) compound. In yet another aspect of the invention is a Formula (6e) compound wherein $R^6$ is trifluoromethyl and n is the integer 0 that is a Formula (6e1) compound.

In yet another aspect of the invention is a Formula (6f) compound. In yet another aspect of the invention is a Formula (6f) compound wherein $R^6$ is trifluoromethyl and n is the integer 0 that is a Formula (6f1) compound.

In another aspect of the invention, each of $R^{1a}$, $R^{1b}$, and $R^{1c}$ are independently selected from hydrogen, halo, hydroxyl, cyano, $C_1$-$C_6$alkyl, $C_1$-$C_6$ haloalkyl, $C_0$-$C_3$alkyl$C_3$-$C_6$ cycloalkyl, —S(O)$_p$R, and —SF$_5$. In yet another aspect of the invention, each of $R^{1a}$, $R^{1b}$, and $R^{1c}$ are independently selected from hydrogen, halo, hydroxyl, cyano, $C_1$-$C_6$ haloalkyl, and $C_0$-$C_3$alkyl$C_3$-$C_6$ cycloalkyl. In yet another aspect of the invention, each of $R^{1a}$, $R^{1b}$, and $R^{1c}$ are independently selected from hydrogen, halo, hydroxyl, cyano, and $C_1$-$C_6$ haloalkyl. In yet another aspect of the invention, each of $R^{1a}$, $R^{1b}$, and $R^{1c}$ are independently selected from hydrogen, fluoro, chloro, bromo, cyano, and $C_1$-$C_6$ haloalkyl. In yet another aspect of the invention, each of $R^{1a}$, $R^{1b}$, and $R^{1c}$ are independently selected from hydrogen, fluoro, chloro, bromo, and $C_1$-$C_6$ haloalkyl. In yet another aspect of the invention, each of $R^{1a}$, $R^{1b}$, and $R^{1c}$ are independently selected from hydrogen, fluoro, chloro, bromo, and —CF$_3$. In yet another aspect of the invention, each of $R^{1a}$, $R^{1b}$, and $R^{1c}$ are independently selected from hydrogen, fluoro, chloro, and —CF$_3$.

In yet another aspect of the invention, the integer n of $(R^2)_n$ is 2. When the integer n is 2, then each $R^2$ may be identical or different from each other. In yet another aspect of the invention, the integer n of $(R^2)_n$ is 1. In yet another aspect of the invention, the integer n of $(R^2)_n$ is 0.

In yet another aspect of the invention, $R^2$ is selected from halo, cyano, $C_1$-$C_6$alkyl, $C_1$-$C_6$haloalkyl, hydroxyl, —C(O)NR$^a$R$^b$, $C_2$-$C_6$alkenyl, or —OR. In yet another aspect of the invention, $R^2$ is selected from halo, cyano, $C_1$-$C_6$alkyl, $C_1$-$C_6$haloalkyl, hydroxyl, —C(O)NR$^a$R$^b$, or —OR. In yet another aspect of the invention, $R^2$ is selected from halo, cyano, $C_1$-$C_6$alkyl, —C(O)NR$^a$R$^b$, or hydroxyl. In yet another aspect of the invention, $R^2$ is selected from halo, cyano, —C(O)NR$^a$R$^b$, or hydroxyl. In yet another aspect of the invention, $R^2$ is selected from cyano or —C(O)NR$^a$R$^b$, or hydroxyl. In yet another aspect of the invention, $R^2$ is cyano.

In yet another aspect of the invention, $R^2$ is —C(O)NR$^a$R$^b$. In yet another aspect of the invention, $R^2$ is hydroxyl.

In another aspect of the invention, $R^3$ is hydrogen, halo, hydroxyl, cyano, $C_1$-$C_6$alkyl, $C_1$-$C_6$haloalkyl, $C_0$-$C_3$alkylC$_3$-C$_6$cycloalkyl, —C(O)NH$_2$, —SC(O)R, —C(O)NR$^a$R$^b$, $C_0$-$C_3$alkylNR$^a$R$^4$, —NR$^a$NR$^b$R$^4$, —NR$^a$OR$^b$, —ONR$^a$R$^b$, N$_3$, —NHR$^4$, —OR, or —S(O)$_p$R. In yet another aspect of the invention, $R^3$ is hydrogen, halo, hydroxyl, cyano, $C_1$-$C_6$alkyl, $C_1$-$C_6$haloalkyl, $C_0$-$C_3$alkylC$_3$-C$_6$cycloalkyl, —C(O)NH$_2$, —C(O)NR$^a$R$^b$, $C_0$-$C_3$alkylNR$^a$R$^4$, —NR$^a$NR$^b$R$^4$, —NR$^a$OR$^b$, —ONR$^a$R$^b$, N$_3$, —NHR$^4$, or —S(O)$_p$R. In yet another aspect of the invention, $R^3$ is hydrogen, halo, hydroxyl, cyano, $C_1$-$C_6$alkyl, $C_1$-$C_6$haloalkyl, $C_0$-$C_3$alkylC$_3$-C$_6$cycloalkyl, —C(O)NH$_2$, —C(O)NR$^a$R$^b$, $C_0$-$C_3$alkylNR$^a$R$^4$, —NR$^a$NR$^b$R$^4$, —NHR$^4$, N$_3$, or —S(O)$_p$R. In yet another aspect of the invention, $R^3$ is hydrogen, halo, hydroxyl, cyano, $C_1$-$C_6$alkyl, $C_1$-$C_6$haloalkyl, $C_0$-$C_3$alkylC$_3$-C$_6$cycloalkyl, —C(O)NH$_2$, —C(O)NR$^a$R$^b$, —NHR$^4$, N$_3$, or —S(O)$_p$R. In yet another aspect of the invention, $R^3$ is hydrogen, halo, hydroxyl, cyano, $C_1$-$C_6$alkyl, $C_1$-$C_6$haloalkyl, $C_0$-$C_3$alkylC$_3$-C$_6$cycloalkyl, —C(O)NH$_2$, or N$_3$.

In yet another aspect of the invention, $R^3$ is hydrogen, halo, hydroxyl, cyano, $C_1$-$C_6$alkyl, $C_1$-$C_6$haloalkyl, or N$_3$. In yet another aspect of the invention, $R^3$ is hydrogen, halo, hydroxyl, cyano, $C_1$-$C_6$alkyl, or N$_3$. In yet another aspect of the invention, $R^3$ is hydrogen, halo, hydroxyl, cyano, or N$_3$. In yet another aspect of the invention, $R^3$ is hydrogen, fluoro, chloro, bromo, N$_3$, hydroxyl, or cyano. In yet another aspect of the invention, $R^3$ is hydrogen, fluoro, chloro, N$_3$, hydroxyl, or cyano. In yet another aspect of the invention, $R^3$ is hydrogen, fluoro, hydroxyl, or cyano. In yet another aspect of the invention, $R^3$ is fluoro, chloro, hydroxyl, or cyano. In yet another aspect of the invention, $R^3$ is fluoro, hydroxyl, or cyano. In yet another aspect of the invention, $R^3$ is hydrogen. In yet another aspect of the invention, $R^3$ is fluoro. In yet another aspect of the invention, $R^3$ is chloro. In yet another aspect of the invention, $R^3$ is hydroxyl. In yet another aspect of the invention, $R^3$ is cyano. In yet another aspect of the invention, $R^3$ is N$_3$.

In another aspect of the invention, $R^4$ is $C_1$-$C_6$alkyl, $C_0$-$C_6$alkylC$_3$-C$_6$cycloalkyl, —C(O)R$^5$, —C(S)R$^5$, —C(O)NR$^a$R$^5$, —C(O)C(O)NR$^a$R$^5$, —S(O)$_p$R$^c$, —S(O)$_2$NR$^a$R$^5$, —C(NR$^7$)R$^5$, —C(NR$^7$)NR$^a$R$^5$, $C_0$-$C_6$alkylheteroaryl, or $C_0$-$C_6$-alkylheterocycle; wherein each of $R^4$ and $R^5$ $C_1$-$C_6$alkyl or $C_0$-$C_6$alkylC$_3$-C$_6$cycloalkyl can be optionally and independently substituted as described herein, and wherein each of R$^a$, R$^c$, $R^4$ and $R^5$ substituents can be optionally and independently substituted as described herein. In yet another aspect of the invention, $R^4$ is —C(O)R$^5$, —C(O)NR$^a$R$^5$, —S(O)$_p$R$^c$, —C(S)R$^5$, —S(O)$_2$NR$^a$R$^5$, —C(NR$^7$)R$^5$, or —C(NR$^7$)NR$^a$R$^5$, and wherein each of R$^a$, R$^c$, and $R^5$ substituents can be optionally and independently substituted as described herein. In yet another aspect of the invention, $R^4$ is —C(O)R$^5$, or —C(O)NR$^a$R$^5$, and wherein each of R$^a$ and $R^5$ substituents can be optionally and independently substituted as described herein.

In yet another aspect of the invention, when $R^4$ is —C(O)R$^5$, then $R^5$ is hydrogen, $C_1$-$C_6$alkyl, $C_0$-$C_6$alkylC$_3$-C$_6$cycloalkyl, $C_0$-$C_6$alkylphenyl, $C_0$-$C_6$alkylheteroaryl, or $C_0$-$C_6$alkylheterocycle, wherein said $R^5$ $C_1$-$C_6$alkyl or $C_0$-$C_6$alkylC$_3$-C$_6$cycloalkyl can be optionally and independently substituted by at least one substituent selected from cyano, halo, hydroxyl, oxo, $C_1$-$C_6$alkoxy, $C_1$-$C_6$haloalkoxy, $C_1$-$C_6$haloalkyl, —S(O)$_p$R$^c$, —SH, —S(O)$_p$NR$^a$R$^b$, —NR$^a$R$^b$, —NR$^a$C(O)R$^b$, —SC(O)R$^c$, —SCN, or —C(O)NR$^a$R$^b$, where said $R^5$ $C_0$-$C_6$alkylphenyl, $C_0$-$C_6$alkylheteroaryl, or $C_0$-$C_6$alkylheterocycle moiety can be further optionally substituted with at least one substituent selected from cyano, halo, hydroxyl, $C_1$-$C_6$alkoxy, $C_1$-$C_6$alkyl, $C_1$-$C_6$haloalkyl, —SH, —S(O)$_p$R, and $C_1$-$C_6$haloalkoxy. The R$^a$ and R$^c$ substituents are also optionally substituted with at least one substituent as defined herein.

In yet another aspect of the invention, when $R^4$ is —C(O)R$^5$, then $R^5$ is hydrogen, $C_1$-$C_6$alkyl, $C_0$-$C_6$alkylC$_3$-C$_6$cycloalkyl, or $C_0$-$C_6$alkylheteroaryl, where said $C_0$-$C_6$alkylC$_3$-C$_6$cycloalkyl or $C_0$-$C_6$alkylheteroaryl moieties are optionally substituted as defined herein.

In yet another aspect of the invention, when $R^4$ is —C(O)R$^5$, then $R^5$ is methyl, ethyl, propyl, isopropyl, isobutyl, n-butyl, t-butyl, cyclopropyl, cyclobutyl, cyclopentyl, —CH$_2$-cyclopropyl, —CH$_2$-cyclobutyl, —CH$_2$-cyclopentyl, —(CH$_2$)$_2$-cyclopropyl, —(CH$_2$)$_2$-cyclobutyl, —(CH$_2$)$_2$-cyclopentyl, pyrazolyl, —CH$_2$-pyrazolyl, —(CH$_2$)$_2$-pyrazolyl, pyridinyl, —CH$_2$-pyridinyl, —(CH$_2$)$_2$-pyridinyl, wherein the $R^5$ substituent can be optionally and independently substituted as defined herein.

In yet another aspect of the invention, when $R^4$ is —C(O)R$^5$, then $R^5$ is methyl, ethyl, propyl, isopropyl, isobutyl, n-butyl, t-butyl, cyclopropyl, cyclobutyl, cyclopentyl, —CH$_2$-cyclopropyl, —CH$_2$-cyclobutyl, —CH$_2$-cyclopentyl, —(CH$_2$)$_2$-cyclopropyl, —(CH$_2$)$_2$-cyclobutyl, —(CH$_2$)$_2$-cyclopentyl, pyrazolyl, —CH$_2$-pyrazolyl, —(CH$_2$)$_2$-pyrazolyl, pyridinyl, —CH$_2$-pyridinyl, —(CH$_2$)$_2$-pyridinyl, wherein the $R^5$ can be optionally and independently substituted by at least one substituent selected from cyano, halo, hydroxyl, oxo, methoxy, —CF$_3$, ethoxy, —S(O)$_p$R, —SCH$_3$, —SCH$_2$CH$_3$, —NH$_2$, —NHCH$_3$, —NHCH$_2$CH$_3$, —NH(CH$_2$)$_2$CH$_3$, —NHcyclopropyl, —NHcyclobutyl, —NHCH$_2$cyclopropyl, —NHCH$_2$cyclobutyl, —NR$^a$C(O)R$^b$, —C(O)NH$_2$, or —C(O)NR$^a$R$^5$.

In yet another aspect of the invention, when $R^4$ is —C(O)R$^5$, then $R^5$ is methyl, ethyl, propyl, isopropyl, isobutyl, cyclopropyl, cyclobutyl, cyclopentyl, —CH$_2$-cyclopropyl, —CH$_2$-cyclobutyl, —CH$_2$-cyclopentyl, pyrazolyl, —CH$_2$-pyrazolyl, pyridinyl, —CH$_2$-pyridinyl, wherein the $R^5$ substituent can be optionally and independently substituted by at least one substituent selected from cyano, halo, hydroxyl, oxo, —CF$_3$, S(O)$_p$R, methoxy, ethoxy, —SCH$_3$, —NH$_2$, —NHCH$_3$, —NHCH$_2$CH$_3$, —NHcyclopropyl, —NHcyclobutyl, —NHC(O)H, —C(O)NH$_2$, or —C(O)NR$^a$R$^5$.

In yet another aspect of the invention, when $R^4$ is —C(O)R$^5$, then $R^5$ is methyl, ethyl, propyl, isopropyl, isobutyl, cyclopropyl, cyclobutyl, cyclopentyl, —CH$_2$-cyclopropyl, —CH$_2$-cyclobutyl, —CH$_2$-cyclopentyl, pyrazolyl, —CH$_2$-pyrazolyl, pyridinyl, —CH$_2$-pyridinyl, wherein the alkyl (for example, methyl, ethyl, and isopropyl), cycloalkyl (for example, cyclopropyl and cyclobutyl) or alkylcycloalkyl (for example, —CH$_2$cyclopropyl) can be optionally and independently substituted by at least one substituent selected from cyano, halo, hydroxyl, oxo, —CF$_3$, methoxy, —SCH$_3$, S(O)$_p$R, —NH$_2$, —NHCH$_3$, —NHCH$_2$CH$_3$, —NHcyclopropyl, —NHC(O)H, —C(O)NH$_2$, or —C(O)NR$^a$R$^5$.

In yet another aspect of the invention, when $R^4$ is —C(O)R$^5$, then $R^5$ is oxetane, thiatane, azetidine, tetrahydrofuran, tetrahydrothiophene, pyrrolidine, —CH$_2$-oxetane, —CH$_2$-thiatane, —CH$_2$-azetidine, or —CH$_2$-tetrahydrofuran, each of which are optionally substituted as defined herein. In yet another aspect of the invention, when $R^4$ is —C(O)R$^5$, then $R^5$ is oxetane, thiatane, azetidine, tetrahydrofuran, tetrahydrothiophene, —CH$_2$-oxetane, —CH$_2$-thiatane, or —CH$_2$-azetidine, each of which are optionally substituted as defined herein. In yet another aspect of the invention, when $R^4$ is —C(O)R$^5$, then $R^5$ is oxetane, thiatane, azetidine, —CH$_2$- oxetane, —CH$_2$-thiatane, or —CH$_2$-azetidine, each of which are optionally substituted as defined herein. In yet another aspect of the invention, when R$^4$ is —C(O)R$^5$, then R$^5$ is oxetane, thiatane, or azetidine, each of which are optionally substituted as defined herein. In yet another aspect of the invention, when R$^4$ is —C(O)R$^5$, then R$^5$ is —CH$_2$-oxetane, —CH$_2$-thiatane, or —CH$_2$-azetidine, each of which are optionally substituted as defined herein.

In yet another aspect of the invention, when R$^4$ is —C(O)R$^5$, then R$^5$ is pyrazole, imidazole, isoxazole, oxazole, isothiazole, thiazole, triazole, pyridine, pyridazine, pyrazine, or pyrimidine, each of the which are optionally substituted as defined herein.

In yet another aspect of the invention, when R$^4$ is —C(O)R$^5$, then R$^5$ is C$_1$-C$_6$alkyl, C$_2$-C$_6$alkenyl, or C$_0$-C$_6$alkylC$_3$-C$_6$cycloalkyl, wherein each of C$_1$-C$_6$alkyl or C$_0$-C$_6$alkylC$_3$-C$_6$cycloalkyl is optionally substituted with at least one substituent selected from cyano, halo, hydroxyl, —S(O)$_p$R$^c$, C$_1$-C$_6$alkoxy, —S(O)$_p$NR$^a$R$^b$, or —SC(O)R$^c$; pyrazole, pyridine, oxazole, pyridazine, triazole, azetidine, thiatane, wherein each heterocycle and heteroaryl moiety are optionally substituted further with at least one substituent selected from fluoro, hydroxyl, methyl, and oxo; where p, R$^a$, R$^b$, and R$^c$ are as defined herein.

In yet another aspect of the invention, when R$^4$ is —C(O)NR$^a$R$^5$, then R$^a$ is hydrogen, methyl, ethyl, propyl, isopropyl, cyclopropyl, cyclobutyl, cyclopentyl, —CH$_2$-cyclopropyl, —CH$_2$-cyclobutyl, —CH$_2$-cyclopentyl, —(CH$_2$)$_2$-cyclopropyl, —(CH$_2$)$_2$-cyclobutyl, or —(CH$_2$)$_2$-cyclopentyl; wherein the alkyl (for example methyl and propyl), cycloalkyl (for example, cyclopropyl and cyclopentyl), or the alkylcycloalkyl (for example, —CH$_2$-cyclopropyl, —CH$_2$-cyclopentyl, and —(CH$_2$)$_2$-cyclobutyl) are optionally substituted by cyano or at least one halo substituent; and R$^5$ is as defined herein.

In yet another aspect of the invention, when R$^4$ is —C(O)NR$^a$R$^5$, then R$^a$ is hydrogen, methyl, ethyl, propyl, isopropyl, cyclopropyl, cyclobutyl, cyclopentyl, —CH$_2$-cyclopropyl, —CH$_2$-cyclobutyl, —CH$_2$-cyclopentyl; wherein the alkyl (for example, methyl and propyl), cycloalkyl (for example, cyclopropyl and cyclopentyl), or the alkylcycloalkyl (for example, —CH$_2$-cyclopropyl and —CH$_2$-cyclopentyl) are optionally substituted by cyano or at least one halo substituent; and R$^5$ is as defined herein.

In yet another aspect of the invention, when R$^4$ is —C(O)NR$^a$R$^5$, then R$^a$ is hydrogen or methyl and R$^5$ is selected from hydrogen, methyl, ethyl, propyl, cyclopropyl, and C$_0$-C$_6$alkylheterocycle, wherein the alkyl and alkylheterocycle moiety are each optionally substituted as described herein.

In yet another aspect of the invention, when R$^4$ is —S(O)$_p$R$^c$, the integer p is 2, and R$^c$ is as defined herein, and said R$^c$ substituent is optionally substituted with at least one substituent as defined herein. In yet another aspect of the invention, when R$^4$ is —S(O)$_p$R$^c$, the integer p is 2, R$^c$ is C$_1$-C$_6$alkyl optionally substituted with at least one substituent as defined herein. In yet another aspect of the invention, when R$^4$ is —S(O)$_p$R$^c$, the integer p is 2, R$^c$ is C$_1$-C$_6$alkyl optionally substituted with at least one substituent selected from cyano or halo. In yet another aspect of the invention, when R$^4$ is —S(O)$_p$R$^c$, the integer p is 2, and R$^c$ is C$_1$-C$_6$alkyl. In yet another aspect of the invention, when R$^4$ is —S(O)$_p$R$^c$, the integer p is 2, and R$^c$ is methyl, ethyl, propyl, or isopropyl. In yet another aspect of the invention, when R$^4$ is —S(O)$_p$R$^c$, the integer p is 2, and R$^c$ is methyl or ethyl.

In yet another aspect of the invention, R$^6$ is cyano, C$_1$-C$_6$alkyl, C$_1$-C$_6$haloalkyl, or —C(O)NH$_2$. In yet another aspect of the invention, R$^6$ is cyano, C$_1$-C$_6$alkyl, or C$_1$-C$_6$haloalkyl. In yet another aspect of the invention, R$^6$ is cyano, methyl, ethyl, or C$_1$-C$_6$haloalkyl. In yet another aspect of the invention, R$^6$ is cyano, methyl, or C$_1$-C$_6$haloalkyl. In yet another aspect of the invention, R$^6$ is cyano or C$_1$-C$_6$haloalkyl. In yet another aspect of the invention, R$^6$ is C$_1$-C$_6$haloalkyl. In yet another aspect of the invention, R$^6$ is —CF$_3$, —CHF$_2$, —CH$_2$F, and —CF$_2$Cl. In yet another aspect of the invention, R$^6$ is —CF$_3$, —CHF$_2$, and —CH$_2$F. In yet another aspect of the invention, R$^6$ is —CF$_3$.

In yet another aspect of the invention, R$^7$ is hydrogen, methyl, ethyl, propyl, isopropyl, butyl, hydroxyl, cyano, nitro, —S(O)$_p$R$^c$, or C$_1$-C$_6$alkoxy. In yet another aspect of the invention, R$^7$ is hydrogen, methyl, ethyl, propyl, isopropyl, butyl, cyano, —S(O)$_p$R$^c$, or C$_1$-C$_6$alkoxy. In yet another aspect of the invention, R$^7$ is hydrogen, methyl, ethyl, propyl, isopropyl, butyl, cyano, —S(O)$_p$R$^c$, or methoxy. In yet another aspect of the invention, R$^7$ is hydrogen, methyl, ethyl, propyl, isopropyl, or methoxy. In yet another aspect of the invention, R$^7$ is hydrogen, methyl, ethyl, propyl, or methoxy.

In yet another aspect of the invention, R$^8$ is hydrogen, methyl, ethyl, propyl, isopropyl, hydroxyl, cyano, —S(O)$_p$R$^c$, or C$_1$-C$_6$alkoxy. In yet another aspect of the invention, R$^8$ is hydrogen, methyl, ethyl, propyl, isopropyl, cyano, —S(O)$_p$R$^c$, methoxy, or ethoxy. In yet another aspect of the invention, R$^8$ is hydrogen, methyl, ethyl, propyl, isopropyl, cyano, or methoxy. In yet another aspect of the invention, R$^8$ is hydrogen, methyl, ethyl, propyl, or methoxy.

In yet another aspect of the invention, R is methyl, ethyl, propyl, isopropyl, cyclopropyl, cyclobutyl, or cyclopentyl. In yet another aspect of the invention, R is methyl, ethyl, isopropyl, cyclopropyl, or cyclobutyl.

In yet another aspect of the invention, R$^a$ is hydrogen, methyl, ethyl, propyl, isopropyl, or isobutyl, each alkyl moiety is optionally substituted as defined herein. In yet another aspect of the invention, R$^a$ is hydrogen, methyl, ethyl, propyl, or isopropyl, each alkyl moiety is optionally substituted as defined herein. In yet another aspect of the invention, R$^a$ is hydrogen, methyl, or ethyl, each alkyl is optionally substituted as defined herein.

In yet another aspect of the invention, R$^a$ is hydrogen, methyl, ethyl, propyl, isopropyl, isobutyl, cyclopropyl, cyclobutyl, cyclopentyl, —CH$_2$-cyclopropyl, or —CH$_2$-cyclobutyl, each alkyl, cycloalkyl, and alkylcycloalkyl moiety is optionally substituted as defined herein. In yet another aspect of the invention, R$^a$ is hydrogen, methyl, ethyl, propyl, isopropyl, cyclopropyl, cyclobutyl, —CH$_2$-cyclopropyl, or —CH$_2$-cyclobutyl, each alkyl, cycloalkyl, and alkylcycloalkyl moiety is optionally substituted as defined herein. In yet another aspect of the invention, R$^a$ is hydrogen, methyl, ethyl, isopropyl, cyclopropyl, cyclobutyl, —CH$_2$-cyclopropyl, or —CH$_2$-cyclobutyl, each alkyl, cycloalkyl, and alkylcycloalkyl moiety is optionally substituted as defined herein.

In another aspect of the invention, R$^b$ is hydrogen, C$_1$-C$_6$alkyl, C$_3$-C$_6$cycloalkyl, C$_0$-C$_3$alkylphenyl, or C$_0$-C$_3$alkylheteroaryl. In yet another aspect of the invention, R$^b$ is hydrogen, C$_1$-C$_6$alkyl, C$_3$-C$_6$cycloalkyl, or C$_0$-C$_3$alkylheteroaryl. In yet another aspect of the invention, R$^b$ is hydrogen, C$_1$-C$_6$alkyl, or C$_3$-C$_6$cycloalkyl. In yet another aspect of the invention, R$^b$ is hydrogen, methyl, ethyl, isopropyl, propyl, isobutyl, cyclopropyl, or cyclobutyl.

In yet another aspect of the invention, the sulfur atom of any thiatanyl moiety can be optionally substituted as defined herein, for example with one or two oxygen atoms and an alkyl group.

In yet another aspect of the invention, when A is phenyl, naphthyl, or pyridinyl, then R$^{1a}$, R$^{1b}$, and R$^{1c}$ are each independently selected from hydrogen, halo, hydroxyl, and $C_1$-$C_6$ haloalkyl; and $R^2$ is halo, cyano, hydroxyl, $C_1$-$C_6$alkyl, $C_1$-$C_6$haloalkyl, —C(O)NR$^a$R$^b$, or —OR; and $R^3$ is hydrogen, halo, hydroxyl, $N_3$, or cyano; and $R^4$ is —C(O)R$^5$; and $R^6$ is $C_1$-$C_6$haloalkyl, stereoisomers thereof, and pharmaceutically or veterinarily acceptable salts thereof. In yet another aspect of the invention, when A is phenyl, then $R^{1a}$, $R^{1b}$, and $R^{1c}$ are each independently selected from hydrogen, halo, and $CF_3$; and $R^3$ is halo or hydroxyl; and $R^6$ is $CF_3$; stereoisomers thereof, and pharmaceutically or veterinarily acceptable salts thereof.

In yet another aspect of the invention is a compound of Formula (1) selected from:
1-(3-{4-[4-(3,5-dichloro-phenyl)-4-trifluoromethyl-4,5-dihydro-3H-pyrrol-2-yl]-phenyl}-3-fluoro-azetidin-1-yl)-2-methanesulfonyl-ethanone;
1-(3-{4-[4-(3,5-dichloro-phenyl)-4-trifluoromethyl-4,5-dihydro-3H-pyrrol-2-yl]-phenyl}-3-fluoro-azetidin-1-yl)-2-methyl-propan-1-one;
3-(3,5-dichloro-4-fluorophenyl)-5-(4-{3-fluoro-1-[(methylsulfonyl)-acetyl]azetidin-3-yl}phenyl)-3-(trifluoromethyl)-3,4-dihydro-2H-pyrrole;
3-(3,5-dichloro-4-fluorophenyl)-5-[4-(3-fluoro-1-isobutyrylazetidin-3-yl)phenyl]-3-(trifluoromethyl)-3,4-dihydro-2H-pyrrole;
1-(3-fluoro-3-{4-[4-(3,4,5-trichloro-phenyl)-4-trifluoromethyl-4,5-dihydro-3H-pyrrol-2-yl]-phenyl}azetidin-1-yl)-2-methanesulfonyl-ethanone;
5-[4-(3-fluoro-1-isobutyrylazetidin-3-yl)phenyl]-3-(3,4,5-trichloro-phenyl)-3-(trifluoromethyl)-3,4-dihydro-2H-pyrrole;
1-(3-{4-[5-(3,5-dichloro-4-fluoro-phenyl)-5-trifluoromethyl-[1,4,2]dioxazol-3-yl]-phenyl}-3-fluoro-azetidin-1-yl)-2-methanesulfonyl-ethanone;
1-(3-{4-[5-(3,5-dichloro-4-fluoro-phenyl)-5-trifluoromethyl-[1,4,2]dioxazol-3-yl]-phenyl}-3-fluoro-azetidin-1-yl)-2-methyl-propan-1-one;
1-(3-{4-[5-(3,5-dichloro-phenyl)-5-trifluoromethyl-[1,4,2]dioxazol-3-yl]-phenyl}-3-fluoro-azetidin-1-yl)-2-methanesulfonyl-ethanone;
1-(3-{4-[5-(3,5-dichloro-phenyl)-5-trifluoromethyl-[1,4,2]dioxazol-3-yl]-phenyl}-3-fluoro-azetidin-1-yl)-2-methyl-propan-1-one;
1-(3-fluoro-3-{4-[5-(3,4,5-trichloro-phenyl)-5-trifluoromethyl-[1,4,2]dioxazol-3-yl]-phenyl}-azetidin-1-yl)-2-methanesulfonyl-ethanone;
1-(3-fluoro-3-{4-[5-(3,4,5-trichloro-phenyl)-5-trifluoromethyl-[1,4,2]dioxazol-3-yl]-phenyl}-azetidin-1-yl)-2-methyl-propan-1-one;
1-(3-fluoro-3-{4-[5-(3,4,5-trichloro-phenyl)-5-trifluoromethyl-4,5-dihydro-1H-pyrazol-3-yl]-phenyl}-azetidin-1-yl)-2-methyl-propan-1-one;
1-(3-{4-[5-(3,5-dichloro-4-fluoro-phenyl)-5-trifluoromethyl-4,5-dihydro-1H-pyrazol-3-yl]-phenyl}-3-fluoro-azetidin-1-yl)-2-methyl-propan-1-one;
1-(3-fluoro-3-(4-(5-(3,4,5-trichlorophenyl)-5-(trifluoromethyl)-4,5-dihydro-1H-pyrazol-3-yl)phenyl)azetidin-1-yl)-2-(methylsulfonyl)ethanone;
1-(3-(4-(5-(3,5-dichlorophenyl)-5-(trifluoromethyl)-4,5-dihydro-1H-pyrazol-3-yl)phenyl)-3-fluoroazetidin-1-yl)-2-(methylsulfonyl)ethanone;
1-(3-(4-(5-(3,5-dichlorophenyl)-5-(trifluoromethyl)-4,5-dihydro-1H-pyrazol-3-yl)phenyl)-3-fluoroazetidin-1-yl)-2-methylpropan-1-one; and
1-(3-(4-(5-(3,5-dichloro-4-fluorophenyl)-5-(trifluoromethyl)-4,5-dihydro-1H-pyrazol-3-yl)phenyl)-3-fluoroazetidin-1-yl)-2-(methylsulfonyl)ethanone, stereoisomers thereof, and pharmaceutically or veterinarily acceptable salts thereof.

In yet another aspect of the invention is a compound of Formula (1) selected from:
1-(3-{4-[4-(3,5-dichloro-phenyl)-4-trifluoromethyl-4,5-dihydro-3H-pyrrol-2-yl]-phenyl}-3-fluoro-azetidin-1-yl)-2-methanesulfonyl-ethanone;
1-(3-{4-[4-(3,5-dichloro-phenyl)-4-trifluoromethyl-4,5-dihydro-3H-pyrrol-2-yl]-phenyl}-3-fluoro-azetidin-1-yl)-2-methyl-propan-1-one;
3-(3,5-dichloro-4-fluorophenyl)-5-(4-{3-fluoro-1-[(methylsulfonyl)-acetyl]azetidin-3-yl}phenyl)-3-(trifluoromethyl)-3,4-dihydro-2H-pyrrole;
3-(3,5-dichloro-4-fluorophenyl)-5-[4-(3-fluoro-1-isobutyrylazetidin-3-yl)phenyl]-3-(trifluoromethyl)-3,4-dihydro-2H-pyrrole;
1-(3-fluoro-3-{4-[4-(3,4,5-trichloro-phenyl)-4-trifluoromethyl-4,5-dihydro-3H-pyrrol-2-yl]-phenyl}-azetidin-1-yl)-2-methanesulfonyl-ethanone; and
5-[4-(3-fluoro-1-isobutyrylazetidin-3-yl)phenyl]-3-(3,4,5-trichloro-phenyl)-3-(trifluoromethyl)-3,4-dihydro-2H-pyrrole, stereoisomers thereof, and pharmaceutically or veterinarily acceptable salts thereof.

In yet another aspect of the invention is a compound of Formula (1) selected from:
1-(3-{4-[5-(3,5-dichloro-4-fluoro-phenyl)-5-trifluoromethyl-[1,4,2]dioxazol-3-yl]-phenyl}-3-fluoro-azetidin-1-yl)-2-methanesulfonyl-ethanone;
1-(3-{4-[5-(3,5-dichloro-4-fluoro-phenyl)-5-trifluoromethyl-[1,4,2]dioxazol-3-yl]-phenyl}-3-fluoro-azetidin-1-yl)-2-methyl-propan-1-one;
1-(3-{4-[5-(3,5-dichloro-phenyl)-5-trifluoromethyl-[1,4,2]dioxazol-3-yl]-phenyl}-3-fluoro-azetidin-1-yl)-2-methanesulfonyl-ethanone;
1-(3-{4-[5-(3,5-dichloro-phenyl)-5-trifluoromethyl-[1,4,2]dioxazol-3-yl]-phenyl}-3-fluoro-azetidin-1-yl)-2-methyl-propan-1-one;
1-(3-fluoro-3-{4-[5-(3,4,5-trichloro-phenyl)-5-trifluoromethyl-[1,4,2]dioxazol-3-yl]-phenyl}-azetidin-1-yl)-2-methanesulfonyl-ethanone; and
1-(3-fluoro-3-{4-[5-(3,4,5-trichloro-phenyl)-5-trifluoromethyl-[1,4,2]dioxazol-3-yl]-phenyl}-azetidin-1-yl)-2-methyl-propan-1-one, stereoisomers thereof, and pharmaceutically or veterinarily acceptable salts thereof.

In yet another aspect of the invention is a compound of Formula (1) selected from:
1-(3-fluoro-3-{4-[5-(3,4,5-trichloro-phenyl)-5-trifluoromethyl-4,5-dihydro-1H-pyrazol-3-yl]-phenyl}-azetidin-1-yl)-2-methyl-propan-1-one;
1-(3-{4-[5-(3,5-dichloro-4-fluoro-phenyl)-5-trifluoromethyl-4,5-dihydro-1H-pyrazol-3-yl]-phenyl}-3-fluoro-azetidin-1-yl)-2-methyl-propan-1-one;
1-(3-fluoro-3-(4-(5-(3,4,5-trichlorophenyl)-5-(trifluoromethyl)-4,5-dihydro-1H-pyrazol-3-yl)phenyl)azetidin-1-yl)-2-(methylsulfonyl)ethanone;
1-(3-(4-(5-(3,5-dichlorophenyl)-5-(trifluoromethyl)-4,5-dihydro-1H-pyrazol-3-yl)phenyl)-3-fluoroazetidin-1-yl)-2-(methylsulfonyl)ethanone;
1-(3-(4-(5-(3,5-dichlorophenyl)-5-(trifluoromethyl)-4,5-dihydro-1H-pyrazol-3-yl)phenyl)-3-fluoroazetidin-1-yl)-2-methylpropan-1-one; and
1-(3-(4-(5-(3,5-dichloro-4-fluorophenyl)-5-(trifluoromethyl)-4,5-dihydro-1H-pyrazol-3-yl)phenyl)-3-fluoroazetidin-1-yl)-2-(methylsulfonyl)ethanone, stereoisomers thereof, and pharmaceutically or veterinarily acceptable salts thereof.

In yet another aspect of the invention is a composition that comprises (a) a Formula (1) compound, stereoisomers thereof, or a veterinarily or pharmaceutically acceptable salt thereof, and (b) a veterinarily or pharmaceutically acceptable excipient, diluent, or carrier. The variables $R^{1a}$, $R^{1b}$, $R^{1c}$, $R^2$, $R^3$, $R^4$, $R^6$, and n are as defined herein. Preferably, the composition comprises a therapeutically effective amount of a Formula (1) compound, stereoisomer thereof, or veterinarily or pharmaceutically acceptable salt thereof, and a veterinarily or pharmaceutically acceptable excipient, diluent, or carrier. The composition may comprise at least one additional veterinary agent. Preferred additional veterinary agents include endoparasiticides, endectocides, ectoparasiticides, insecticides, and anthelmintics, and are described herein.

The composition may comprise at least one additional veterinary agent. Preferred additional veterinary agents include endoparasiticides, endectocides, ectoparasiticides, insecticides, and anthelmintics, and are described herein. In one aspect of the invention, the additional veterinary agent is selected from amitraz, amino acetonitriles, anthelmintics (e.g., albendazole, cambendazole, fenbendazole, flubendazole, mebendazole, octadepsipeptides, oxfendazole, oxibendazole, paraherquamide, parbendazole, piperazines, praziquantel, thiabendazole, tetramisole, triclabendazole, levamisole, pyrantel pamoate, oxantel, morantel, and the like), avermectins (e.g., abamectin, doramectin, emamectin, eprinomectin, ivermectin, moxidectin, selamectin, and the like), milbemycin, milbemycin oxime, demiditraz, diethylcarbamazine, fipronil, hydroprene, kinoprene, methoprene, metaflumizone, niclosamide, permethrin, pyrethrins, pyriproxyfen, and spinosad. In another aspect of the invention, the additional agent is selected from an amino acetonitrile, albendazole, cambendazole, fenbendazole, flubendazole, mebendazole, oxfendazole, oxibendazole, paraherquamide, parbendazole, praziquantel, thiabendazole, tetramisole, triclabendazole, levamisole, pyrantel pamoate, oxantel, morantel, abamectin, doramectin, emamectin, eprinomectin, ivermectin, moxidectin, selamectin, milbemycin, milbemycin oxime, demiditraz, diethylcarbamazine, fipronil, hydroprene, kinoprene, methoprene, metaflumizone, niclosamide, pyriproxyfen, spinosad, and mixtures thereof. In yet another aspect of the invention, the additional agent is selected from an amino acetonitrile, pyrantel, paraherquamide, praziquantel, abamectin, doramectin, emamectin, eprinomectin, ivermectin, moxidectin, selamectin, milbemycin, and milbemycin oxime, and mixtures thereof. In yet another aspect of the invention, the additional agent is selected from abamectin, doramectin, emamectin, eprinomectin, ivermectin, moxidectin, selamectin, milbemycin, and milbemycin oxime, and mixtures thereof. In yet another aspect of the invention, the additional agent is selected from abamectin, doramectin, eprinomectin, ivermectin, moxidectin, selamectin, milbemycin, and milbemycin oxime, and mixtures thereof. In yet another aspect of the invention, the additional agent is selected from moxidectin, selamectin, and milbemycin oxime, and mixtures thereof. In yet another aspect of the invention, the additional agent is selected from moxidectin and milbemycin oxime, and mixtures thereof. In yet another aspect of the invention, the additional agent is praziquantel, moxidectin, milbemycin oxime, pyrantel, and mixtures thereof. In another aspect of the invention, the additional agent is moxidectin. In another aspect of the invention, the additional agent is milbemycin oxime. In another aspect of the invention, the additional agent is pyrantel.

In yet another aspect of the invention is the use of a Formula (1) compound for the manufacture of a medicament.

In yet another aspect of the invention is a method for treating a parasitic infection or infestation in an animal that includes the step of administering to said animal, in need of such treatment, a therapeutically effective amount of a compound of the present invention, stereoisomer thereof, or veterinarily acceptable salt thereof. In one aspect, the animal is a mammal, specifically a companion animal (for example, dog, cat, or horse) or livestock (for example, sheep, goat, cattle, and pig). In another aspect, the animal is a bird, specifically, fowl (for example, chicken, turkey, duck, and geese). In another aspect, the animal is a fish. The compounds of the present invention, and compositions thereof, can be administered to the animal orally or topically. The compounds of the present invention, and compositions thereof, can also be administered to the animal by intramuscular-, intraperitoneal-, or subcutaneous-injection. Preferably, the compounds of the present invention, and compositions thereof, can be administered to the animal orally or topically.

In yet another aspect of the invention is a method for treating a parasitic infection or infestation in an animal that includes the step of administering to said animal, in need of such treatment, a therapeutically effective amount of a compound of the present invention, stereoisomer thereof, or veterinarily acceptable salt thereof, in combination with at least one additional veterinary agent. In one aspect, the animal is a mammal, specifically a companion animal (for example, dog, cat, or horse) or livestock (for example, sheep, goat, cattle, and pig). In another aspect, the animal is a bird, specifically, fowl (for example, chicken, turkey, duck, and geese). In another aspect, the animal is a fish. The compounds of the present invention, and compositions thereof, can be administered to the animal orally or topically. The compounds of the present invention, and compositions thereof, can also be administered to the animal by intramuscular-, intraperitoneal-, or subcutaneous-injection. Preferably, the compounds of the present invention, and compositions thereof, can be administered to the animal orally or topically. Equally preferred, the compounds of the present invention can be administered by injection.

Compounds of the present invention alone, or in combination with an additional veterinary agent(s) may be administered as (a) a single veterinary composition which comprises a compound of the present invention, stereoisomer thereof, veterinarily acceptable salt thereof, and optionally, at least one additional veterinary agent as described herein and a veterinarily acceptable excipient, diluent, or carrier; or (b) two separate veterinary compositions comprising (i) a first composition comprising a compound of the present invention, stereoisomer thereof, veterinarily acceptable salt thereof, and a veterinarily acceptable excipient, diluent, or carrier, and (ii) a second composition comprising at least one additional veterinary agent, as described herein and a veterinarily acceptable excipient, diluent, or carrier. The veterinary compositions may be administered simultaneously or sequentially and in any order.

All of the recited WO patent publications herein are incorporated by reference.

DEFINITIONS

For purposes of the present invention, as described and claimed herein, the following terms and phrases are defined as follows:

"Additional veterinary agent(s)" as used herein, unless otherwise indicated, refers to other veterinary or pharmaceutical compounds or products that provide a therapeutically effective amount of said agent(s) that are useful for the treatment of a parasitic infection in an animal, as described herein.

"Alkoxy", as used herein, unless otherwise indicated, refers to an oxygen moiety having a further alkyl substituent. The alkyl portion (i.e., alkyl moiety) of an alkoxy group has the same definition as below. Non-limiting examples include: —OCH$_3$, —OCH$_2$CH$_3$, and the like.

"Alkyl", as used herein, unless otherwise indicated, refers to saturated monovalent hydrocarbon alkane radicals of the general formula C$_n$H$_{2n+1}$. The alkane radical may be straight or branched and may be unsubstituted or substituted. For example, the term "(C$_1$-C$_6$)alkyl" refers to a monovalent, straight or branched aliphatic group containing 1 to 6 carbon atoms. Non-exclusive examples of (C$_1$-C$_6$) alkyl groups include, but are not limited to methyl, ethyl, propyl, isopropyl, sec-butyl, t-butyl, n-propyl, n-butyl, i-butyl, s-butyl, n-pentyl, 1-methylbutyl, 2-methylbutyl, 3-methylbutyl, neopentyl, 3,3-dimethylpropyl, 2-methylpentyl, hexyl, and the like. The alkyl moiety may be attached to the chemical moiety by any one of the carbon atoms of the aliphatic chain. Alkyl groups are optionally substituted as described herein. Further when used in compound words such as alkylphenyl, said alkyl moiety has the same meaning as herein defined and may be attached to the chemical moiety by any one of the carbon atoms of the aliphatic chain. Non-limiting examples of the compound word, alkylphenyl include: C$_1$alkylphenyl is —CH$_2$phenyl, C$_2$alkylphenyl is —CH$_2$CH$_2$phenyl, C$_0$phenyl is phenyl, and the like.

"Alkenyl" as used herein, unless otherwise indicated, refers to a straight or branched aliphatic hydrocarbon chain having 2- to 6-carbon atoms and containing at least one carbon-carbon double bond (for example —C═C—, or —C═CH$_2$). Non-exclusive examples of alkenyl include: ethenyl, 1-propenyl, 2-propenyl, isopropenyl, 1-butenyl, 2-butenyl, 3-butenyl, 2-pentenyl, and the like.

"Alkynyl" as used herein, unless otherwise indicated, refers to straight or branched aliphatic hydrocarbon chain having 2- to 6-carbon atoms and containing at least one carbon-carbon triple bond (for example, —C≡C— or —C≡CH). Non-exclusive examples of alkynyl include: ethynyl, 2-propynyl, 1-methyl-2-propynyl, 2-butynyl, 3-butynyl, 2-methyl-3-butynyl, and the like.

"Animal(s)", as used herein, unless otherwise indicated, refers to an individual animal that is a mammal, bird, or fish. Specifically, mammal refers to a vertebrate animal that is human and non-human, which are members of the taxonomic class Mammalia. Non-exclusive examples of non-human mammals include companion animals (e.g., canine, feline, and equine) and livestock (e.g., bovine, swine, and ovine). Non-exclusive examples of a companion animal include: dog, cat, llama, and horse. Preferred companion animals are dog, cat, and horse. More preferred is dog. Non-exclusive examples of livestock include: swine, camel, rabbits, goat, sheep, deer, elk, bovine (cattle), and bison. Preferred livestock is cattle and swine. Specifically, bird refers to a vertebrate animal of the taxonomic class Ayes. Birds are feathered, winged, bipedal, endothermic, and egg-laying. Non-exclusive examples of bird include, poultry (e.g., chicken, turkey, duck, and geese), all of which are also referred to herein as fowl. Specifically, fish refers to the taxonomic class Chondrichthyes (cartilaginous fishes, e.g., sharks and rays) and Osteichthyes (bony fishes) which live in water, have gills or mucus-covered skin for respiration, fins, and may have scales. Non-exclusive examples of fish include shark, salmon, trout, whitefish, catfish, tilapia, sea bass, tuna, halibut, turbot, flounder, sole, striped bass, eel, yellowtail, grouper, and the like.

"Carbocyclic", as used herein, unless otherwise indicated, refers to a partially saturated or saturated 5- to 7-membered ring containing only carbon atoms and can be monocyclic or part of a fused ring or spiro ring moiety. Examples of carbocyclic rings include cyclopentane, cyclohexane, and cycloheptane. The carbocyclic ring is optionally substituted as described herein.

"Chiral", as used herein, refers to the structural characteristic of a molecule that makes it impossible to superimpose it on its mirror image, (e.g., "R" and "S" enantiomers). The term is also depicted as an asterisk (i.e.,*) in Formula 1. Subsequent chemical species that are embraced by Formula 1 are also considered to be chiral, regardless of whether the "*" is used in the species formulas of the invention. Therefore, the compounds of the instant invention, including some of the intermediates prepared during processing include both the S and R enantiomers.

"Compounds of the present invention", as used herein, unless otherwise indicated, refers to compounds of Formula (1) compounds, and stereoisomers thereof.

"Cycloalkyl", as used herein, unless otherwise indicated, includes fully saturated or partially saturated carbocyclic alkyl moieties. Non-limiting examples of partially saturated cycloalkyls include: cyclopropene, cyclobutene, cycloheptene, cyclooctene, cyclohepta-1,3-diene, and the like. Preferred cycloalkyls are 3- to 6-membered saturated monocyclic rings including cyclopropyl, cyclobutyl, cyclopentyl, and cyclohexyl. The cycloalkyl group may be attached to the chemical moiety by any one of the carbon atoms within the carbocyclic ring. Cycloalkyl groups are optionally substituted with at least one substituent. Further when used in compound words such as alkylcycloalkyl, said alkyl and cycloalkyl moiety has the same meaning as herein defined and may be attached to the chemical moiety by any one of the carbon atoms of the aliphatic chain. Examples of C$_0$-C$_6$alkylC$_3$-C$_6$cycloalkyl include, methylcyclopropane (C$_1$alkylC$_3$cycloalkyl or —CH$_2$cyclopropane), ethylcyclopropane (C$_2$alkylC$_3$cycloalkyl or —CH$_2$CH$_2$cyclopropane), methylcyclobutane (C$_1$alkylC$_4$cycloalkyl or —CH$_2$cyclobutane), ethylcyclobutane (C$_2$alkylC$_4$cycloalkyl or —CH$_2$CH$_2$cyclobutane), methylcyclohexane (C$_1$alkylC$_6$cycloalkyl or —CH$_2$cyclohexane), and the like. C$_0$alkylC$_3$-C$_6$cycloalkyl is C$_3$-C$_6$cycloalkyl. Cycloalkyl moieties are optionally substituted as described herein "Halogen" or "halo", as used herein, unless otherwise indicated, refers to fluorine, chlorine, bromine and iodine. Further, when used in compound words such as "haloalkyl", "haloalkoxy", "haloalkenyl", or "haloalkynyl", said alkyl, alkoxy, alkenyl, and alkynyl may be partially or fully substituted with halogen atoms which may be the same or different and said alkyl, alkoxy, alkenyl, and alkynyl moiety has the same meaning as above and may be attached to the chemical moiety by any one of the carbon atoms of the aliphatic chain. Examples of "haloalkyl" include F$_3$C—, ClCH$_2$—, CF$_3$CH$_2$— and CF$_3$CCl$_2$—, and the like. The term "haloalkoxy" is defined analogously to the term "haloalkyl". Examples of "haloalkoxy" include CF$_3$O—, CCl$_3$CH$_2$O—, HCF$_2$CH$_2$CH$_2$O— and CF$_3$CH$_2$O—, and the like. The term "haloalkenyl is defined analogously to the term "haloalkyl" except that the aliphatic chain contains at least one carbon-carbon double bond. Examples of "haloalkenyl" include CF$_3$CH═CH—, Cl$_3$CCH═CH—, HF$_2$CCH═CH— and F$_3$CCH═CH—, and the like. The term "haloalkynyl" is defined analogously to the term "haloalkyl" except that the aliphatic chain contains at least one carbon-carbon triple bond. Examples of "haloalkynyl" include F$_3$CC≡C—, Cl$_3$CC≡C—, HF$_2$CC≡C—, and the like.

"Heteroaryl" or "Het", as used herein, unless otherwise indicated, refers to a 5- to 6-membered aromatic monocyclic ring or an 8- to 10-membered fused aromatic ring where said monocyclic- and fused-ring moiety contains one or more heteroatoms each independently selected from N, O, or S, preferably from one to four heteroatoms. Non-exclusive examples of monocyclic heteroaryls include pyrrolyl, furanyl, thiophenyl, pyrazolyl, imidazolyl, triazolyl, tetrazolyl, thiazolyl, isoxazolyl, oxazolyl, oxadiazolyl, thiadiazolyl, pyridinyl, pyridazinyl, pyrimidinyl, pyrazinyl, and the like. Non-exclusive examples of fused heteroaryls include: benzofuranyl, benzothiophenyl, indolyl, benzimidazolyl, indazolyl, benzotriazolyl, thieno[2,3-c]pyridine, thieno[3,2-b]pyridine, benzo[1,2,5]-thiadiazole, and the like. The heteroaryl group may be attached to the chemical moiety by any one of the carbon atoms or nitrogen heteroatoms within the monocyclic or fused ring. Further when used in compound words such as alkylheteroaryl, said alkyl and heteroaryl moiety have the same meaning as herein defined and may be attached to the chemical moiety by any one of the carbon atoms of the aliphatic chain. For example, $C_0$alkylheteroaryl is heteroaryl, $C_1$alkylheteroaryl is —CH$_2$heteroaryl, $C_0$alkylheteroaryl is —CH$_2$CH$_2$heteroaryl, and the like. Heteroaryls are optionally substituted as described herein.

"Heterocycle", as used herein, unless otherwise indicated, refers to a partially saturated or saturated 3- to 7-membered monocyclic ring containing one or more heteroatoms each independently selected from N, O, or S, preferably from one to four heteroatoms. The heterocyclic ring can be part of a fused ring or spiro-ring moiety. Non-exclusive examples of heterocycle include oxirane, thiarane, aziridine, oxetane, azetidine, thiatane, tetrahydrofuran, tetrahydrothiophene, pyrrolidine, tetrahydropyrane, piperidine, piperazine, tetrahydropyridine, 2H-azirine, 2,3-dihydro-azete, 3,4-dihydro-2H-pyrrole, and the like. The heterocycle group may be attached to the chemical moiety by any one of the carbon atoms or nitrogen heteroatoms within the ring. Further when used in compound words such as alkylheterocycle, said alkyl and heterocycle moiety have the same meaning as herein defined and may be attached to the chemical moiety by any one of the carbon atoms of the aliphatic chain. For example, $C_0$alkylheterocycle is heterocycle, $C_1$alkylheterocycle is —CH$_2$heterocycle, $C_0$alkylheterocycle is —CH$_2$CH$_2$heterocycle, and the like. Heterocycles are optionally substituted as described herein.

"Optionally substituted", is used herein interchangeably with the phrase substituted or unsubstituted. Unless otherwise indicated, an optionally substituted group may have a substituent at each substitutable position of the group, and each substitution is independent of the other. An optionally substituted group also may have no substituents. Therefore, the phrase "optionally substituted with at least one substituent" means that the number of substituents may vary from zero up to a number of available positions for substitution.

"Parasite(s)", as used herein, unless otherwise indicated, refers to endoparasites and ectoparasites. Endoparasites are parasites that live within the body of its host and include helminths (e.g., trematodes, cestodes, and nematodes) and protozoa. Ectoparasites are organisms of the Arthropoda phylum (e.g., arachnids, insects, and crustaceans (e.g., copepodssea lice) which feed through or upon the skin of its host. Preferred arachnids are of the order Acarina, e.g., ticks and mites. Preferred insects are midges, fleas, mosquitos, biting flies (stable fly, horn fly, blow fly, horse fly, and the like), bed bugs, and lice. Preferred compounds of the present invention can be used for the treatment of parasites, i.e., treatment of a parasitic infection or infestation.

"Protecting group" or "Pg", as used herein, unless otherwise indicated, refers to a substituent that is commonly employed to block or protect an amine on the compound thereby protecting its functionality while allowing for the reaction of other functional groups on the compound. Non-exclusive examples of an amine-protecting group include: acyl groups (e.g., formyl, acetyl, chloroacetyl, trichloroacetyl, o-nitrophenylacetyl, o-nitrophenoxyacetyl, trifluoroacetyl, acetoacetyl, 4-chlorobutyryl, isobutyryl, o-nitrocinnamoyl, picolinoyl, acylisothiocyanate, aminocaproyl, benzoyl, and the like), acyloxy groups (e.g., 1-tert-butyloxycarbonyl (Boc), methoxycarbonyl, 9-fluorenyl-methoxycarbonyl, 2,2,2-trifluoroethoxycarbonyl, 2-trimethylsilylethxoycarbonyl, vinyloxycarbonyl, allyloxycarbonyl, 1,1-dimethyl-propynyloxycarbonyl, benzyloxy-carbonyl, p-nitrobenzyloxycarbony, 2,4-dichlorobenzyloxycarbonyl, and the like), diphenylmethane, and benzylcarbamates.

"Therapeutically effective amount", as used herein, unless otherwise indicated, refers to an amount of a compound of the present invention that (i) treat the particular parasitic infection or infestation, (ii) attenuates, ameliorates, or eliminates one or more symptoms of the particular parasitic infection or infestation, or (iii) prevents or delays the onset of one or more symptoms of the particular parasitic infection or infestation described herein.

"Treatment", "treating", and the like, as used herein, unless otherwise indicated, refers to reversing, alleviating, or inhibiting the parasitic infection, infestation, or condition. As used herein, these terms also encompass, depending on the condition of the animal, preventing the onset of a disorder or condition, or of symptoms associated with a disorder or condition, including reducing the severity of a disorder or condition or symptoms associated therewith prior to affliction with said infection or infestation. Thus, treatment can refer to administration of the compounds of the present invention to an animal that is not at the time of administration afflicted with the infection or infestation. Treating also encompasses preventing the recurrence of an infection or infestation or of symptoms associated therewith as well as references to "control" (e.g., kill, repel, expel, incapacitate, deter, eliminate, alleviate, minimize, and eradicate).

"Veterinary acceptable" as used herein, unless otherwise indicated, indicates that the substance or composition must be compatible chemically and/or toxicologically, with the other ingredients comprising a formulation, composition, and/or the animal being treated therewith. The term "pharmaceutically" acceptable has the same meaning as that recited for "veterinarily" acceptable.

DETAILED DESCRIPTION

The present invention provides Formula (1) compounds, stereoisomers thereof, as well as veterinary compositions that are useful as antiparasitic agents for animals, in particular, compounds that act as ectoparasiticides.

Compounds of the present invention may be synthesized by synthetic routes that include processes analogous to those well known in the chemical arts, particularly in light of the description contained herein. The starting materials are generally available from commercial sources such as Aldrich Chemicals (Milwaukee, Wis.) or are readily prepared using methods well known to those skilled in the art (e.g., prepared by methods generally described in Louis F. Fieser and Mary Fieser, "Reagents for Organic Synthesis", 1; 19, Wiley, New York (1967, 1999 ed.), or *Beilsteins Handbuch der organischen Chemie*, 4, Aufl. ed. Springer-Verlag, Berlin, including supplements (also available via the Beilstein online database)). For illustrative purposes, the reaction schemes depicted below demonstrate potential routes for synthesizing compounds of the present invention, and key intermediates. For a more detailed description of the individual reaction steps, see the Examples section below. A skilled artisan will appreciate that other suitable starting materials, reagents, and synthetic routes may be used to synthesize the compounds of the present invention and a variety of derivatives thereof. Further, many of the compounds prepared by the methods described below can be further modified in light of this disclosure using conventional chemistry well known to the skilled artisan.

Compounds of the present invention described herein contain at least one asymmetric or chiral center; and, therefore, exist in different stereoisomeric forms. The R and S configurations are based upon knowledge of known chiral inversion/retention chemistry. Unless specified otherwise, it is intended that all stereoisomeric forms of the compounds of the present invention as well as mixtures thereof, including racemic mixtures and diastereomeric mixtures, form part of the present invention.

Enantiomeric mixtures can be separated into their individual enantiomers on the basis of their physical chemical differences by methods well known to those skilled in the art, such as chromatography and/or fractional crystallization. A more detailed description of techniques that can be used to resolve stereoisomers of compounds from their racemic mixture can be found in Jean Jacques Andre Collet, Samuel H. Wilen, Enantiomers, Racemates and Resolutions, John Wiley and Sons, Inc. (1981).

Compounds of this invention can exist as one or more stereoisomers. The various stereoisomers include enantiomers, diastereomers and atropisomers. One skilled in the art will appreciate that one stereoisomer may be more active and/or may exhibit beneficial effects when enriched relative to the other stereoisomer(s) or when separated from the other stereoisomer(s). Additionally, the skilled artisan knows how to separate, enrich, and/or to selectively prepare said stereoisomers. The compounds of the invention may be present as a mixture of stereoisomers, individual stereo isomers or as an optically active form. For example, two possible enantiomers of Formula 1 are depicted as Formula 1a and Formula 1b involving the chiral center identified with an asterisk (*). Molecular depictions drawn herein follow standard conventions for depicting stereochemistry.

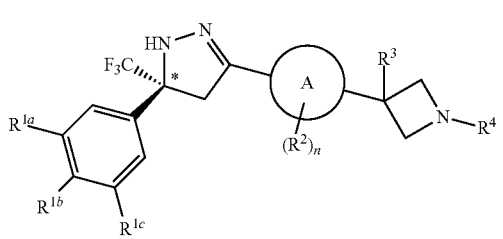

(1a)

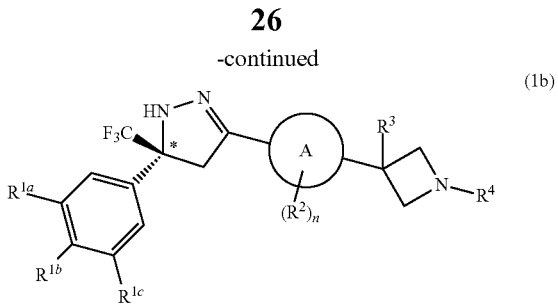

(1b)

The substituents, $R^{1a}$, $R^{1b}$, $R^{1c}$, $R^2$, $R^3$, $R^4$, and n are as described herein.

For illustrative purposes, the reaction schemes depicted below demonstrate potential routes for synthesizing key intermediates and compounds of the present invention. For a more detailed description of the individual reaction steps, see the Examples section below. Those skilled in the art will appreciate that other suitable starting materials, reagents, and synthetic routes may be used to synthesize the intermediates and compounds of the present invention and a variety of derivatives thereof. Further, many of the compounds prepared by the methods described below can be further modified in light of this disclosure using conventional chemistry. Schemes 1-13 outline the general procedures useful for the preparation and isolation of compounds of the present invention. It is to be understood, however, that the invention, as fully described herein and as recited in the claims, is not intended to be limited by the details of the following schemes or modes of preparation.

In the preparation of compounds of the present invention, protection of remote functionality of intermediates from undesired reactions can be accomplished with a protecting group. The term "protecting group" or "Pg" refers to a substituent that is commonly employed to block or protect a particular functionality while reacting other functional groups on the compound. For example, an amine-protecting group is a substituent attached to an amine that blocks or protects the amine-functionality of the compound or intermediate. Suitable amine protecting groups include: 1-tert-butyloxycarbonyl (Boc), acyl groups including: formyl, acetyl, chloroacetyl, trichloro-acetyl, o-nitrophenyl-acetyl, o-nitrophenoxyacetyl, trifluoroacetyl, acetoacetyl, 4-chlorobutyryl, isobutyryl, o-nitrocinnamoyl, picolinoyl, acylisothiocyanate, aminocaproyl, benzoyl, and the like; and acyloxy groups including: methoxycarbonyl, 9-fluorenyl-methoxycarbonyl, 2,2,2-trifluoroethoxycarbonyl, 2-trimethylsilyl-ethoxycarbonyl, vinyloxycarbonyl, allyloxycarbonyl, 1,1-dimethylpropynyloxycarbonyl, benzyloxy-carbonyl, p-nitrobenzyloxycarbony, 2,4-dichlorobenzyloxycarbonyl, and the like. Similarly, diphenylmethane and benzylcarbamates can be used as amine protecting groups. Suitable protecting groups and their respective uses are readily determined by one skilled in the art. For a general description of protecting groups and their use, see T. W. Greene, *Protective Groups in Organic Synthesis*, John Wiley & Sons, New York, 1991.

In the Schemes and Examples below, the following catalysts/reactants and miscellaneous abbreviations include: N,N-dimethyl formamide (DMF); tetrahydrofuran (THF); trifluoroacetic acid (TFA); isopropylmagnesium chloride (iPrMgCl); t-butyloxycarbonyl (BOC or Boc); triethylamine (Et₃N); equivalent (eq); dichloromethane (CH₂Cl₂); Bis(2-methoxyethylaminosulfur trifluoride (BAST); diethyaminosulfur trifluoride (DAST); carbonyldiimidazole (CDI); 4-dimethylaminopyridine (DMAP); Bis(1,5-cyclooctadiene-diiridium(1) dichloride ([Ir(COD)]₂); potassium bis(trimethylsilyl)amide (KHMDS); 1,8-diazabicycloundec-7-ene (DBU); potassium cyanide (KCN); methanol (MeOH); N-chlorosuccinimide (NCS); tris(dibenzylideneaceton)dipalladium(O) (Pd$_2$(dba)$_3$); dichloromethane (DCM); lithium chloride (LiCl); hydrochloric acid (HCl); butyl vinyl ether (BVU); triethylamine (TEA); 1-ethyl-3-(3-dimethylaminopropyl)-carbodiimide (EDC); 1-hydroxybenzotriazole (HOBt); acetonitrile (Acn or MeCN); triphenylphosphine (PPh$_3$); 1,3-Bis(diphenylphosphino)propane (DPPP); sulfur trioxide-pyridine complex (Py-SO$_3$, or SO$_3$-Py); catalyst (cat); aqueous (aq); hin layer chromatography (TLC); ethyl acetate (EtOAc); dimethyl sulfoxide (DMSO); palladium (II) acetate (Pd(OAc)$_2$); Xtalflor (Xtalflor-E and Xtalflor-M, deoxofluorination reagents); n-butyllithium (n-BuLi); deuterated chloroform (CDCl$_3$); palladium(II)[1,3-bis(diphenylphosphino)propane] (Pd-dppp); N,N-diisopropylethylamine (Hunig's base); 2,4-Bis(4-methoxyphenyl)-2,4-dithioxo-1,3,2,4-dithiadiphosphetane (Lawesson's Reagent); and di-tert-butyl dicarbonate (Boc$_2$O).

Scheme 1

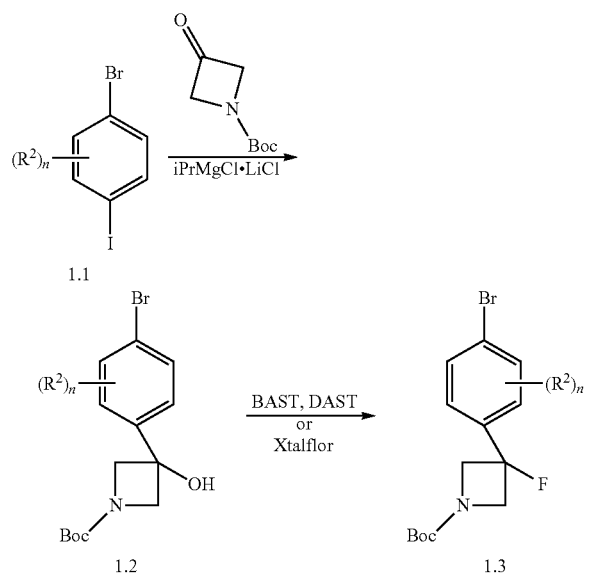

R$^2$ and n are as defined herein.

Compounds of Formula 2.2 (below) can be prepared using methods illustrated in Scheme 1. Selective Grignard metallation of the bromoiodobenzene 1.1 and addition to a protected azetidinone provides the phenylazetidine derivatives 1.2. The hydroxyl functionality can be further manipulated such as by treatment with a fluorinating agent (BAST, DAST or Xtalflor) to provide additional analogs of the phenylazetidines 1.3.

Scheme 2

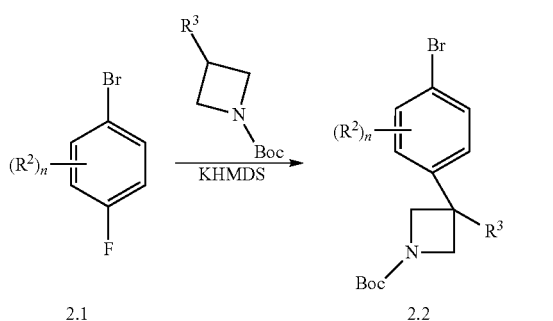

R$^2$, R$^3$, and n are as defined herein.

Alternatively, compounds of Formula 2.2 can prepared using methods illustrated in Scheme 2. When R$^3$ is an electron withdrawing group (CN, CO$_2$R, SO$_2$R, etc), deprotonation of the azetidine ring can be accomplished by treatment with potassium hexamethyldisilazane (KHMDS). This metallated species can then undergo S$_N$Ar displacement reaction of the fluorine of the bromofluorobenzene 2.1 to provide substituted azetidine analogs of Formula 2.2. Other substituted phenylazetidines can be purchased from commercial sources or prepared using procedures analogous to those found in literature (see for example: WO2012017359 or Justus Liebigs Annalen der Chemie (1961), 647, 83-91).

Scheme 3

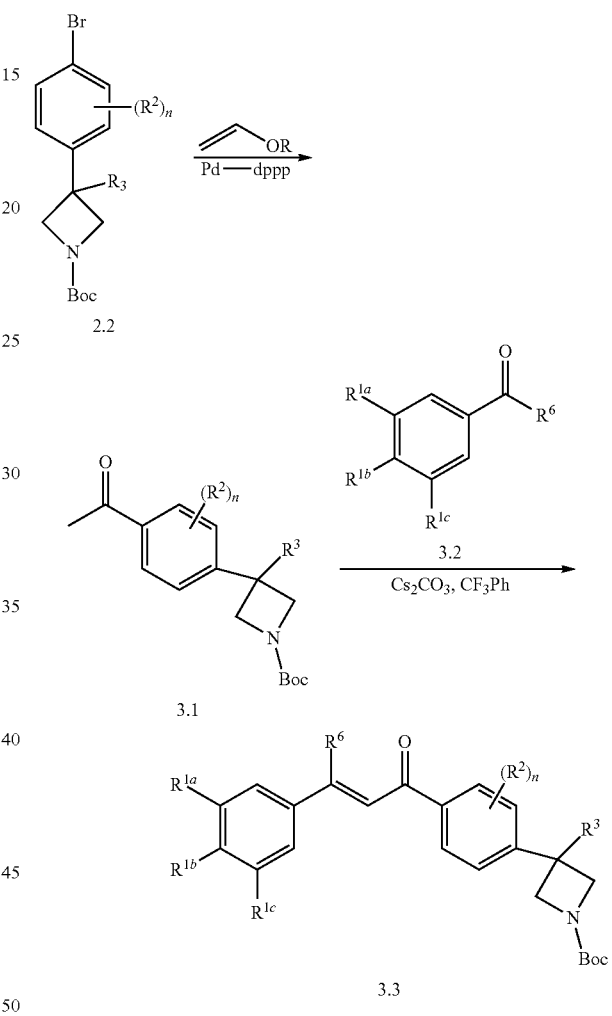

R, R$^{1a}$, R$^{1b}$, R$^{1c}$, R$^2$, R$^3$, R$^6$, and n are as defined herein.

Compounds of Formula 3.3 can be prepared using methods illustrated by Scheme 3. Palladium catalyzed condensation of the bromophenylazetidine 2.2 with a vinyl ether provides the acetophenone 3.1 which can undergo condensation with a substituted phenylketone derivative 3.2 in the presence of a base such as cesium carbonate to give the enone 3.3. The phenylketone derivative 3.2 can be prepared by reacting bromobenzene with an ethyl ester in the presence of a Grignard reagent.

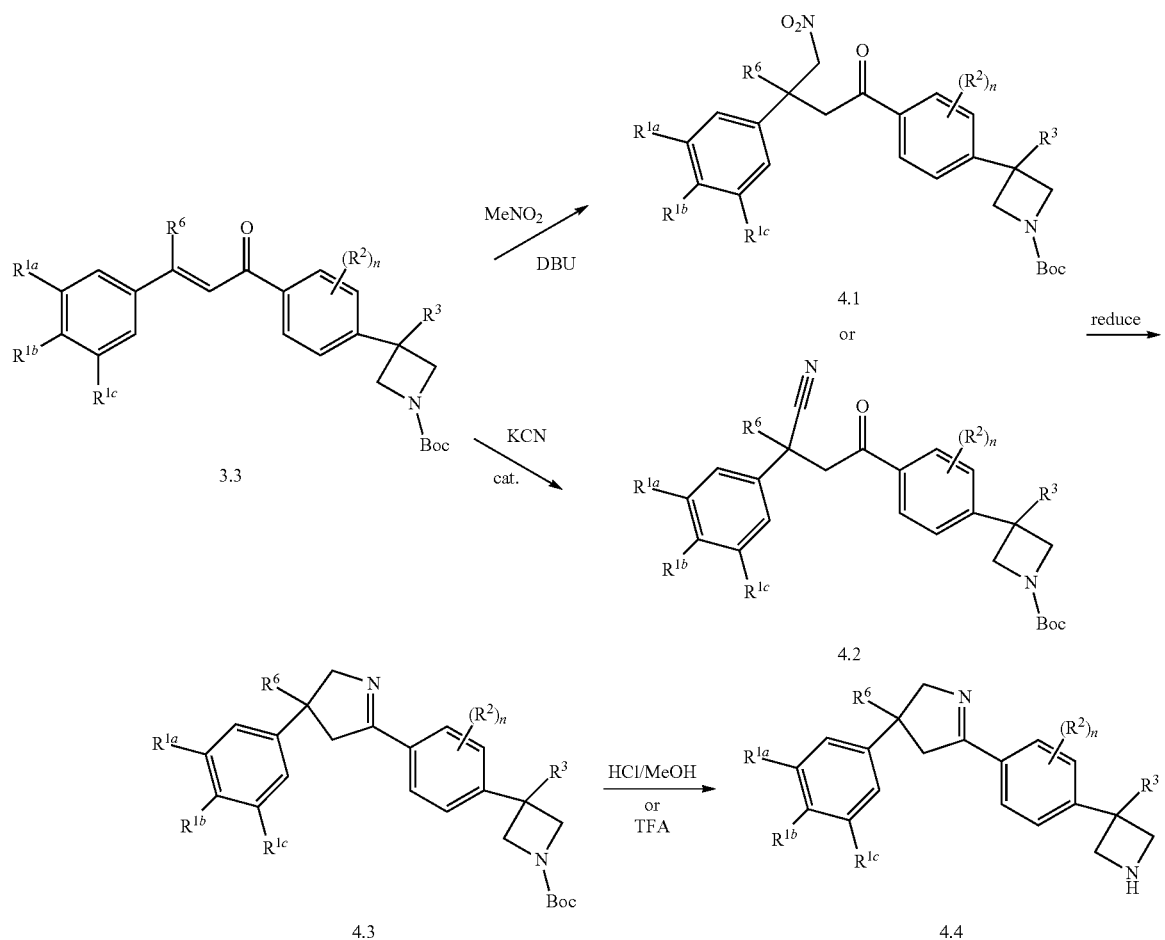

$R^{1a}$, $R^{1b}$, $R^{1c}$, $R^2$, $R^3$, $R^6$, and n are as defined herein.

Dihydropyrrole compounds of formula 4.4 can be prepared using methods illustrated by Scheme 4. The enone 3.3 can undergo Michael addition of nitromethane or cyanide to provide intermediates 4.1 or 4.2 as described in WO2011128299 or WO2011154555. Reduction to the amine followed by cyclization provides the dihydropyrroles 4.3. Reduction can be achieved under a variety of standard conditions including but not limited to: Zn/HCl, $H_2$ with a catalyst (cat.) such as Raney Nickel or palladium, borohydride or aluminum hydride reducing agents, etc. The azetidine ring can then by deprotected under acidic conditions such as HCl/MeOH or trifluoroacetic acid in $CH_2Cl_2$ to provide the dihydropyrrole phenylazetidines 4.4.

Scheme 5

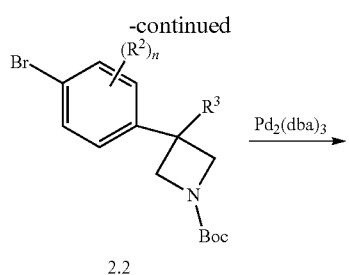

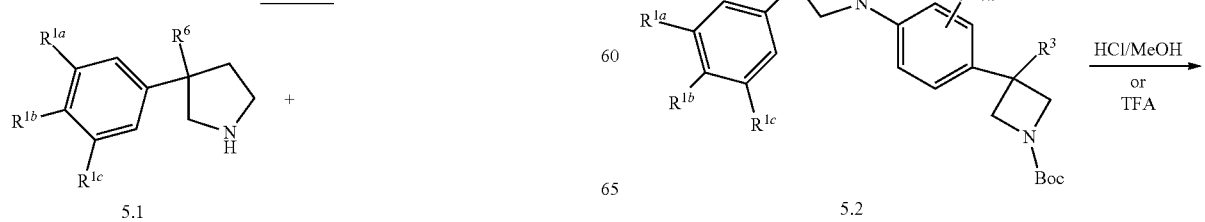

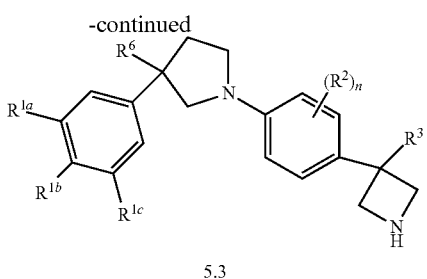
5.3

$R^{1a}$, $R^{1b}$, $R^{1c}$, $R^2$, $R^3$, $R^6$, and n are as defined herein.

Pyrrolidine compounds of formula 5.3 can be prepared using methods illustrated by Scheme 5. The quaternary phenyl pyrrolidine 5.1 can be prepared according to known chemical methods such as those described in WO2008128711. Reaction of the pyrrolidine with the bromophenylazetidine 2.2 in the presence of a palladium catalyst provides compounds of formula 5.2. Deprotection of the azetidine ring under acidic conditions such as HCl/MeOH or trifluoroacetic acid in $CH_2Cl_2$ provides the pyrrolidinyl phenylazetidines 5.3.

Scheme 6

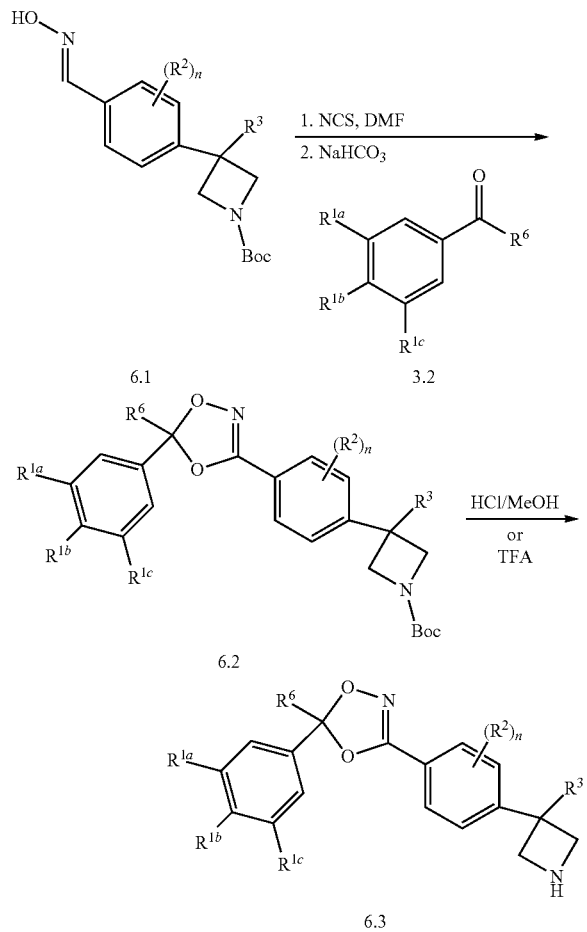

$R^{1a}$, $R^{1b}$, $R^{1c}$, $R^2$, $R^3$, $R^6$, and n are as defined herein.

Dioxazole compounds of formula 6.3 can be prepared using methods illustrated by Scheme 6. The oxime 6.1 (WO2012017359) can be converted to the dioxazole ring in a one-pot, two-step process. Treatment of the oxime with N-chlorosuccinimide provides the chlorooxime which undergoes [3+2] cyclization with aryl ketones 3.2 to provide the dioxazole 6.2. These steps can also be done as separate reactions. Removal of the Boc protecting group on the azetidine can be accomplished under acidic conditions such as HCl/MeOH or trifluoroacetic acid in $CH_2Cl_2$.

Scheme 7

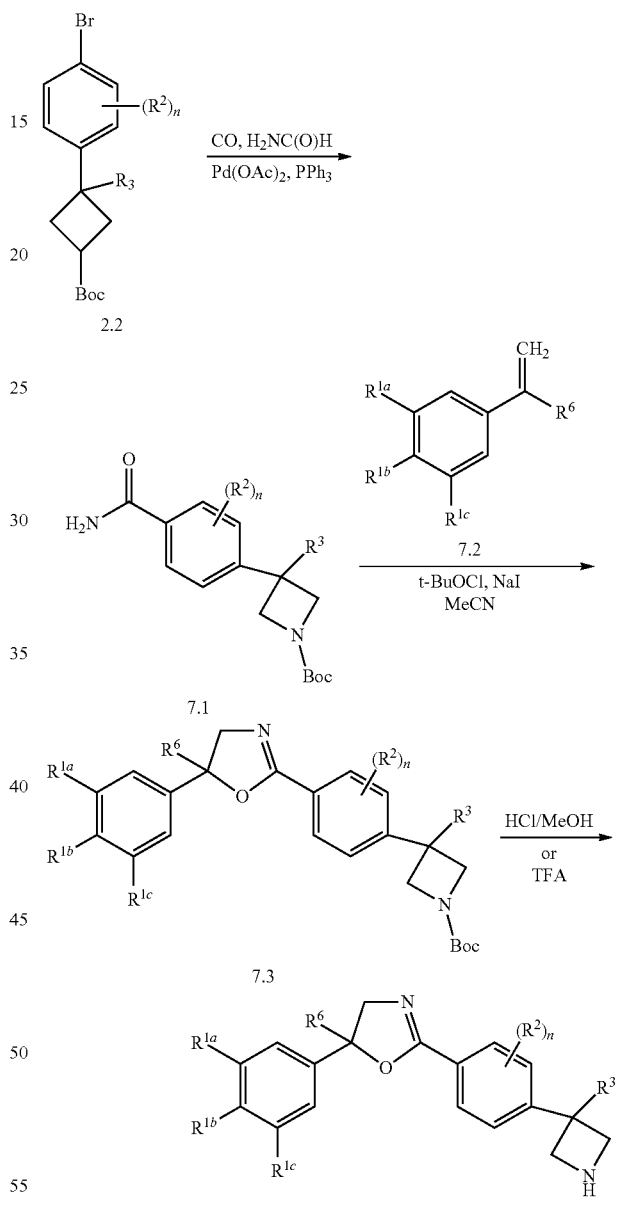

$R^{1a}$, $R^{1b}$, $R^{1c}$, $R^2$, $R^3$, $R^6$, and n areas defined herein.

Oxazoline compounds of Formula 7.4 can be prepared using methods illustrated by Scheme 7. Amidation of 2.2 by a palladium catalyzed carbonylation with carbon monoxide in the presence of an ammonia source or formamide provides the primary amide 7.1. This can undergo cycloaddition with the alkene 7.2 in the presence of tert-butyl hypoiodite as described (Chem. Comm, 2007, 3279). Removal of the Boc protecting group on the azetidine can be accomplished under acidic conditions such as HCl/MeOH or trifluoroacetic acid in CH$_2$Cl$_2$. The alkene 7.2 can be prepared according to methods described in WO2011/124998.

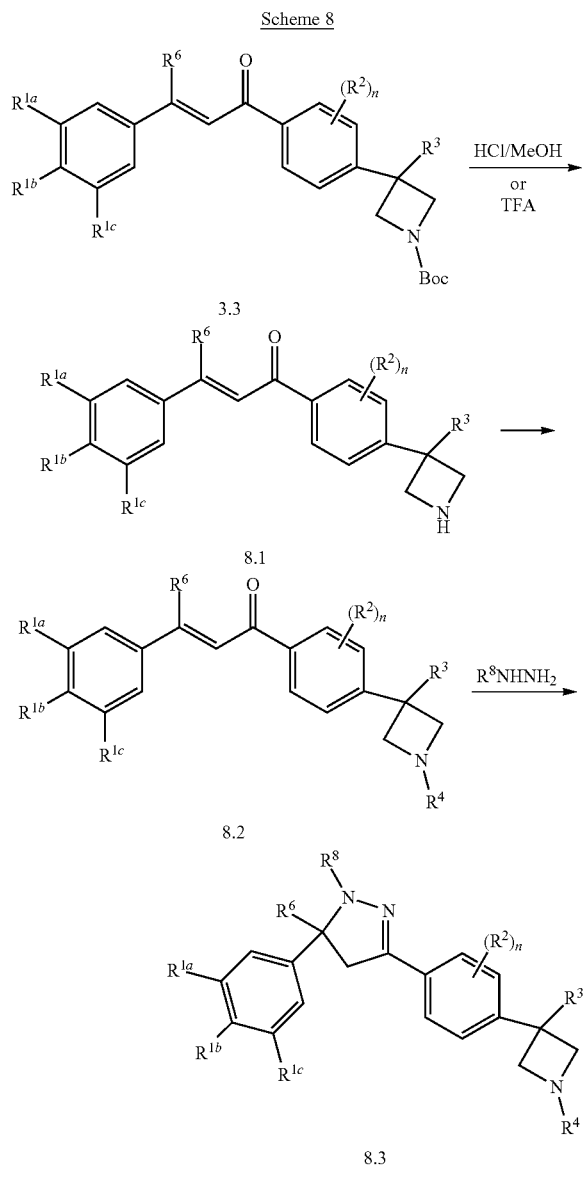

R$^{1a}$, R$^{1b}$, R$^{1c}$, R$^2$, R$^3$, R$^4$, R$^6$, R$^8$, and n are as defined herein.

Dihydropyrazole compounds of Formula 8.3 can be prepared using procedures illustrated in Scheme 8. Removal of the Boc protecting group on azetidine 3.3 can be accomplished under acidic conditions such as HCl/MeOH or trifluoroacetic acid in CH$_2$Cl$_2$. Acylation of the azetidine ring can be accomplished by reaction of the azetidine 8.1 with an acid chloride the presence of a base (e.g., Et$_3$N, pyridine, iPr$_2$NEt, and DMA) or by a condensation with a carboxylic acid utilizing a condensing agent such as HATU, CDI, EDC, or HOBt to afford amide 8.2. Sulfonamide analogs of the azetidine ring can be prepared by reaction of azetidine 8.1 with sulfonyl chlorides in the presence of triethylamine, or similar base, can give the desired sulfonamides 8.2. Compounds in which R$^4$ is alkyl or substituted alkyl can be prepared from the azetidine 8.1 by standard alkylation chemistry as shown in Scheme 11. Alternatively, alkyl analogs can be prepared by reductive amination with the corresponding aldehydes. Urea analogs can be prepared by reaction of the azetidine 8.1 with an isocyanate or preformed carbamoyl chloride in the presence of a tertiary amine base provides the ureas 8.2. Cycloaddition of enones of Formula 8.2 with hydrazines in a polar protic solvent such as ethanol or methanol provides the dihydropyrazoles 8.3. General procedures for the cycloaddition of hydrazines with enones are well documented in the chemical literature (for example, see: Tetrahedron Letters, 2004, 1489 or Bioorg. Med Chem Letters, 2006, 3175).

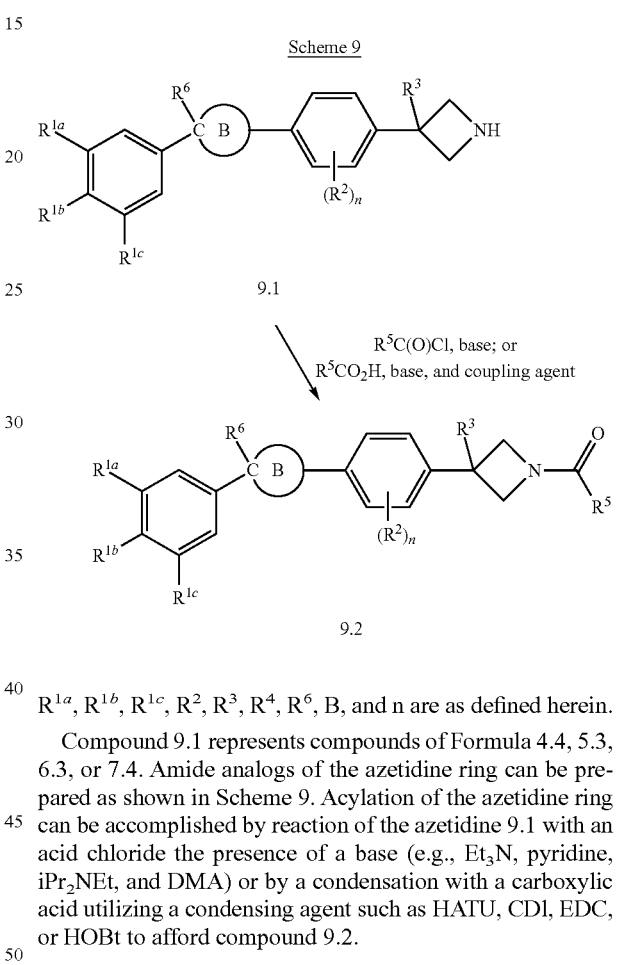

R$^{1a}$, R$^{1b}$, R$^{1c}$, R$^2$, R$^3$, R$^4$, R$^6$, B, and n are as defined herein.

Compound 9.1 represents compounds of Formula 4.4, 5.3, 6.3, or 7.4. Amide analogs of the azetidine ring can be prepared as shown in Scheme 9. Acylation of the azetidine ring can be accomplished by reaction of the azetidine 9.1 with an acid chloride the presence of a base (e.g., Et$_3$N, pyridine, iPr$_2$NEt, and DMA) or by a condensation with a carboxylic acid utilizing a condensing agent such as HATU, CDI, EDC, or HOBt to afford compound 9.2.

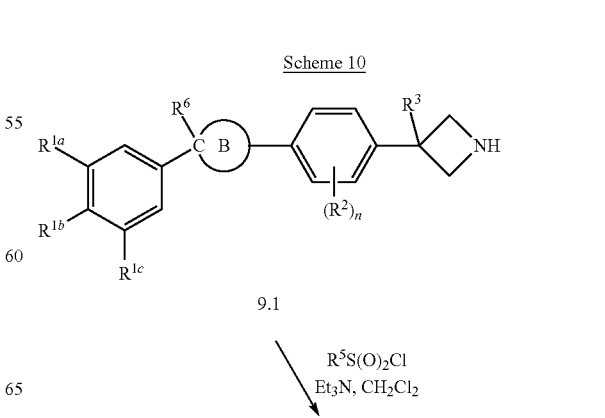

-continued

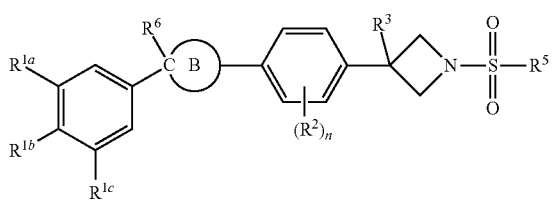

10.1

$R^{1a}$, $R^{1b}$, $R^{1c}$, $R^2$, $R^3$, $R^5$, $R^6$, B, and n are as defined herein.

Compound 9.1 represents compounds of Formula 4.4, 5.3, 6.3, or 7.4. Sulfonamide analogs of the azetidine ring can be prepared as shown in Scheme 10. Reaction of azetidine 9.1 with sulfonyl chlorides in the presence of triethylamine can give the desired sulfonamides 10.1.

Scheme 11

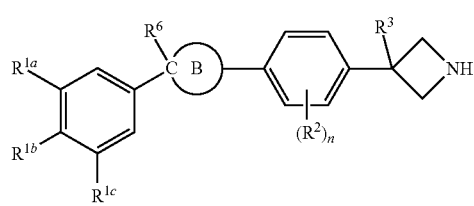

9.1

R⁴Br
K₂CO₃

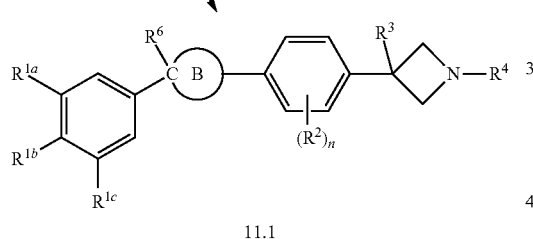

11.1

$R^{1a}$, $R^{1b}$, $R^{1c}$, $R^2$, $R^3$, $R^4$, $R^6$, B, and n are as defined herein.

Compound 9.1 represents compounds of Formula 4.4, 5.3, 6.3, or 7.4. Compounds in which $R^4$ is alkyl or substituted alkyl can be prepared from the azetidine 9.1 by standard alkylation chemistry as shown in Scheme 11. Alternatively, alkyl analogs can be prepared by reductive amination with the corresponding aldehydes.

Scheme 12

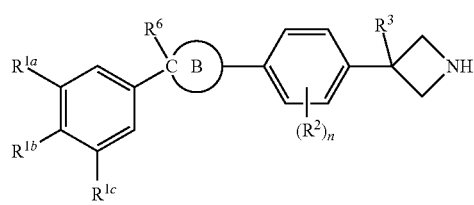

9.1

R⁵NC, Et₃N, CH₂Cl₂; or
C(O)Cl₂, NRᵃR⁵, Et₃N, DMAP, CH₂Cl₂; or
CDI, NRᵃR⁵, Et₃N, CH₂Cl₂

-continued

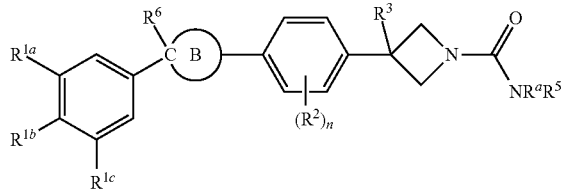

12.1

$R^{1a}$, $R^{1b}$, $R^{1c}$, $R^2$, $R^3$, $R^a$, $R^5$, $R^6$, and n are as defined herein.

Compound 9.1 represents compounds of Formula 4.4, 5.3, 6.3, or 7.4. Urea analogs can be prepared as shown in Scheme 12. Reaction of the azetidine 9.1 with an isocyanate or preformed carbamoyl chloride in the presence of a tertiary amine base provides the ureas 12.1.

Scheme 13

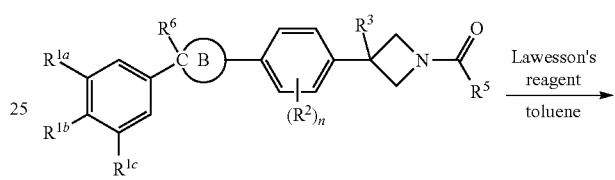

9.2

Lawesson's reagent
toluene

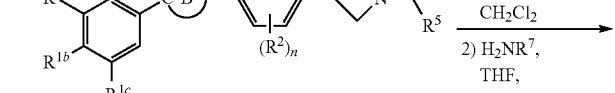

13.1

1) methyl triflate, CH₂Cl₂
2) H₂NR⁷, THF, Hunig's Base

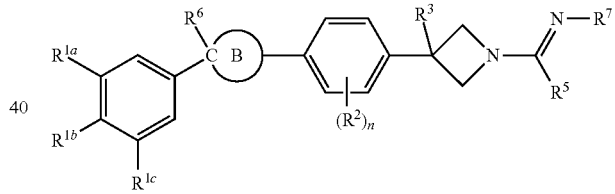

13.2

$R^{1a}$, $R^{1b}$, $R^{1c}$, $R^2$, $R^3$, $R^5$, $R^6$, $R^7$, B, and n are as defined herein.

Thioamide 13.1 can be prepared by treatment of amide 9.2 with Lawesson's reagent in refluxing toluene. Methyl triflate can be added to thioamide 13.1 in a solvent such as CH₂Cl₂ to form a thioimidate intermediate. A substituted amine (e.g., H₂NCN, H₂NS(O)ₚR, H₂NR, H₂NOH, and the like) and Hunig's base in THF can be subsequently added directly to the thioimidate solution to afford the amidine 13.2.

One skilled in the art will recognize that, in some cases, after the introduction of a given reagent as it is depicted in the schemes, it may be necessary to perform additional routine synthetic steps not described in detail to complete the synthesis of Formula (1) compounds.

The present invention includes all veterinarily acceptable isotopically-labelled Formula (1) compounds wherein one or more atoms are replaced by atoms having the same atomic number, but an atomic mass or mass number different from the atomic mass or mass number usually found in nature.

Examples of isotopes suitable for inclusion in the compounds of the present invention include isotopes of hydrogen, such as $^2$H and $^3$H, carbon, such as $^{11}$C, $^{13}$C and $^{14}$C, chlorine, such as $^{36}$Cl, fluorine, such as $^{18}$F, iodine, such as $^{123}$I and $^{125}$I, nitrogen, such as $^{13}$N and $^{15}$N, oxygen, such as $^{15}$O, $^{17}$O and $^{18}$O, and sulphur, such as $^{35}$S.

The skilled person will appreciate that the compounds of the present invention could be made by methods other than those herein described as incorporated herein by reference, by adaptation of the methods herein described and/or adaptation of methods known in the art, for example the art described herein, or using standard textbooks such as "Comprehensive Organic Transformations—A Guide to Functional Group Transformations", R C Larock, Wiley-VCH (1999 or later editions).

The Formula (1) compounds are useful as ectoparasitic and endoparasitic agents, therefore, another embodiment of the present invention is a veterinary or pharmaceutical composition comprising a therapeutically effective amount of a Formula (1) compound, stereoisomer thereof, and a veterinarily or pharmaceutically acceptable excipient, diluent or carrier. The compounds of the present invention (including the compositions and processes used therein) may also be used in the manufacture of a medicament for the therapeutic applications described herein.

A typical formulation is prepared by mixing a Formula (1) compound with a carrier, diluent or excipient. Suitable carriers, diluents and excipients are well known to those skilled in the art and include materials such as carbohydrates, waxes, water soluble and/or swellable polymers, hydrophilic or hydrophobic materials, gelatin, oils, solvents, water, and the like. The particular carrier, diluent or excipient used will depend upon the means and purpose for which the compound of the present invention is being applied. Solvents are generally selected based on solvents recognized by persons skilled in the art as safe to be administered to an animal. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a compound of the present invention or veterinary composition thereof) or aid in the manufacturing of the veterinary or pharmaceutical product (i.e., medicament).

The formulations can be prepared using conventional dissolution and mixing procedures. Such compositions and methods for their preparation may be found, for example, in 'Remington's Veterinary Sciences', 19th Edition (Mack Publishing Company, 1995; and "Veterinary Dosage Forms: Tablets, Vol. 1", by H. Lieberman and L. Lachman, Marcel Dekker, N.Y., 1980 (ISBN 0-8247-6918-X). For example, the bulk drug substance (i.e., compound of the present invention or stabilized form of the compound (e.g., complex with a cyclodextrin derivative or other known complexation agent)) is dissolved in a suitable solvent in the presence of one or more other excipients. The compounds of the present invention are typically formulated into veterinary or pharmaceutical dosage forms to provide an easily controllable dosage form for administration. Compounds of the present invention can also be admixed with animal feed.

The compounds may be administered alone or in a formulation appropriate to the specific use envisaged, the particular species of host animal being treated and the parasite involved. Generally, they will be administered as a formulation in association with one or more veterinarily or pharmaceutically acceptable salts, excipients, diluents, or carriers. The term "excipient", "diluent" or "carrier" is used herein to describe any ingredient other than the Formula (1) compounds or any additional antiparasitic agent. The choice of excipient, diluent, or carrier will to a large extent depend on factors such as the particular mode of administration, the effect of the excipient, carrier, or diluent on solubility and stability, nature of the dosage form, and animal specie.

The methods by which the compounds of the present invention may be administered include oral, topical, and injectable (subcutaneous, intraperitoneal, and intramuscular) administration. The preferred method of administration of the Formula (1) compounds is in an oral solid dosage form or oral liquid dosage form. Equally preferred is topical administration.

The Formula (1) compounds can be administered orally by capsule, bolus, tablet, powders, lozenges, chews, multi and nanoparticulates, gels, solid solution, films, sprays, liquid form, or admixed with food. Oral administration is the preferred method of administration and as such it is desirable to develop active Formula (1) compounds that are particularly suited to such formulations. Such formulations may be employed as fillers in soft or hard capsules, tablets, or chews, and typically comprise a carrier, for example, water, ethanol, polyethylene glycol, N-methylpyrrolidone, propylene glycol, methylcellulose, or a suitable oil, and one or more emulsifying agents and/or suspending agents. Liquid forms include suspensions, solutions, syrups, drenches and elixirs. Liquid formulations may also be prepared by the reconstitution of a solid, for example, from a sachet. Oral drenches are commonly prepared by dissolving or suspending the active ingredient in a suitable medium. Feed admixtures can be prepared for livestock and fish. Oral formulations can comprise from about 0.5 mg/kg to 50 mg/kg of a Formula (1) compound, and preferably about 0.1 mg/kg to 30 mg/kg of a Formula (1) compound. Depending upon the host specie treated and the parasite being treated, dose adjustments can be made.

The compounds may be administered topically to the skin or mucosa, that is dermally or transdermally. This is a preferred method of administration and as such it is desirable to develop active Formula (1) compounds that are particularly suited to such formulations, for example liquid forms. Typical formulations for this purpose include pour-on, spot-on, multi-spot-on, stripe-on, comb-on, roll-on, dip, spray, mousse, shampoo, powder formulation, gels, hydrogels, lotions, solutions, creams, ointments, dusting powders, dressings, foams, films, skin patches, wafers, implants, sponges, fibers, bandages and micro emulsions. Liposomes may also be used. Typical carriers include alcohol, water, mineral oil, liquid petrolatum, white petrolatum, glycerin, N-methyl formamide, glycol monomethyl ethers, polyethylene glycol, propylene glycol, and the like. Penetration enhancers may be incorporated—see, for example, J Pharm Sci, 88 (10), 955-958 by Finnin and Morgan (October 1999). Pour-on or spot-on formulations may be prepared by dissolving the active ingredients in an acceptable liquid carrier vehicle such as butyl digol, liquid paraffin or a non-volatile ester, optionally with the addition of a volatile component such as propan-2-ol or a glycol ether. Alternatively, pour-on, spot-on or spray formulations can be prepared by encapsulation, to leave a residue of active agent on the surface of the animal, this effect may ensure that the Formula (1) compounds have increased persistence of action and are more durable, for example they may be more water fast. Topical formulations of the combination contemplated herein can comprise from about 0.5 mg/kg to 50 mg/kg of a Formula (1) compound, and preferably about 1 mg/kg to 10 mg/kg of a Formula (1) compound. The compositions suitable for spot-on application according to the invention can be prepared by conventional mixing means. The volume of the applied composition can be from about 0.5 mL/kg to 5 mL/kg and preferably from about 1 mL/kg to 3 mL/kg. Similarly, dose can be adjusted.

The compounds of the present invention can also be administered topically via a support matrix for example, a synthetic or natural resin, plastic, cloth, leather, or other such polymeric system in the shape of a collar or ear tag. Said collar or ear tag may be coated, impregnated, layered, by any means so as to provide a veterinarily or pharmaceutically acceptable amount of a compound of the present invention alone, or with a veterinarily or pharmaceutically acceptable excipient, diluent, or carrier, and optionally an additional veterinary agent, or veterinarily or pharmaceutically acceptable salt thereof.

Agents may be added to the formulations of the present invention to improve the persistence of such formulations on the surface of the animal to which they are applied, for example to improve their persistence on the coat of the animal. It is particularly preferred to include such agents in a formulation which is to be applied as a pour-on or spot-on formulation. Examples of such agents include acrylic copolymers and in particular fluorinated acrylic copolymers. A particular suitable reagent is the trademark reagent "Foraperle" (Redline Products Inc, Texas, USA). Certain topical formulations may include unpalatable additives to minimize oral exposure.

Injectable formulations may be prepared in the form of a sterile solution, which may contain other substances, for example enough salts or glucose to make the solution isotonic with blood. Acceptable liquid carriers include vegetable oils such as sesame oil, glycerides such as triacetin, esters such as benzyl benzoate, isopropyl myristate and fatty acid derivatives of propylene glycol, as well as organic solvents such as pyrrolidin-2-one and glycerol formal. The formulations are prepared by dissolving or suspending compounds of the present invention alone or with an additional veterinary agent in the liquid carrier such that the final formulation contains from about 0.01 to 50% by weight of the active ingredients, preferably from about 0.01% to about 10% by weight of the active ingredients.

Suitable devices for injection include needle (including micro needle) injectors, needle-free injectors and infusion techniques. Subcutaneous formulations are typically aqueous solutions which may contain excipients such as salts, carbohydrates and buffering agents (preferably to a pH of from 3 to 9), but, for some applications, they may be more suitably formulated as a sterile non-aqueous solution or as a dry powder form to be used in conjunction with a suitable vehicle such as sterile, pyrogen-free water. The preparation of subcutaneous formulations under sterile conditions, for example, by lyophilisation, may readily be accomplished using standard veterinary techniques well known to those skilled in the art. The solubility of compounds of Formula (1) used in the preparation of subcutaneous solutions may be increased by the use of appropriate formulation techniques, such as the incorporation of solubility-enhancing agents.

Such formulations are prepared in a conventional manner in accordance with standard medicinal or veterinary practice. Further, these formulations will vary with regard to the weight of active compound contained therein, depending on the species of host animal to be treated, the severity and type of infection or infestation, and the body weight of the animal.

For fish, compounds of the present invention can be formulated for oral administration by way of feed admixture. For example, the compounds of the present invention can be formulated in a food product (e.g., pellets) that can be easily dispersed to fish as a feeding agent. Further, a compound of the present invention can be administered topically by immersing the fish into an aqueous environment containing at least one of the compounds of the present invention. For example, fish may be transferred into a tank for treatment or caused to pass from one holding zone into another. The compounds of the present invention may also be administered directly to the water containing the fish. The compound of the present invention can be in any dispersible formulation such that upon introduction to water the compound dissolves into the solution. Alternatively, the compounds of the present invention can be administered by injection. Preferable injection routes for treatment of fish are intraparitoneal or intramuscular. The injectable formulations include any liquid suspension, such as oils, aqueous solutions, or oil and water emersions. The compounds of the present invention can also be co-administered with additional agents, antigens, adjuvants, carriers, diluents or nutrients.

The Formula (1) compounds are also active against all or individual developmental stages of animal pests showing normal sensitivity, as well as those showing resistance to widely used parasiticides.

As described herein, compounds of the present invention may be administered alone or in combination with at least one additional veterinary agent including insecticides, acaricides, anthelmintics, fungicides, nematocides, antiprotozoals, bactericides, and growth regulators to form a multi-component agent giving an even broader spectrum of veterinary utility. Thus, the present invention also pertains to a composition comprising an effective amount of a Formula (1) compound, a stereoisomer thereof, and an effective amount of at least one additional veterinary agent and can further comprise one or more of a veterinarily or pharmaceutically acceptable excipient, diluent, or carrier.

The following list of additional veterinary agents together with which the compounds of the present invention can be used is intended to illustrate the possible combinations, but not to impose any limitation. Non-limiting examples of additional veterinary agents include: amitraz, arylpyrazoles as recited in publications WO1998/24767 and WO2005/060749, amino acetonitriles, anthelmintics (e.g., albendazole, cambendazole, fenbendazole, flubendazole, mebendazole, octadepsipeptides, oxfendazole, oxibendazole, paraherquamide (2-desoxoparaherquamide, derquantel), parbendazole, piperazines, praziquantel, thiabendazole, tetramisole, triclabendazole, levamisole, pyrantel pamoate, oxantel, morantel, and the like), indoxacarb and derivatives thereof, avermectins (e.g., abamectin, doramectin, emamectin, eprinomectin, ivermectin, moxidectin, selamectin, and the like), milbemycin, milbemycin oxime, DEET, demiditraz, diethylcarbamazine, fipronil, insect growth regulators (e.g., hydroprene, kinoprene, methoprene, pyriproxyfen, and the like), metaflumizone, niclosamide, permethrin, pyrethrins, spinosad, and formamidines (e.g., demiditraz, amitraz, and the like), and mixtures thereof. In certain instances, combinations of a Formula (1) compound with an additional veterinary agent(s) can result in a greater-than-additive effect. Reducing the quantity of active ingredients released in the environment while ensuring effective pest control is always desirable.

It may be desirable to administer a compound of the present invention, stereoisomers thereof, alone or in a composition comprising a veterinarily acceptable excipient, diluent, or carrier, for example, for the purpose of treating a particular parasitic infection or infestation or condition associated therewith. It is within the scope of the present invention that two or more veterinary compositions, at least one of which contains a Formula (1) compound in accordance with the invention, and the other, an additional veterinary agent, may conveniently be combined in the form of a kit suitable for coadministration of the compositions.

The compounds of the present invention (including the compositions and processes used therein) may also be used in the manufacture of a medicament for the therapeutic applications described herein.

The compounds of the present invention, stereoisomers thereof, and compositions comprising a therapeutically effective amount of a Formula (1) compound and a veterinarily acceptable excipient, diluent, or carrier are useful as parasiticides (endo- and ecto-parasites) for the control and treatment of infections or infestations manifested by said parasite in an animal. The compounds of the present invention have utility as an ectoparasiticide, in particular, as an acaricide and insecticide. The compounds of the present invention also have utility as an endparasiticide. They may, in particular, be used in the fields of veterinary medicine, livestock husbandry, fish farming, and the maintenance of public health: against acarids, insects, and endoparasites which are parasitic upon vertebrates, particularly warm-blooded vertebrates, including companion animals, livestock, fish, and birds.

Some non-limiting examples of ectoparasites include: ticks (e.g., *Ixodes* spp., (e.g., *I. scapularis, I. ricinus, I. hexagonus, I. holocyclus*), *Rhipicephalus* spp., (e.g., *R. sanguineus*), *Boophilus* spp., *Amblyomma* spp. (e.g., *A. maculatum, A. triste, A. parvum, A. ovale, A. oblongoguttatum, A. aureolatum, A. cajennense, A. americanum*), *Hyalomma* spp., *Haemaphysalis* spp., *Dermacentor* spp. (e.g., *D. variabilis, D. andersoni, D. reticulatus, D. marginatus*), *Ornithodorus* spp., and the like); mites (e.g., *Dermanyssus* spp., *Cheyletiella* spp., *Sarcoptes* spp., (e.g., *S. scabiei*), *Psoroptes* spp., (e.g., *P. bovis*), *Otodectes* spp., *Chorioptes* spp., *Demodex* spp., (e.g., *D. folliculorum, D. canis*, and *D. brevis*) and the like); chewing and sucking lice (e.g., *Damalinia* spp., *Linognathus* spp., *Haematopinus* spp., *Solenoptes* spp., *Trichodectes* spp., *Felicola* spp., and the like); fleas (e.g., *Ctenocephalides* spp., and the like); biting flies, midges, and mosquitos (e.g., *Tabanus* spp., *Haematobia* spp., *Musca* spp., *Stomoxys* spp., *Cochliomyia* spp., *Simuliidae* spp., *Ceratopogonidae* spp., *Psychodidae* spp., *Aedes* spp., *Culex* spp., *Anopheles* spp., and the like); bed bugs (e.g., insects within the genus *Cimex* and family Cimicidae); grubs (e.g., *Dermatobia* spp., *Hypoderma bovis, H. lineatum*); and copepods (e.g., sea lice within the Order Siphonostomatoida, including genera *Lepeophtheirus* and *Caligus*).

Compounds of the invention can also be used for the treatment of endoparasites, for example, cestodes (tapeworms), nematodes (round worms), and trematodes (flukes). Non-exlusive examples of the nematodes include roundworms, hookworms, whipworms, and heart worms. Non-exclusive examples of the gastrointestinal roundworms include: *Ostertagia ostertagi* (including inhibited larvae), *O. lyrata, Haemonchus placei, H. similis, H. contortus, Toxascaris leonine, Toxocara canis, T. cati, Trichostrongylus axei, T. colubriformis, T. longispicularis, Cooperia oncophora, C. pectinata, C. punctata, C. surnabada* (syn. *mcmasteri*), *C. spatula, Ascaris suum, Hyostrongylus rubidus, Bunostomum phlebotomum, Capillaria bovis, B. trigonocephalum, Strongyloides papillosus, S. ransomi, Oesophagostomum radiatum, O. dentatus, O. columbianum, O. quadrispinulatum, Trichuris* spp., and the like. Non-exclusive examples of hookworm (e.g., *Ancylostoma caninum, A. tubaeforme, A. braziliense, Uncinaria stenocephala*, and the like); lungworm (e.g., *Dictyocaulus viviparus* and *Metastrongylus* spp); eyeworm (e.g., *Thelazia* spp.); parasitic stage grubs (e.g., *Hypoderma bovis, H. lineatum, Dermatobia hominis*); kidneyworms (e.g., *Stephanurus dentatus*); screw worm (e.g., *Cochliomyia hominivorax* (larvae); filarial nematodes of the super-family Filarioidea and the Onchocercidae Family. Non-limiting examples of filarial nematodes within the Onchocercidae Family include the genus *Brugia* spp. (i.e., *B. malayi, B. pahangi, B. timori*, and the like), *Wuchereria* spp. (i.e., *W. bancrofti*, and the like), *Dirofilaria* spp. (*D. immitis, D. ursi, D. tenuis, D. spectans, D. lutrae*, and the like), *Dipetalonema* spp. (i.e., *D. reconditum, D. repens*, and the like), *Onchocerca* spp. (i.e., *O. gibsoni, O. gutturosa, O. volvulus*, and the like), *Elaeophora* spp. (*E. bohmi, E. elaphi, E. poeli, E. sagitta, E. schneideri*, and the like), *Mansonella* spp. (i.e., *M. ozzardi, M. perstans*, and the like), and *Loa* spp. (i.e., *L. loa*). Non-exclusive examples of cestodes include: *Taenia saginata, T. solium, T. taeniaformis, Hymenolepsis nana, H. diminuta, Dipylidium caninum; Diphyllobothrium latum; Echinococcus* spp., *Mesocestoides* spp., and *Spirometra* spp. Non-exclusive examples of trematodes include: *Paragonimus kellicotti, Alaria* spp., *Nanophyetus salmincola, Heterobiharzia Americana, Platynosomum fastosum, Schistosoma* spp., and *Fasciola* spp.

The compounds of the present invention and compositions comprising compounds of the present invention in conjunction with at least one other veterinary agent are of particular value in the control of ectoparasites, endoparasites, and insects which are injurious to, or spread or act as vectors of diseases in animals. The ectoparasites, insects, and endoparasites which can be treated with a combination of a Formula (1) compound and an additional veterinary agent include those as herein before described and including helminthes of the phylum platyhelminthes (e.g., trematodes, eucestoda, and cestoda), and nathelminthes (e.g., nematodes).

Any of the compounds of the present invention, or a suitable combination of a compound of the present invention and optionally, with at least one additional veterinary agent may be administered directly to the animal and/or indirectly by applying it to the local environment in which the animal dwells. Direct administration includes contacting the skin, fur, or feathers of a subject animal or bird with the compound(s), or by feeding or injecting the compounds into the animal or bird.

The Formula (1) compounds, stereoisomers thereof, and combinations with at least one additional veterinary agent, as described herein, are of value for the treatment and control of the various lifecycle stages of insects and parasites including egg, nymph, larvae, juvenile and adult stages.

The present invention also relates to a method of administering a compound of the present invention alone or in combination with at least one additional veterinary agent, and optionally a veterinarily or pharmaceutically acceptable excipient, diluent, or carrier, to animals in good health comprising the application to said animal to reduce or eliminate the potential for human parasitic infection or infestation from parasites carried by the animal and to improve the environment in which the animal and human inhabit.

The reactions set forth below were done generally under a positive pressure of argon or nitrogen or with a drying tube, at ambient temperature (unless otherwise stated), in anhydrous solvents, and the reaction flasks were fitted with rubber septa for the introduction of substrates and reagents via syringe. Glassware was oven dried and/or heat dried. Analytical thin layer chromatography (TLC) was performed using glass-backed silica gel 60 F 254 precoated plates and eluted with appropriate solvent ratios (v/v). Reactions were assayed by TLC or LCMS and terminated as judged by the consumption of starting material. Visualization of the TLC plates was done with UV light (254 nM wavelength) or with an appropriate TLC visualizing solvent and activated with heat. Flash column chromatography (Still et al., *J. Org. Chem.* 43, 2923, (1978) was performed using silica gel (RediSep Rf) or various MPLC systems, such as Biotage or ISCO purification system.

Conventional methods and/or techniques of separation and purification known to one of ordinary skill in the art can be used to isolate the compounds of the present invention, as well as the various intermediates related thereto. Such techniques will be well-known to one of ordinary skill in the art and may include, for example, all types of chromatography (high pressure liquid chromatography (HPLC), column chromatography using common adsorbents such as silica gel, and thin-layer chromatography (TLC), recrystallization, and differential (i.e., liquid-liquid) extraction techniques.

The compound structures in the examples below were confirmed by one or more of the following methods: proton magnetic resonance spectroscopy, and mass spectroscopy. Proton magnetic resonance ($^1$H NMR) spectra were determined using a Bruker spectrometer operating at a field strength of 400 megahertz (MHz). Chemical shifts are reported in parts per million (PPM, δ) downfield from an internal tetramethylsilane standard. Mass spectra (MS) data were obtained using Agilent mass spectrometer with atmospheric pressure chemical ionization. Method: Acquity HPLC with chromatography performed on a Waters BEH C18 column (2.1×50 mm, 1.7 μm) at 50° C. The mobile phase was a binary gradient of acetonitrile (containing 0.1% trifluoroacetic acid) and water (5-100%).

Embodiments of the present invention are illustrated by the following Examples. It is to be understood, however, that the embodiments of the invention are not limited to the specific details of these Examples, as other variations thereof will be known, or apparent in light of the instant disclosure, to one of ordinary skill in the art.

EXAMPLES

One skilled in the art will also recognize that Formula (1) compounds and the intermediates described herein can be subjected to various electrophilic, nucleophilic, radical, organometallic, oxidation, and reduction reactions to add substituents or modify existing substituents.

The following intermediates and examples were prepared according to the schemes and procedures presented herein. It is to be understood, however, that the invention, as fully described herein and as recited in the claims, is not intended to be limited by the details of the following schemes or modes of preparation.

Preparation of Phenyl Azetidine Intermediates

Preparation 1a: tert-butyl-3-hydroxyazetidine-1-carboxylate; (3-hydroxyazetidine-1-carboxylic acid tert-butyl ester)

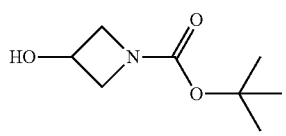

To a stirred cold (0° C.) solution of 3-hydroxyazetidine hydrochloride (75 g, 0.68 mol) in ethanol (1300 mL) was added triethylamine (208 g/280 mL, 2.05 mol) followed by Boc$_2$O (164 g, 0.75 mol). The resultant solution was stirred at ambient temperature for 16 hours. GC/MS analysis of the reaction mixture revealed complete reaction. Volatiles were removed in vacuo and the residue was diluted with EtOAc (1300 mL) and washed with 10% citric acid (700 mL), water (700 mL) and brine (700 mL). The organics were dried over sodium sulfate filtered, and concentrated to give the desired product (100.8 g, 85% yield). $^1$H NMR (CDCl$_3$) δ 4.6 (m, 1H), 4.2 (m, 2H), 3.8 (m, 2H), 1.4 (s, 9H).

Preparation 2a: tert-butyl 3-oxoazetidine-1-carboxylate; (3-oxoazetidine-1-carboxylic acid tert-butyl ester)

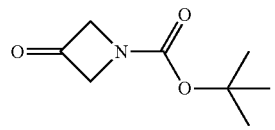

A 5 L-3-neck flask equipped with mechanical stirrer, thermocouple, addition funnel and nitrogen inlet was charged with Py-SO$_3$ (277 g, 1.74 mol) and DMSO (900 mL) and cooled to 10° C. in ice-bath. TEA (177 g/244 mL, 1.74 mol) was added. A solution of tert-butyl-3 hydroxyazetidine-1-carboxylate (Preparation 1a, 100.8 g, 0.58 mol) in DMSO (500 mL) was added slowly via addition funnel at 10° C. The reaction was stirred at ambient temperature overnight. GC/MS analysis of the reaction mixture reveals that the reaction was completed. The reaction was quenched with brine (1 L). Solids were filtered and the aqueous was extracted with ethyl acetate (3×1 L). The combined organics were washed with saturated aqueous NaHCO3 (1.5 L), brine (1.5 L), dried over sodium sulfate, filtered, and concentrated to give the desired product (94 g, 95% yield). $^1$H NMR (CDCl$_3$) δ 4.6 (s, 4H), 1.4 (s, 9H).

Preparation 3a: tert-butyl 3-hydroxy-3-(4-(trimethylsilyl)phenylazetidine-1-carboxylate; (3-hydroxy-3-(4-trimiethylsilyl)phenyl-azetidine-1-carboxylic acid tert-butyl ester)

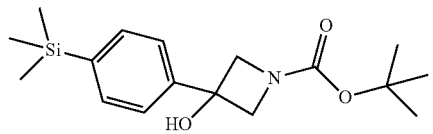 [SMILES: CC(C)(C)OC(=O)N1CC(O)(c2ccc([Si](C)(C)C)cc2)C1]

A 2 L-3neck flask equipped with mechanical stirrer, thermocouple, addition funnel and nitrogen inlet was charged with (4-bromophenyl)trimethylsilane (80.4 g, 0.35 mol), THF (600 mL), Mg (8.5 g), and I$_2$ (catalytic amount). The suspension was refluxed at 68° C. for 1.5 hours until all magnesium disappeared. The solution was cooled to 0° C. in an ice-bath. Then, a solution of tert-butyl 3-oxoazetidine-1-carboxylate (Preparation 2a, 30 g, 0.17 mol) in THF (200 mL) was added slowly via addition funnel. The solution was stirred at 0° C. for 3 hours. LC/MS indicated the formation of desired product. The reaction was quenched with brine at 0° C. The aqueous layer was extracted with EtOAc (2×800 mL). The combined organics were dried over sodium sulfate, filtered and concentrated to give the desired product (47.4 g, 84% yield). $^1$H NMR (CDCl$_3$) δ 7.3 (d, 2H), 7.2 (d, 2H), 4.0 (d, 2H), 3.9 (d, 2H), 2.9 (s, 1H), 1.2 (s, 9H), 0.0 (s, 9H).

Preparation 4a: tert-butyl 3-(4-bromophenyl)-3-hydroxyazetidine-1-carboxylate; (3-hydroxy-3-(4-bromo)phenyl-azetidine-1-carboxylic acid tert-butyl ester)

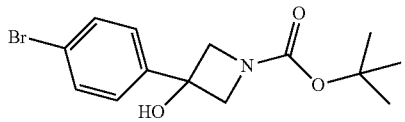 [SMILES: CC(C)(C)OC(=O)N1CC(O)(c2ccc(Br)cc2)C1]

A mixture of tert-butyl 3-hydroxy-3-(4-(trimethylsilyl)phenyl)azetidine-1-carboxylate (Preparation 3a, 45 g, 0.14 mol) and KBr (25 g, 0.21 mol) in acetic acid (1 L) and MeOH (100 mL) was heated at 60° C. for 20 minutes. Then N-chlorosuccinimide (22.4 g, 0.17 mol) was added to the reaction mixture and stirred at 60° C. for 2 hours. LC/MS indicated the reaction was complete (only product peak). After cooling to ambient temperature, the mixture was poured into ice-water (1 L). The mixture was extracted with CHCl$_3$ (2×800 mL). The combined organics were washed with 3M NaOH (2×600 mL), water (600 mL), dried over sodium sulfate, filtered and concentrated. The crude product was washed with ether to afford the desired product (35 g, 76% yield). $^1$H NMR (CDCl$_3$) δ 7.5 (d, 2H), 7.4 (d, 2H), 4.2 (s, 4H), 3.4 (s, 1H), 1.4 (s, 9H).

Alternatively, 3-hydroxy-3-(4-bromo)phenyl-azetidine-1-carboxylic acid tert-butyl ester can be prepared by adding i-PrMgCl solution in THF (2M in THF, 53.12 mL, 106.007 mmol, 1.2 eq) at −40° C. under nitrogen atmosphere over period of 20 minutes to a stirred solution of 1-bromo-4-iodobenzene (25 g, 88.339 mmol, 1 eq) in dry THF (250 mL). Resulting reaction mixture was stirred at −40° C. for 1.5 hours. After 1.5 hours, pre-dissolved 3-boc azetidinone (18.147 g, 106.007 mmol, 1.2 eq) in THF (100 mL) was added at −40° C. over a period of 40 minutes. Resulting reaction mixture was stirred at room temperature for 16 hours under nitrogen atmosphere. After complete consumption of starting material, reaction mixture was quenched with saturated ammonium chloride (80 mL) at 0° C. and extracted with ethyl acetate (200 mL×3). The organic layer was washed with brine (200 mL), dried over sodium sulfate and concentrated under reduced pressure to afford faint brown crude title compound (21.4 g, Crude). Crude compound was purified by pentane wash (4×50 mL) to afford the title compound as off white solid (18.5 g, impure). Impure compound was used as such for next reaction. $^1$H NMR (400 MHz, CDCl3) δ: 1.44 (s, 9H), 3.14 (s, 1H), 4.12-4.18 (m, 4H), 7.35-7.39 (m, 2H), 7.49-7.51 (m, 2H).

Preparation 5a: tert-butyl-3-(4-bromophenyl)-3-fluoroazetidine-1-carboxylate; (3-fluoro-3-(4-bromo)phenyl-azetidine-1-carboxylic acid tert-butyl ester)

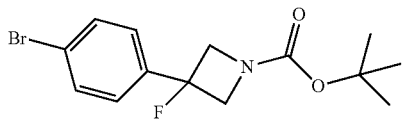 [SMILES: CC(C)(C)OC(=O)N1CC(F)(c2ccc(Br)cc2)C1]

Tert-butyl-3-(4-bromophenyl)-3-hydroxyazetidine-1-carboxylate (Preparation 4a, 25 g, 0.076 mol) in CH$_2$Cl$_2$ (500 mL) was cooled to −78° C. To this slurry was slowly added BAST (20.2 g, 0.09 mol) via addition funnel. The temperature of the reaction was increased slowly from −78° C. to ambient temperature. The mixture was stirred at ambient temperature overnight. LC/MS indicated that the reaction was complete. The reaction was quenched with saturated aqueous NaHCO$_3$ solution (500 mL) and 1M NaOH (500 mL). The aqueous layer was extracted with CH$_2$Cl$_2$ (2×800 mL). The combined organics were washed with aqueous citric acid (2×700 mL), dried over Na$_2$SO$_4$, filtered, and concentrated to afford the desired product as tan solid (24.4 g, 97% yield). $^1$H NMR (CDCl$_3$) δ 7.5 (d, 2H), 7.3 (d, 2H), 4.4 (m, 2H), 4.2 (m, 2H), 1.4 (s, 9H).

Alternatively, 3-fluoro-3-(4-bromo)phenyl-azetidine-1-carboxylic acid tert-butyl ester can be prepared by adding triethylamine (15.844 mL, 112.736 mmol, 2 eq) at room temperature to a stirred solution of triethylamine:trihydrofluoride (37.09 mL, 225.47 mmol, 4 eq) in DCM (150 mL). The resulting reaction mixture was cooled to −78° C., after 10 minutes. X-talFluor-E (42.732 g, 175.868 mmol, 3.12 eq) was added at −78° C. and stirred for 15 minutes at −78° C. After 15 minutes, a pre-dissolved solution of 3-(4-bromo-phenyl)-3-hydroxy-azetidine-1-carboxylic acid tert-butyl ester (18.5 g, 56.368 mmol, 1 eq) in DCM (100 mL) was added in drop wise manner over a period of 20 minutes at −78° C. Resulting reaction mixture was stirred at room temperature for 16 hours under nitrogen atmosphere. After complete consumption of starting material, reaction mixture was quenched with saturated NaHCO$_3$ solution (100 mL) and extracted with DCM (3×200 mL). Combined organic layer was dried over sodium sulphate and evaporated under reduced pressure to get yellow semisolid, which purified by Combiflash using 40 g Redisep column. Desired product is eluted in 4% ethyl acetate in hexane to afford off white solid (13.8 g, 74.15%). $^1$H NMR (400 MHz, CDCl3) δ: 1.46 (s, 9H), 4.15-4.22 (m, 2H), 4.34-4.42 (m, 2H), 7.32 (d, J=8.48 Hz, 2H), 7.54 (d, J=8.4 Hz, 2H), LC-MS (m/z): 330.2 [M+H], HPLC purity: 99.06%.

Example 1

1-(3-{4-[4-(3,5-dichloro-phenyl)-4-trifluoromethyl-4,5-dihydro-3H-pyrrol-2-yl]-phenyl}-3-fluoro-azetidin-1-yl)-2-methanesulfonyl-ethanone

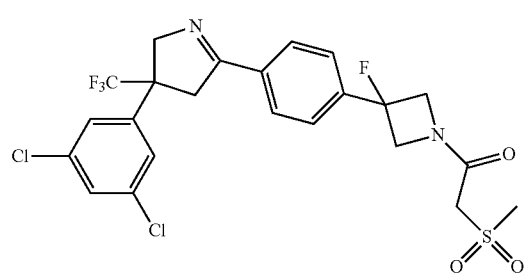 [SMILES: CS(=O)(=O)CC(=O)N1CC(F)(c2ccc(C3=NCC(c4cc(Cl)cc(Cl)c4)(C(F)(F)F)C3)cc2)C1]

Step 1: Preparation of 3-(4-acetyl-phenyl)-3-fluoro-azetidine-1-carboxylic acid tert-butyl ester

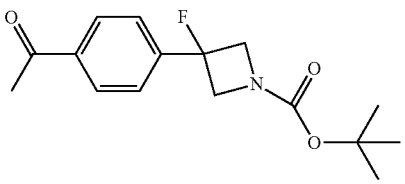 [SMILES: CC(=O)c1ccc(C2(F)CN(C(=O)OC(C)(C)C)C2)cc1]

In 100 mL autoclave vessel, a solution of 3-(4-bromo-phenyl)-3-fluoro-azetidine-1-carboxylic acid tert-butyl ester (Intermediate from Step 5a; 5 g, 15.142 mmol, 1 eq) in ethanol (17.5 mL) was degassed with nitrogen gas for 30 minutes at room temperature. TEA (3.79 mL, 27.256 mmol, 1.8 eq), butyl vinyl ether (BVE, 3.91 mL, 30.282 mmol, 2 eq), 1,3-bis(diphenylphosphino)propane (DPPP, 0.375 g, 0.909 mmol, 0.06 eq) were added followed by addition of Pd(OAc)$_2$ (0.102 g, 0.454 mmol, 0.03 eq.) at room temperature. Resulting reaction mixture was heated at 96° C. for 16 hours in an autoclave. After complete consumption of starting material, the reaction mixture was quenched with 1N HCl (5 mL, pH~2-3) and stirred for 2 hours at room temperature. After 2 hours, the pH of reaction mixture was adjusted to 7 by addition of saturated NaHCO$_3$ solution and extracted with ethyl acetate (3×50 mL). The combined organic layer was washed with brine (250 mL), dried over sodium sulphate and concentrated under reduced pressure to get crude compound as dark brown sticky oil (6.1 g, Crude). Crude compound was purified by column chromatography on silica gel using 230-400 silica mesh. Desired compound was eluted in 10% ethyl acetate in n-hexane to give product as off white semisolid (2.56 g, 57.66%). $^1$H NMR (400 MHz, CDCl$_3$) δ: 1.46 (s, 9H), 2.61 (s, 3H), 4.20 (dd, J$_1$=0.88 Hz, J$_2$=10.28 Hz, 1H), 4.24 (dd, J$_1$=0.92 Hz, J$_2$=10.36 Hz, 1H), 4.39 (dd, J$_1$=1.28 Hz, J$_2$=10.24 Hz, 1H), 4.44 (dd, J$_1$=1.28 Hz, J$_2$=10.20 Hz, 1H), 7.55 (dd, J$_1$=1.48 Hz, J$_2$=8.48 Hz, 2H), 8.00 (d, J=7.96 Hz, 2H), LC-MS (m/z): 294.1 (M+H).

Step 2: Preparation of 3-{4-[(Z)-3-(3,5-dichloro-phenyl)-4,4,4-trifluoro-but-2-enoyl]-phenyl}-3-fluoro-azetidine-1-carboxylic acid tert-butyl

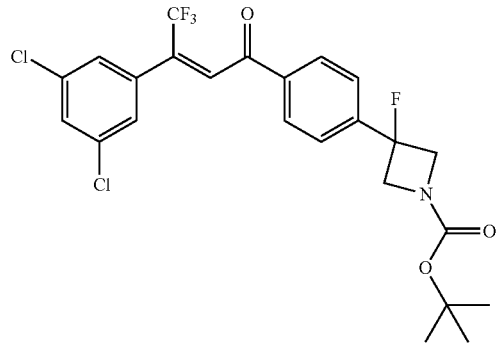 [SMILES: CC(C)(C)OC(=O)N1CC(F)(c2ccc(C(=O)/C=C(/c3cc(Cl)cc(Cl)c3)C(F)(F)F)cc2)C1]

In a 25 mL two neck RBF equipped with Dean-stark apparatus, to the stirred solution of 1-(3,5-dichloro-phenyl)-2,2,2-trifluoro-ethanone (2.56 g, 8.727 mmol, 1 eq.) in toluene (18 mL) and 1,1,1-trifluoromethyl benzene (18 mL) was added 3-(4-acetyl-phenyl)-3-fluoro-azetidine-1-carboxylic acid tert-butyl ester (2.43 g, 10.036 mmol, 1.15 eq) and Cs$_2$CO$_3$ (0.284 g, 0.873 mmol, 0.1 eq.) at room temperature. Resulting reaction mixture was stirred at 110° C. for 16 hours. After complete consumption of starting material, the reaction mixture was cooled to room temperature and was diluted with tert-butylmethyl ether (30 mL) and filtered through bed of celite. Filtrate was concentrated in vacuo to get crude compound as brown sticky oil (4.12 g, crude). Crude compound was purified by column chromatography on silica gel using 230-400 mesh. Desired compound was eluted in 20% ethyl acetate in n-hexane to give product as light yellow solid (2.2 g, 48.67%). $^1$H NMR (400 MHz, CDCl$_3$) δ: 1.47 (s, 9H), 4.09-4.14 (m, 1H), 4.17-4.22 (m, 1H), 4.37-4.40 (m, 1H), 4.42-4.45 (m, 1H), 7.13 (d, J=1.68 Hz, 2H), 7.31 (t, J=1.84 Hz, 1H), 7.38 (d, J=1.32 Hz, 1H), 7.56 (d, J=8.4 Hz, 2H), 7.86 (d, J=8.36 Hz, 2H). LC-MS (m/z): 516.0 (M−H).

Step 3: Preparation 3-{4-[3-(3,5-dichloro-phenyl)-4,4,4-trifluoro-3-nitromethyl-butyryl]-phenyl}-3-fluoro-azetidine-1-carboxylic acid tert-butyl ester

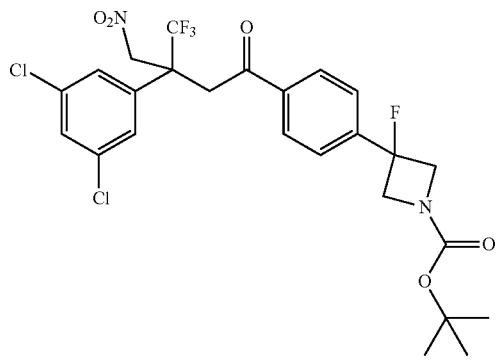 [SMILES: CC(C)(C)OC(=O)N1CC(F)(c2ccc(C(=O)CC(C[N+](=O)[O-])(c3cc(Cl)cc(Cl)c3)C(F)(F)F)cc2)C1]

To the stirred solution of 3-{4-[(Z)-3-(3,5-dichloro-phenyl)-4,4,4-trifluoro-but-2-enoyl]-phenyl}-3-fluoro-azetidine-1-carboxylic acid tert-butyl ester (1.2 g, 2.315 mmol, 1 eq.) in acetonitrile (10 mL) was added nitro methane (1.24 mL, 23.152 mmol, 10 eq) and DBU (0.33 mL, 2.246 mmol, 0.97 eq) at room temperature. The resulting reaction mixture was stirred at room temperature for 16 hours. After complete consumption of starting material, the reaction mixture was quenched with water (25 mL) and extracted with ethyl acetate (2×25 mL). Combined organic layers were washed with brine (60 mL), dried over sodium sulphate and concentrated to get crude compound semi solid (1.37 g, crude). Crude compound was purified by column chromatography on silica gel using 230-400 mesh. Desired compound was eluted in 10% ethyl acetate in n-hexane to give product as light yellow sticky liquid (1.09 g, 81.34%). LC-MS (m/z): 576.8 (M−H).

Step 4: Preparation of 3-{4-[4-(3,5-dichloro-phenyl)-4-trifluoromethyl-4,5-dihydro-3H-pyrrol-2-yl]-phenyl}-3-fluoro-azetidine-1-carboxylic acid tert-butyl ester

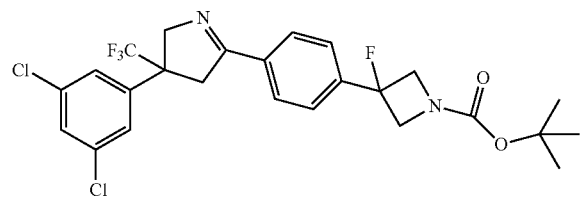 [SMILES: CC(C)(C)OC(=O)N1CC(F)(c2ccc(C3=NCC(c4cc(Cl)cc(Cl)c4)(C(F)(F)F)C3)cc2)C1]

The solution of 3-{4-[3-(3,5-dichloro-phenyl)-4,4,4-trifluoro-3-nitromethyl-butyryl]-phenyl}-3-fluoro-azetidine-1-carboxylic acid tert-butyl ester (1.09 g, 1.881 mmol, 1 eq.) in ethanol (12 mL) was purged with nitrogen gas for 30 minutes. To this reaction mixture was added Raney-Nickel (50% suspension in water, 0.24 g). Resulting reaction mixture was stirred under hydrogen balloon atmosphere for 16 hours at room temperature. After complete consumption of starting material, the reaction mixture was filtered through celite bed and washed with 10% MeOH in DCM (30 mL). Filtrate was concentrated to get off white solid (1.06 g, crude). Crude compound was purified by column chromatography on silica gel using 230-400 mesh. Desired compound was eluted in 7.5% ethyl acetate in n-hexane to give product as off white solid (0.27 g, 27%). $^1$H NMR (400 MHz, CDCl$_3$) δ: 1.47 (s, 9H), 3.45 (d, J=17.4 Hz, 1H), 3.79 (d, J=18.84 Hz, 1H), 4.20-4.27 (m, 2H), 4.38-4.46 (m, 3H), 4.89 (d, J=17.08 Hz, 1H), 7.25-7.27 (m, 2H), 7.36-7.37 (m, 1H), 7.54 (d, J=8.28 Hz, 2H), 7.89 (d, J=8.16 Hz, 2H). LC-MS (m/z): 531.1 (M+H).

Step 5: Preparation of hydrochloride salt of 3-(3,5-dichloro-phenyl)-5-[4-(3-fluoro-azetidin-3-yl)-phenyl]-3-trifluoromethyl-3,4-dihydro-2H-pyrrole

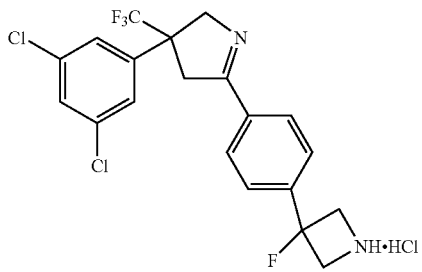

To a stirred solution of 3-{4-[4-(3,5-dichloro-phenyl)-4-trifluoromethyl-4,5-dihydro-3H-pyrrol-2-yl]-phenyl}-3-fluoro-azetidine-1-carboxylic acid tert-butyl ester (0.27 g, 0.508 mmol) in MeOH (13 mL) was purged HCl gas for 30 minutes at 0° C. After consumption of starting material, reaction mixture concentrated in vacuo and stripped out with chloroform (3×15 mL) to get product as off white solid (0.23 g, crude). Crude compound was used as such for next reaction. LC-MS (m/z): 430.8 (M+H).

Preparation of 1-(3-{4-[4-(3,5-dichloro-phenyl)-4-trifluoromethyl-4,5-dihydro-3H-pyrrol-2-yl]-phenyl}-3-fluoro-azetidin-1-yl)-2-methanesulfonyl-ethanone (Example 1)

To a stirred solution of hydrochloride salt of 3-(3,5-dichloro-phenyl)-5-[4-(3-fluoro-azetidin-3-yl)-phenyl]-3-trifluoromethyl-3,4-dihydro-2H-pyrrole (230 mg, 0.492 mmol, 1 eq) in DMF (5 mL) was added TEA (0.342 mL, 2.458 mmol, 5 eq), methanesulfonicacetic acid (0.135 g, 0.983 mmol, 2 eq), HOBt (0.066 g, 0.492 mmol, 1 eq) and EDC.HCl (0.141 g, 0.737 mmol, 1.5 eq) at room temperature. Resulting reaction mixture was stirred at room temperature for 16 hours under nitrogen atmosphere. After consumption of starting material, reaction mixture was quenched with water (10 mL) and extracted with ethyl acetate (3×15 mL). Combined organic layer was washed with LiCl Solution (2×40 mL) and brine (2×50 mL). Organic layer was dried over sodium sulphate and concentrated in vacuo to get brown colored semi solid (0.329 g, crude). Crude compound was purified by column chromatography on silica gel using 230-400 mesh. Desired compound was eluted in 1.2% methanol in DCM to give product as white solid (120 mg, 44.27%). $^1$H NMR (400 MHz, CDCl$_3$) δ: 3.17 (s, 3H), 3.45 (d, J=17.56 Hz, 1H), 3.79 (d, J=17.48 Hz, 1H), 3.87 (s, 2H), 4.40-4.47 (m, 2H), 4.51-4.59 (m, 1H), 4.79 (d, J=19.72 Hz, 2H), 4.91 (dd, J$_1$=1.44 Hz, J$_2$=17.08 Hz, 1H), 7.25-7.26 (m, 2H), 7.37 (t, J=1.76 Hz, 1H), 7.56 (d, J=8.4 Hz, 2H), 7.92 (d, J=8.12 Hz, 2H). LC-MS (m/z): 550.8 (M+H). HPLC purity: 99.10%.

Example 2

1-(3-{4-[4-(3,5-dichloro-phenyl)-4-trifluoromethyl-4,5-dihydro-3H-pyrrol-2-yl]-phenyl}-3-fluoro-azetidin-1-yl)-2-methyl-propan-1-one

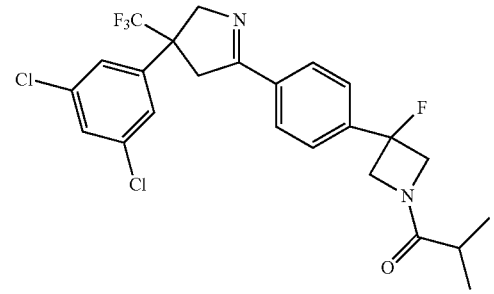 [SMILES: CC(C)C(=O)N1CC(F)(c2ccc(C3=NCC(c4cc(Cl)cc(Cl)c4)(C(F)(F)F)C3)cc2)C1]

This compound was prepared by using the procedures similar to that of Example 1, except that isobutyric acid was used in place of methane sulfonyl acetic acid. Yield: 0.155 g (28.92%). $^1$H NMR (400 MHz, CDCl$_3$) δ: 1.15 (t, J=5.86 Hz, 6H), 2.47-2.54 (m, 1H), 3.45 (d, J=17.52 Hz, 1H), 3.81 (d, J=17.56 Hz, 1H), 4.34-4.51 (m, 4H), 4.58-4.66 (m, 1H), 4.89 (d, J=16.96 Hz, 1H), 7.25-7.26 (m, 2H), 7.37 (s, 1H), 7.53 (d, J=8.28 Hz, 2H), 7.91 (d, J=8.16 Hz, 2H). LC-MS (m/z): 500.8 (M+H). HPLC purity: 98.85%.

Example 3

3-(3,5-dichloro-4-fluorophenyl)-5-(4-{3-fluoro-1-[(methylsulfonyl)-acetyl]azetidin-3-yl}phenyl)-3-(trifluoromethyl)-3,4-dihydro-2H-pyrrole

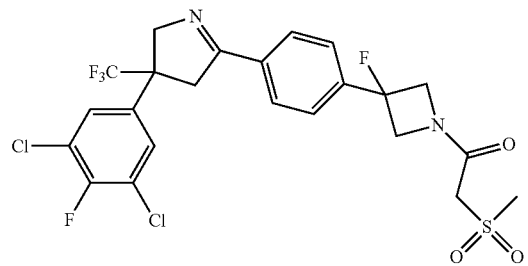 [SMILES: CS(=O)(=O)CC(=O)N1CC(F)(c2ccc(C3=NCC(c4cc(Cl)c(F)c(Cl)c4)(C(F)(F)F)C3)cc2)C1]

Step 1: Preparation of 3-{4-[(Z)-3-(3,5-dichloro-4-fluoro-phenyl)-4,4,4-trifluoro-but-2-enoyl]-phenyl}-3-fluoro-azetidine-1-carboxylic acid tert-butyl ester

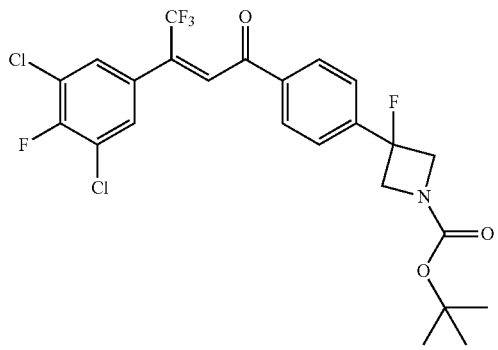 [SMILES: CC(C)(C)OC(=O)N1CC(F)(c2ccc(C(=O)/C=C(/c3cc(Cl)c(F)c(Cl)c3)C(F)(F)F)cc2)C1]

This compound was prepared similarly to Example 1 intermediate procedures except that 1-(3,5-dichloro-4-fluoro-phenyl)-2,2,2-trifluoro-ethanone was used in place of 1-(3,5-dichloro-phenyl)-2,2,2-trifluoro-ethanone. Yield: 4.1 g (64.06%). $^1$H NMR (400 MHz, CDCl$_3$) δ: 1.47 (s, 9H), 4.16 (d, J=10.32 Hz, 1H), 4.21 (d, J=10.44 Hz, 1H), 4.39 (d, J=10.52 Hz, 1H), 4.45 (d, J=10.32 Hz, 1H), 7.23 (d, J=6.08 Hz, 2H), 7.40 (d, J=1.08 Hz, 1H), 7.58 (d, J=8.4 Hz, 2H), 7.88 (d, J=8.28 Hz, 2H). LC-MS (m/z): 535.9 (M+H).

Step 2: Preparation 3-{4-[3-(3,5-Dichloro-4-fluoro-phenyl)-4,4,4-trifluoro-3-nitromethyl-butyryl]-phenyl}-3-fluoro-azetidine-1-carboxylic acid tert-butyl ester

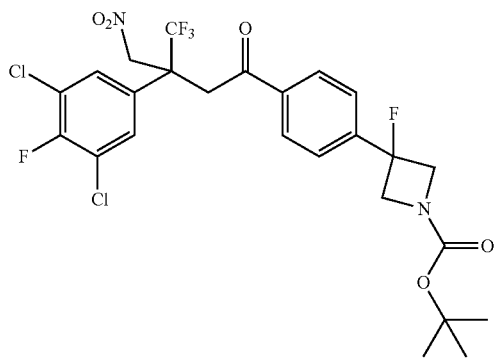 [SMILES: CC(C)(C)OC(=O)N1CC(F)(c2ccc(C(=O)CC(C[N+](=O)[O-])(c3cc(Cl)c(F)c(Cl)c3)C(F)(F)F)cc2)C1]

This compound was prepared similarly to Example 1 intermediate procedures except that 3-{4-[(Z)-3-(3,5-dichloro-4-fluoro-phenyl)-4,4,4-trifluoro-but-2-enoyl]-phenyl}-3-fluoro-azetidine-1-carboxylic acid tert-butyl ester was used in place of 3-{4-[(Z)-3-(3,5-dichloro-phenyl)-4,4,4-trifluoro-but-2-enoyl]-phenyl}-3-fluoro-azetidine-1-carboxylic acid tert-butyl ester. Yield: 3.9 g (82.98%). $^1$H NMR (400 MHz, CDCl$_3$) δ: 1.48 (s, 9H), 3.96 (d, J=18.72 Hz, 1H), 4.16 (d, J=18.88 Hz, 1H), 4.21-4.26 (m, 2H), 4.40-4.42 (m, 1H), 4.45-4.48 (m, 1H), 5.43 (d, J=12.32 Hz, 1H), 5.57 (d, J=12.32 Hz, 1H), 7.26 (d, J=5.76 Hz, 2H), 7.63 (d, J=8.48 Hz, 2H), 8.01 (d, J=8.32 Hz, 2H). LC-MS (m/z): 595.2 (M−H).

Step 3: Preparation of 3-{4-[4-(3,5-dichloro-4-fluoro-phenyl)-4-trifluoromethyl-4,5-dihydro-3H-pyrrol-2-yl]-phenyl}-3-fluoro-azetidine-1-carboxylic acid tert-butyl ester

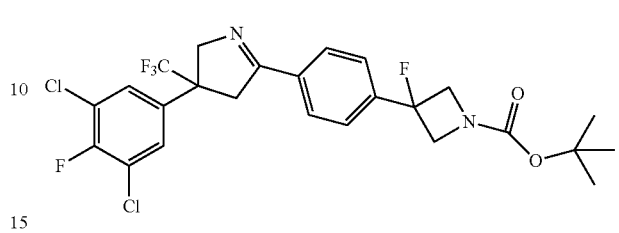

This compound was prepared similarly to Example 1 intermediate procedures except that 3-{4-[3-(3,5-dichloro-4-fluoro-phenyl)-4,4,4-trifluoro-3-nitromethyl-butyryl]-phenyl}-3-fluoro-azetidine-1-carboxylic acid tert-butyl ester was used in place of 3-{4-[3-(3,5-dichloro-phenyl)-4,4,4-trifluoro-3-nitromethyl-butyryl]-phenyl}-3-fluoro-azetidine-1-carboxylic acid tert-butyl ester. Yield: 1.2 g (33.43%). $^1$H NMR (400 MHz, CDCl$_3$) δ: 1.47 (s, 9H), 3.44 (d, J=17.2 Hz, 1H), 3.79 (dd, J$_1$=1.6 Hz, J$_2$=17.32 Hz, 1H), 4.19-4.27 (m, 2H), 4.38-4.46 (m, 3H), 4.88 (dd, J$_1$=1.52 Hz, J$_2$=16.96 Hz, 1H), 7.33 (d, J=5.96 Hz, 2H), 7.54 (d, J=8.32 Hz, 2H), 7.89 (d, J=8.12 Hz, 2H). LC-MS (m/z): 548.9 (M+H).

Step 4: Preparation of 3-(3,5-dichloro-4-fluoro-phenyl)-5-[4-(3-fluoro-azetidin-3-yl)-phenyl]-3-trifluoromethyl-3,4-dihydro-2H-pyrrole hydrochloride salt

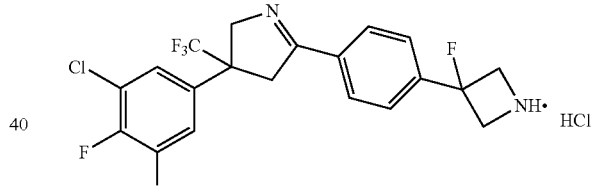

This compound was prepared similarly to Example 1 intermediate procedures except that 3-{4-[4-(3,5-dichloro-phenyl)-4-trifluoromethyl-4,5-dihydro-3H-pyrrol-2-yl]-phenyl}-3-fluoro-azetidine-1-carboxylic acid tert-butyl ester was used in place of 3-{4-[4-(3,5-dichloro-4-fluoro-phenyl)-4-trifluoromethyl-4,5-dihydro-3H-pyrrol-2-yl]-phenyl}-3-fluoro-azetidine-1-carboxylic acid tert-butyl ester. Yield: 1.05 g (Crude). Crude compound was used as such for next reaction. $^1$H NMR (400 MHz, DMSO-d6) δ: 3.84 (d, J=18.24 Hz, 2H), 4.46-4.64 (m, 5H), 4.85 (d, J=17.4 Hz, 1H), 7.75-7.79 (m, 4H), 8.05 (d, J=8.12 Hz, 2H), 9.63 (bs, 1H), 9.93 (bs, 1H). LC-MS (m/z): 448.8 (M+H).

Preparation of 3-(3,5-dichloro-4-fluorophenyl)-5-(4-{3-fluoro-1-[(methylsulfonyl)-acetyl]azetidin-3-yl}phenyl)-3-(trifluoromethyl)-3,4-dihydro-2H-pyrrole (Example 3)

This compound was prepared similarly to Example 1 except that 3-(3,5-dichloro-4-fluoro-phenyl)-5-[4-(3-fluoro-azetidin-3-yl)-phenyl]-3-trifluoromethyl-3,4-dihydro-2H-pyrrole hydrochloride salt was used in place of 3-(3,5-dichloro-phenyl)-5-[4-(3-fluoro-azetidin-3-yl)-phenyl]-3- trifluoromethyl-3,4-dihydro-2H-pyrrole hydrochloride salt. Yield: 140 mg (36.19%). $^1$H NMR (400 MHz, CDCl$_3$) δ: 3.17 (s, 3H), 3.43 (d, J=17.44 Hz, 1H), 3.79 (d, J=17.36 Hz, 1H), 3.87 (s, 2H), 4.39-4.60 (m, 3H), 4.79 (d, J=19.84 Hz, 2H), 4.86-4.90 (m, 1H), 7.32 (d, J=5.96 Hz, 2H), 7.56 (d, J=8.32 Hz, 2H), 7.91 (d, J=8.16 Hz, 2H). LC-MS (m/z): 569.0. (M+H). HPLC Purity: 99.15%.

Example 4

3-(3,5-dichloro-4-fluorophenyl)-5-[4-(3-fluoro-1-isobutyrylazetidin-3-yl)phenyl]-3-(trifluoromethyl)-3,4-dihydro-2H-pyrrole

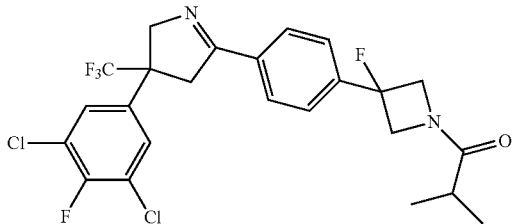 [SMILES: CC(C)C(=O)N1CC(F)(c2ccc(C3=NCC(c4cc(Cl)c(F)c(Cl)c4)(C(F)(F)F)C3)cc2)C1]

This compound was prepared similarly to Example 3 except that isobutyric acid was used in place of methane sulfonyl acetic acid. Yield: 0.240 g (44.9%). $^1$H NMR (400 MHz, DMSO-d6) δ: 1.02 (t, J=7.16 Hz, 6H), 2.53-2.57 (m, 1H), 3.75 (d, J=18.16 Hz, 1H), 3.87 (d, J=18.01 Hz, 1H), 4.27-4.34 (m, 2H), 4.44 (d, J=17.32 Hz, 1H), 4.63-4.70 (m, 2H), 4.82 (d, J=17.4 Hz, 1H), 7.64 (d, J=8.24 Hz, 2H), 7.78 (d, J=6.2 Hz, 2H), 7.98 (d, J=8.08 Hz, 2H). LC-MS (m/z): 519.2 (M+H). HPLC purity: 96.54%.

Example 5

1-(3-fluoro-3-{4-[4-(3,4,5-trichloro-phenyl)-4-trifluoromethyl-4,5-dihydro-3H-pyrrol-2-yl]-phenyl}-azetidin-1-yl)-2-methanesulfonyl-ethanone

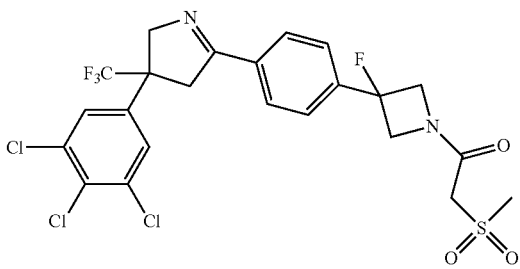 [SMILES: CS(=O)(=O)CC(=O)N1CC(F)(c2ccc(C3=NCC(c4cc(Cl)c(Cl)c(Cl)c4)(C(F)(F)F)C3)cc2)C1]

Step 1: Preparation of 3-fluoro-3-{4-[(Z)-4,4,4-trifluoro-3-(3,4,5-trichloro-phenyl) but-2-enoyl]-phenyl}azetidine-1-carboxylic acid tert-butyl ester

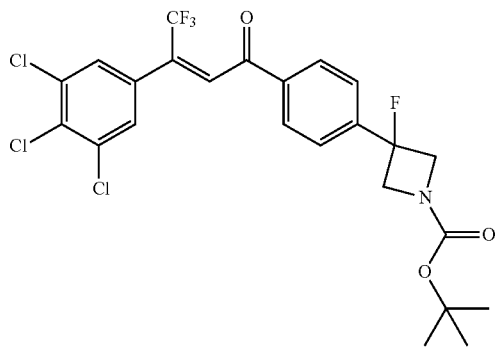 [SMILES: CC(C)(C)OC(=O)N1CC(F)(c2ccc(C(=O)/C=C(/c3cc(Cl)c(Cl)c(Cl)c3)C(F)(F)F)cc2)C1]

This compound was prepared similarly to Example 1 intermediate procedures except that 2,2,2-trifluoro-1-(3,4,5-trichloro-phenyl)ethanone was used in place of 1-(3,5-dichloro-phenyl)-2,2,2-trifluoro-ethanone. Yield: 4.5 g (68.18%). $^1$H NMR (400 MHz, CDCl$_3$) δ: 1.47 (s, 9H), 4.16 (d, J=10.4 Hz, 1H), 4.21 (d, J=10.32 Hz, 1H), 4.39 (d, J=10.68 Hz, 1H), 4.44 (d, J=9.92 Hz, 1H), 7.28 (s, 2H), 7.42 (d, J=1.12 Hz, 1H), 7.56-7.58 (m, 2H), 7.87 (d, J=8.24 Hz, 2H). LC-MS (m/z): 550.1 (M–H).

Step 2: Preparation of 3-fluoro-3-{4-[4,4,4-trifluoro-3-nitromethyl-3-(3,4,5-trichloro-phenyl)-butyryl]-phenyl}-azetidine-1-carboxylic acid tert-butyl ester

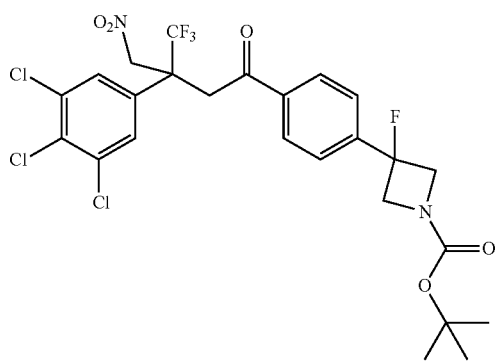 [SMILES: CC(C)(C)OC(=O)N1CC(F)(c2ccc(C(=O)CC(C[N+](=O)[O-])(c3cc(Cl)c(Cl)c(Cl)c3)C(F)(F)F)cc2)C1]

This compound was prepared similarly to Example 1 intermediate procedures except that 3-fluoro-3-{4-[(Z)-4,4,4-trifluoro-3-(3,4,5-trichloro-phenyl)-but-2-enoyl]-phenyl}-azetidine-1-carboxylic acid tert-butyl ester was used in place of 3-{4-[(Z)-3-(3,5-dichloro-phenyl)-4,4,4-trifluoro-but-2-enoyl]-phenyl}-3-fluoro-azetidine-1-carboxylic acid tert-butyl ester. Yield: 3.26 g (65.07%). $^1$H NMR (400 MHz, CDCl$_3$) δ: 1.48 (s, 9H), 3.95 (d, J=18.72 Hz, 1H), 4.16 (d, J=18.88 Hz, 1H), 4.21-4.26 (m, 2H), 4.40-4.48 (m, 2H), 5.43 (d, J=12.32 Hz, 1H), 5.57 (d, J=12.36 Hz, 1H), 7.32 (s, 2H), 7.63 (d, J=8.44 Hz, 2H), 8.01 (d, J=8.2 Hz, 2H). LC-MS (m/z): 613.0 (M–H).

Step 3: Preparation of 3-fluoro-3-{4-[4-(3,4,5-trichloro-phenyl)-4-trifluoromethyl-4,5-dihydro-3H-pyrrol-2-yl]-phenyl}-azetidine-1-carboxylic acid tert-butyl ester

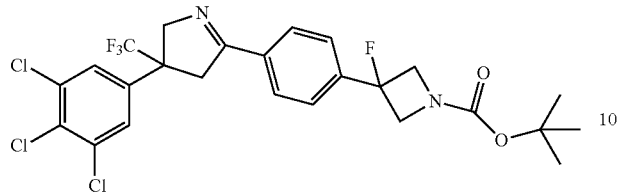

This compound was prepared similarly to Example 1 intermediate procedures except that 3-fluoro-3-{4-[4-(3,4,5-trichloro-phenyl)-4-trifluoromethyl-4,5-dihydro-3H-pyrrol-2-yl]-phenyl}-azetidine-1-carboxylic acid tert-butyl ester was used in place of 3-{4-[3-(3,5-dichloro-phenyl)-4,4,4-trifluoro-3-nitromethyl-butyryl]-phenyl}-3-fluoro-azetidine-1-carboxylic acid tert-butyl ester. Yield: 0.97 g (32.44%). $^1$H NMR (400 MHz, CDCl$_3$) δ: 1.47 (s, 9H), 3.43 (d, J=17.44 Hz, 1H), 3.79 (dd, J$_1$=1.68 Hz, J$_2$=17.4 Hz, 1H), 4.19-4.27 (m, 2H), 4.37-4.46 (m, 3H), 4.87 (dd, J$_1$=1.44 Hz, J$_2$=17.04 Hz, 1H), 7.39 (s, 2H), 7.54 (d, J=8.4 Hz, 2H), 7.89 (d, J=8.24 Hz, 2H). LC-MS (m/z): 566.9 (M+H).

Step 4: Preparation of 5-[4-(3-fluoro-azetidin-3-yl)-phenyl]-3-(3,4,5-trichloro-phenyl)-3-trifluoromethyl-3,4-dihydro-2H-pyrrole hydrochloride salt

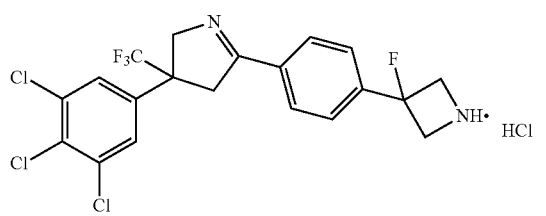

This compound was prepared similarly to Example 1 intermediate procedures except that 3-fluoro-3-{4-[4-(3,4,5-trichloro-phenyl)-4-trifluoromethyl-4,5-dihydro-3H-pyrrol-2-yl]-phenyl}-azetidine-1-carboxylic acid tert-butyl ester was used in place of 3-{4-[4-(3,5-dichloro-4-fluoro-phenyl)-4-trifluoromethyl-4,5-dihydro-3H-pyrrol-2-yl]-phenyl}-3-fluoro-azetidine-1-carboxylic acid tert-butyl ester. Yield: 0.91 g (Crude). Crude was used as such for next reaction. $^1$H NMR (400 MHz, DMSO-d6) δ: 3.94 (d, J=19.04 Hz, 1H), 4.45-4.61 (m, 6H), 4.85 (d, J=17.28 Hz, 1H), 7.74 (d, J=8.2 Hz, 2H), 7.82 (s, 2H), 8.04 (d, J=8.16 Hz, 2H), 9.51 (bs, 1H), 9.86 (bs, 1H). LC-MS (m/z): 464.9 (M+H).

Preparation of 1-(3-fluoro-3-{4-[4-(3,4,5-trichloro-phenyl)-4-trifluoromethyl-4,5-dihydro-3H-pyrrol-2-yl]-phenyl}-azetidin-1-yl)-2-methanesulfonyl-ethanone (Example 5)

This compound was prepared similarly to Example 1 except that 5-[4-(3-fluoro-azetidin-3-yl)-phenyl]-3-(3,4,5-trichloro-phenyl)-3-trifluoromethyl-3,4-dihydro-2H-pyrrole hydrochloride salt was used in place of 3-(3,5-dichloro-phenyl)-5-[4-(3-fluoro-azetidin-3-yl)-phenyl]-3-trifluoromethyl-3,4-dihydro-2H-pyrrole hydrochloride salt. Yield: 194 mg (36.15%). $^1$H NMR (400 MHz, DMSO-d6) δ: 3.13 (s, 3H), 3.75 (d, J=18.2 Hz, 1H), 3.89 (d, J=18.2 Hz, 1H), 4.27 (s, 2H), 4.39-4.46 (m, 3H), 4.74-4.85 (m, 3H), 7.65 (d, J=8.28 Hz, 2H), 7.81 (s, 2H), 7.99 (d, J=8.08 Hz, 2H). LC-MS (m/z): 584.8 (M+H). HPLC Purity: 95.07%.

Example 6

5-[4-(3-fluoro-1-isobutyrylazetidin-3-yl)phenyl]-3-(3,4,5-trichloro-phenyl)-3-(trifluoromethyl)-3,4-dihydro-2H-pyrrole

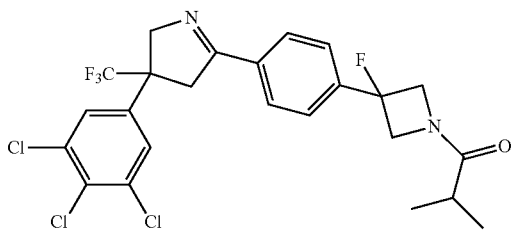 [SMILES: CC(C)C(=O)N1CC(F)(c2ccc(C3=NCC(c4cc(Cl)c(Cl)c(Cl)c4)(C(F)(F)F)C3)cc2)C1]

This compound was prepared similarly to that of Example 5 except that isobutyric acid was used in place of methane sulfonyl acetic acid. Yield: 0.184 g (37.49%). $^1$H NMR (400 MHz, DMSO-d6) δ: 1.02 (t, J=7.16 Hz, 6H), 2.49-2.57 (m, 1H), 3.75 (d, J=18.16 Hz, 1H), 3.88 (d, J=18.24 Hz, 1H), 4.27-4.34 (m, 2H), 4.44 (d, J=17.04 Hz, 1H), 4.63-4.70 (m, 2H), 4.83 (d, J=17.4 Hz, 1H), 7.64 (d, J=8.24 Hz, 2H), 7.81 (s, 2H), 7.98 (d, J=8.08 Hz, 2H). LC-MS (m/z): 534.9 (M+H). HPLC Purity: 95.15%.

Example 7

1-(3-{4-[5-(3,5-dichloro-4-fluoro-phenyl)-5-trifluoromethyl-[1,4,2]dioxazol-3-yl]-phenyl}-3-fluoro-azetidin-1-yl)-2-methanesulfonyl-ethanone

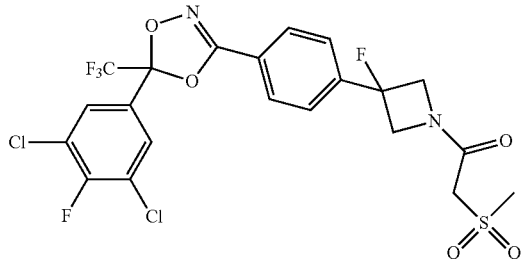 [SMILES: CS(=O)(=O)CC(=O)N1CC(F)(c2ccc(C3=NOC(c4cc(Cl)c(F)c(Cl)c4)(C(F)(F)F)O3)cc2)C1]

Step 1: Preparation of 3-fluoro-3-(4-formyl-phenyl)-azetidine-1-carboxylic acid tert-butyl ester

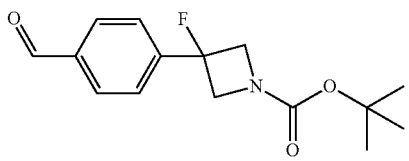 [SMILES: CC(C)(C)OC(=O)N1CC(F)(c2ccc(C=O)cc2)C1]

To a stirred solution of 3-(4-bromo-phenyl)-3-fluoro-azetidine-1-carboxylic acid tert-butyl ester (5 g, 15.14 mmol, 1 eq) in dry THF (60 mL) was added n-BuLi (16.6 mL, 18.17 mmol, 1.2 eq) at −78° C. under nitrogen atmosphere. Reaction mixture was stirred for 10 minutes at −78° C. under nitrogen atmosphere. At −78° C., DMF (1.748 mL, 22.71 mmol, 1.5 eq) was added in drop wise manner over a period of 10 minutes. Resulting reaction mixture was allowed to warm to −20° C. and stirred for 3 hours at −20° C. After complete consumption of starting material, reaction was quenched with 10% NH₄Cl solution (10 mL) followed by water (100 mL) and extracted with ethyl acetate (3×40 mL). Combined organic phase was washed with brine solution (50 mL), dried over anhydrous Na₂SO₄ and concentrated under reduced pressure to afford title compound as pale yellow thick oil (4.5 g, Crude). Crude compound was used as such for next reaction. LC-MS (m/z): 279.3 (M+H).

Step 2: Preparation of 3-fluoro-3-[4-(hydroxyimino-methyl)-phenyl]-azetidine-1-carboxylic acid tert-butyl ester

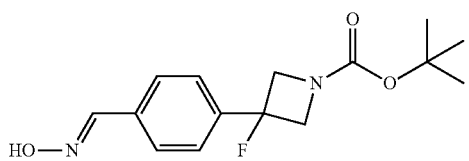 [SMILES: CC(C)(C)OC(=O)N1CC(F)(c2ccc(/C=N/O)cc2)C1]

To a stirred solution of 3-fluoro-3-(4-formyl-phenyl)-azetidine-1-carboxylic acid tert-butyl ester (4.5 g, 16.11 mmol, 1 eq) in mixture of methanol (50 mL) and water (40 mL) was added hydroxyl amine hydrochloride (1.66 g, 24.17 mmol, 1.5 eq) followed by addition of sodium acetate (2.37 g, 29.0 mmol, 1.8 eq) at room temperature. Resulting reaction mixture was stirred at room temperature for 24 hours. After complete consumption of starting material, reaction mixture was concentrated in vacuo to afford to yellow colored residue, which was diluted by water (120 mL) and extracted with ethyl acetate (3×80 mL). Combined organic phase was washed with brine solution (70 mL), dried over anhydrous Na₂SO₄ and concentrated under reduced pressure to get yellow semi solid (2.3 g, Crude). Crude was purified by Combiflash using 40 g Redisep column. Desired compound was eluted in 19% ethyl acetate in hexane to afford title compound as yellow semi solid (1.0 g, 21.1%). ¹H NMR (400 MHz, CDCl₃) δ: 1.47 (s, 9H), 4.20-4.27 (m, 2H), 4.36-4.44 (m, 2H), 7.47 (d, J=8.28 Hz, 2H), 7.64 (d, J=8.2 Hz, 2H), 8.13 (s, 1H). LC-MS (m/z): 293.1 (M−H).

Step 3: Preparation of 3-{4-[5-(3,5-dichloro-4-fluoro-phenyl)-5-trifluoromethyl-[1,4,2]dioxazol-3-yl]-phenyl}-3-fluoro-azetidine-1-carboxylic acid tert-butyl ester

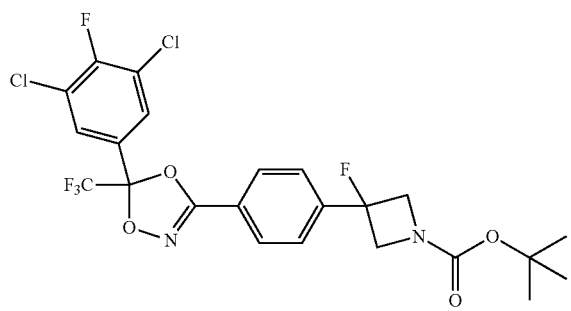 [SMILES: CC(C)(C)OC(=O)N1CC(F)(c2ccc(C3=NOC(c4cc(Cl)c(F)c(Cl)c4)(C(F)(F)F)O3)cc2)C1]

To a stirred solution of 3-fluoro-3-[4-(hydroxyimino-methyl)-phenyl]-azetidine-1-carboxylic acid tert-butyl ester (0.5 g, 1.7 mmol, 1 eq) in DMF (6.5 mL) was added N-chloro succinimide (0.227 g, 1.7 mmol, 1 eq). Reaction mixture was stirred at 55° C. for 1 hour. After 1 hour (chloro intermediate formation), 1-(3,5-dichloro-4-fluoro-phenyl)-2,2,2-trifluoro-ethanone (0.45 g, 1.73 mmol, 1.02 eq) was added followed by addition of sodium bicarbonate (0.146 g, 1.74 mmol, 1.02 eq) at room temperature. Resulting reaction mixture was stirred at 55° C. for 3 hours under nitrogen atmosphere. After complete consumption of starting material, reaction mixture was quenched by water (10 mL) and extracted with ethyl acetate (3×50 mL). Combined organic phase was washed with brine solution (20 mL), dried over anhydrous Na₂SO₄ and concentrated under reduced pressure to get brown thick oil (0.6 g, Crude). Crude was purified by Combiflash using 40 g Redisep column. Desired compound was eluted in 25% ethyl acetate in hexane to afford title compound as colorless thick oil (0.37 g, 39.32%). ¹H NMR (400 MHz, CDCl₃) δ: 1.47 (s, 9H), 4.16-4.24 (m, 2H), 4.38-4.47 (m, 2H), 7.59 (d, J=8.44 Hz, 2H), 7.66 (d, J=5.88 Hz, 2H), 7.89 (d, J=8.2 Hz, 2H), LC-MS (m/z): No ionization.

Step 4: Preparation of trifluoroacetic acid salt of 5-(3,5-dichloro-4-fluoro-phenyl)-3-[4-(3-fluoro-azetidin-3-yl)-phenyl]-5-trifluoromethyl-[1,4,2]dioxazole

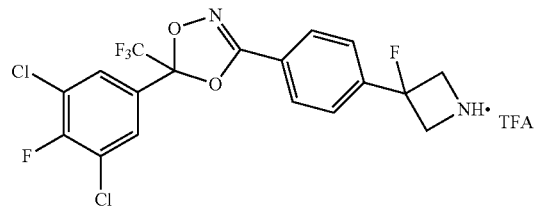

To a stirred solution of 3-{4-[5-(3,5-dichloro-4-fluoro-phenyl)-5-trifluoromethyl-[1,4,2]dioxazol-3-yl]-phenyl}-3-fluoro-azetidine-1-carboxylic acid tert-butyl ester (0.37 g, 0.67 mmol, 1 eq) in DCM (7 mL) was added trifluoro acetic acid (1.54 mL, 20.06 mmol, 30 eq) at 0° C. in drop wise manner over period of 15 minutes. Resulting reaction mixture was stirred at room temperature for 1 hour. After complete consumption of starting material, reaction mixture was concentrated in vacuo to afford brown thick oil. Brown thick oil was stripped out with chloroform (3×20 mL) to remove traces of trifluoro acetic acid under reduced pressure to afford title compound as brown thick oil (0.35 g, Crude). Crude compound was used as such for the next reaction. LC-MS (m/z): 453.0 (M+H).

Preparation of 1-(3-{4-[5-(3,5-Dichloro-4-fluoro-phenyl)-5-trifluoromethyl-[1,4,2]dioxazol-3-yl]-phenyl}-3-fluoro-azetidin-1-yl)-2-methanesulfonyl-ethanone (Example 7)

To a stirred solution of trifluoroacetic acid salt of 5-(3,5-dichloro-4-fluoro-phenyl)-3-[4-(3-fluoro-azetidin-3-yl)-phenyl]-5-trifluoromethyl-[1,4,2]dioxazole (0.35 g, 0.77 mmol, 1 eq) in DMF (5 mL) was added triethyl amine (0.867 mL, 6.178 mmol, 8 eq.), followed by addition of EDC.HCl (0.22 g, 1.15 mmol, 1.5 eq), HOBt (0.104 g, 0.77 mmol, 1 eq) and methanesulfonyl-acetic acid (0.213 g, 1.54 mmol, 2 eq) at room temperature. Resulting reaction mixture was stirred at room temperature for 18 hours under nitrogen atmosphere. After complete consumption of starting material, reaction mixture was quenched by water (50 mL) and extracted with ethyl acetate (3×30 mL). Combined organic phase was washed with saturated solution of LiCl solution (30 mL), brine (30 mL), dried over anhydrous Na₂SO₄ and concentrated under reduced pressure to get brown thick oil (0.51 g, Crude). Crude was purified by combiflash using 40 g Redisep column. Desired compound was eluted in 47% ethyl acetate in hexane to afford title compound as off white solid (0.225 g, 50.82%). $^1$H NMR (400 MHz, CDCl₃) δ: 3.17 (s, 3H), 3.87 (s, 2H), 4.37-4.45 (m, 1H), 4.52-4.60 (m, 1H), 4.80 (d, J=19.64 Hz, 2H), 7.61-7.65 (m, 4H), 7.91 (d, J=8.24 Hz, 2H), LC-MS (m/z): 571.0 (M−H), HPLC Purity: 93.59%.

Example 8

1-(3-{4-[5(3,5-dichloro-4-fluoro-phenyl)-5-trifluoromethyl-[1,4,2]dioxazol-3-yl]-phenyl}-3-fluoro-azetidin-1-yl)-2-methyl-propan-1-one

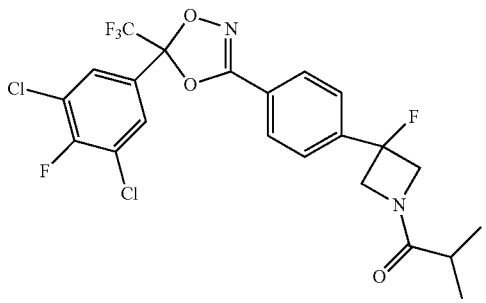 [SMILES: CC(C)C(=O)N1CC(F)(c2ccc(C3=NOC(c4cc(Cl)c(F)c(Cl)c4)(C(F)(F)F)O3)cc2)C1]

This compound was prepared similarly to that of Example 7 except that isobutyric acid was used in place of methane sulfonyl acetic acid. Yield: 0.292 g (48.77%). $^1$H NMR (400 MHz, CDCl₃) δ: 1.15 (d, J=6.8 Hz, 6H), 2.46-2.53 (m, 1H), 4.38-4.60 (m, 4H), 7.57 (d, J=8.36 Hz, 2H), 7.65 (d, J=5.96 Hz, 2H), 7.9 (d, J=8.16 Hz, 2H), LC-MS (m/z): 522.9 (M+H), HPLC Purity: 95.27%.

Example 9

1-(3-{4-[5-(3,5-dichloro-phenyl)-5-trifluoromethyl-[1,4,2]dioxazol-3-yl]-phenyl}-3-fluoro-azetidin-1-yl)-2-methanesulfonyl-ethanone

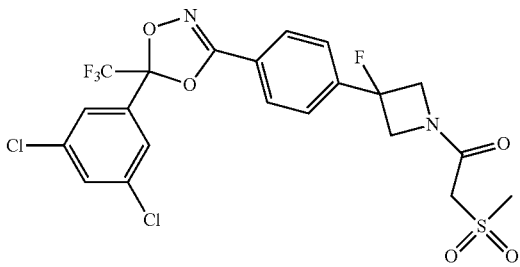 [SMILES: CS(=O)(=O)CC(=O)N1CC(F)(c2ccc(C3=NOC(c4cc(Cl)cc(Cl)c4)(C(F)(F)F)O3)cc2)C1]

Step 1: Preparation of 3-{4-[5-(3,5-dichloro-phenyl)-5-trifluoromethyl-[1,4,2]dioxazol-3-yl]-phenyl}-3-fluoro-azetidine-1-carboxylic acid tert-butyl ester

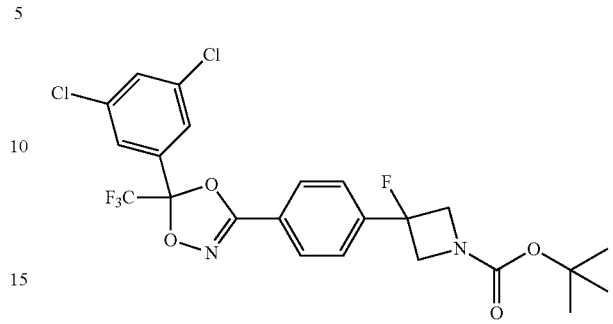

This compound was prepared similarly to Example 7 intermediate procedures except that 1-(3,5-dichloro-phenyl)-2,2,2-trifluoro-ethanone was used in place of 1-(3,5-dichloro-4-fluoro-phenyl)-2,2,2-trifluoro-ethanone. Yield: 1.5 g (58.82%). $^1$H NMR (400 MHz, CDCl₃) δ: 1.47 (s, 9H), 4.17-4.24 (m, 2H), 4.38-4.47 (m, 2H), 7.51 (t, J=1.84 Hz, 1H), 7.57-7.60 (m, 4H), 7.88-7.91 (m, 2H). LC-MS (m/z): No ionization.

Step 2: Preparation of trifluoroacetic acid salt of 5-(3,5-dichloro-phenyl)-3-[4-(3-fluoro-azetidin-3-yl)-phenyl]-5-trifluoromethyl-[1,4,2]dioxazole

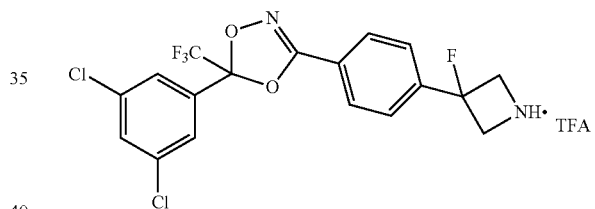

This compound was prepared similarly to Example 7 intermediate procedures except that 3-{4-[5-(3,5-dichloro-phenyl)-5-trifluoromethyl-[1,4,2]dioxazol-3-yl]-phenyl}-3-fluoro-azetidine-1-carboxylic acid tert-butyl ester was used in place of 3-{4-[5-(3,5-dichloro-4-fluoro-phenyl)-5-trifluoromethyl-[1,4,2]dioxazol-3-yl]-phenyl}-3-fluoro-azetidine-1-carboxylic acid tert-butyl ester. Yield: 1.6 g (Crude). Crude compound was used as such for next reaction. LC-MS (m/z): 434.8 (M+H).

Preparation of 1-(3-{4-[5-(3,5-dichloro-phenyl)-5-trifluoromethyl-[1,4,2]dioxazol-3-yl]-phenyl}-3-fluoro-azetidin-1-yl)-2-methanesulfonyl-ethanone (Example 9)

This compound was prepared similarly to Example 7 except that trifluoroacetic acid salt of 5-(3,5-dichloro-phenyl)-3-[4-(3-fluoro-azetidin-3-yl)-phenyl]-5-trifluoromethyl-[1,4,2]dioxazole was used in place of trifluoroacetic acid salt of 5-(3,5-dichloro-4-fluoro-phenyl)-3-[4-(3-fluoro-azetidin-3-yl)-phenyl]-5-trifluoromethyl-[1,4,2]dioxazole. Yield: 0.270 g (26.47%). $^1$H NMR (400 MHz, CDCl₃) δ: 3.17 (s, 3H), 3.87 (s, 2H), 4.37-4.45 (m, 1H), 4.52-4.60 (m, 1H), 4.80 (d, J=19.64 Hz, 2H), 7.51 (t, J=1.84 Hz, 1H), 7.56 (d, J=1.68 Hz, 2H), 7.62 (d, J=8.48 Hz, 2H), 7.92 (d, J=8.2 Hz, 2H). LC-MS (m/z): 553.1 (M−H). HPLC Purity: 99.03%.

Example 10

1-(3-{4-[5-(3,5-dichloro-phenyl)-5-trifluoromethyl-[1,4,2]dioxazol-3-yl]-phenyl}-3-fluoro-azetidin-1-yl)-2-methyl-propan-1-one

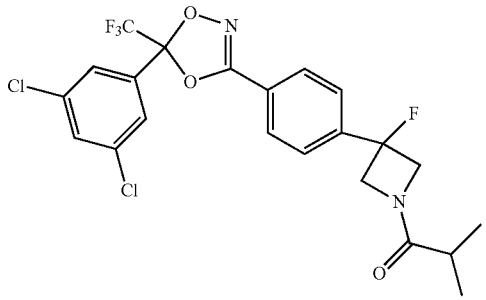 [SMILES: CC(C)C(=O)N1CC(F)(c2ccc(C3=NOC(c4cc(Cl)cc(Cl)c4)(C(F)(F)F)O3)cc2)C1]

This compound was prepared similarly to that of Example 9 except that isobutyric acid was used in place of methane sulfonyl acetic acid. Yield: 0.410 g (44.09%). $^1$H NMR (400 MHz, CDCl$_3$) δ: 1.14-1.17 (m, 6H), 2.46-2.53 (m, 1H), 4.31-4.52 (m, 3H), 4.59-4.67 (m, 1H), 7.51 (t, J=1.84 Hz, 1H), 7.56-7.58 (m, 4H), 7.91 (d, J=8.12 Hz, 2H). LC-MS (m/z): 505.2 (M+H). HPLC Purity: 99.54%.

Example 11

1-(3-fluoro-3-{4-[5-(3,4,5-trichloro-phenyl)-5-trifluoromethyl-[1,4,2]dioxazol-3-yl]-phenyl}-azetidin-1-yl)-2-methanesulfonyl-ethanone

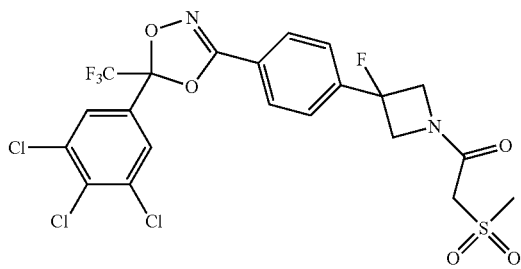 [SMILES: CS(=O)(=O)CC(=O)N1CC(F)(c2ccc(C3=NOC(c4cc(Cl)c(Cl)c(Cl)c4)(C(F)(F)F)O3)cc2)C1]

Step 1: Preparation of 3-fluoro-3-{4-[5-(3,4,5-trichloro-phenyl)-5-trifluoromethyl-[1,4,2]dioxazol-3-yl]-phenyl}-azetidine-1-carboxylic acid tert-butyl ester

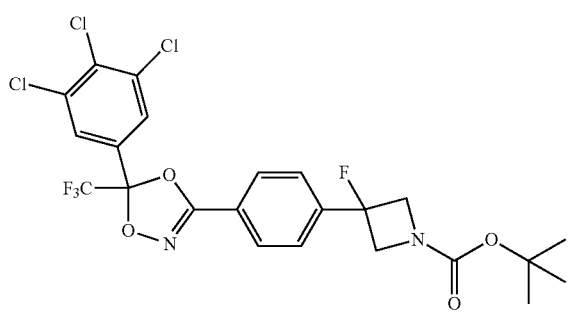

This compound was prepared similarly to Example 7 intermediate procedures except that 2,2,2-trifluoro-1-(3,4,5-trichloro-phenyl)ethanone was used in place of 1-(3,5-dichloro-4-fluoro-phenyl)-2,2,2-trifluoro-ethanone. Yield: 2.3 g (79.31%). $^1$H NMR (400 MHz, CDCl$_3$) δ: 1.46 (s, 9H), 4.16-4.24 (m, 2H), 4.38-4.46 (m, 2H), 7.58 (d, J=8.4 Hz, 2H), 7.71 (d, J=6.96 Hz, 2H), 7.88 (d, J=8.24 Hz, 2H), LC-MS (m/z): Low ionization.

Step 2: Preparation of trifluoroacetic acid salt of 3-[4-(3-fluoro-azetidin-3-yl)-phenyl]-5-(3,4,5-trichloro-phenyl)-5-trifluoromethyl-[1,4,2]dioxazole

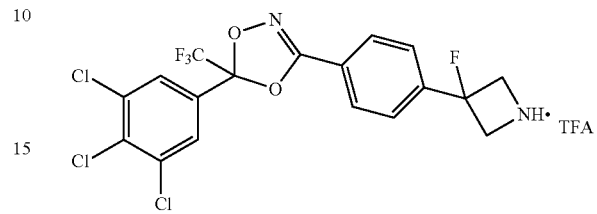

This compound was prepared similarly to Example 7 intermediate procedures except that 3-fluoro-3-{4-[5-(3,4,5-trichloro-phenyl)-5-trifluoromethyl-[1,4,2]dioxazol-3-yl]-phenyl}-azetidine-1-carboxylic acid tert-butyl ester was used in place of 3-{4-[5-(3,5-dichloro-4-fluoro-phenyl)-5-trifluoromethyl-[1,4,2]dioxazol-3-yl]-phenyl}-3-fluoro-azetidine-1-carboxylic acid tert-butyl ester. Yield: 2.3 g (Crude). Crude compound was used as such for next reaction. LC-MS (m/z): 469.2 (M+H).

Preparation of 1-(3-Fluoro-3-{4-[5-(3,4,5-trichloro-phenyl)-5-trifluoromethyl-[1,4,2]dioxazol-3-yl]-phenyl}-azetidin-1-yl)-2-methanesulfonyl-ethanone (Example 11)

This compound was prepared similarly to Example 7 except that trifluoroacetic acid salt of 3-[4-(3-fluoro-azetidin-3-yl)-phenyl]-5-(3,4,5-trichloro-phenyl)-5-trifluoromethyl-[1,4,2]dioxazole was used in place of trifluoroacetic acid salt of 5-(3,5-dichloro-4-fluoro-phenyl)-3-[4-(3-fluoro-azetidin-3-yl)-phenyl]-5-trifluoromethyl-[1,4,2]dioxazole. Yield: 0.6 g (41.67%). $^1$H NMR (400 MHz, CDCl$_3$) δ: 3.17 (s, 3H), 3.88 (s, 2H), 4.37-4.44 (m, 1H), 4.51-4.60 (m, 1H), 4.79 (d, J=19.64 Hz, 2H), 7.62 (d, J=8.48 Hz, 2H), 7.69 (s, 2H), 7.91 (d, J=8.2 Hz, 2H). LC-MS (m/z): 586.9 (M−H), HPLC Purity: 98.12%.

Example 12

1-(3-fluoro-3-{4-[5-(3,4,5-trichloro-phenyl)-5-trifluoromethyl-[1,4,2]dioxazol-3-yl]-phenyl}-azetidin-1-yl)-2-methyl-propan-1-one

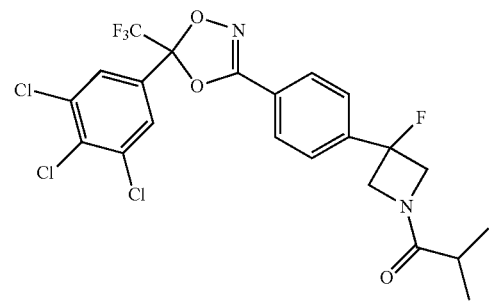 [SMILES: CC(C)C(=O)N1CC(F)(c2ccc(C3=NOC(c4cc(Cl)c(Cl)c(Cl)c4)(C(F)(F)F)O3)cc2)C1]

This compound was prepared similarly to that of Example 11 except that isobutyric acid was used in place of methane sulfonyl acetic acid. Yield: 0.476 g (36.06%). ¹H NMR (400 MHz, CDCl₃) δ: 1.15-1.18 (m, 6H), 2.46-2.53 (m, 1H), 4.31-4.52 (m, 3H), 4.59-4.67 (m, 1H), 7.57 (d, J=8.4 Hz, 2H), 7.70 (s, 2H), 7.90 (d, J=8.12 Hz, 2H). LC-MS (m/z): 539.1 (M+H), HPLC Purity: 98.87%.

Example 13

Hydrochloride salt of 1-(3-fluoro-3-{4-[5-(3,4,5-trichloro-phenyl)-5-trifluoromethyl-4,5-dihydro-1H-pyrazol-3-yl]-phenyl}-azetidin-1-yl)-2-methyl-propan-1-one

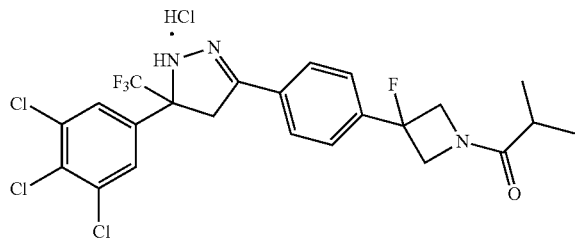

Step 1: Preparation of hydrochloride salt of (E/Z)-4,4,4-Trifluoro-1-[4-(3-fluoro-azetidin-3-yl)-phenyl]-3-(3,4,5-trichloro-phenyl)-but-2-en-1-one

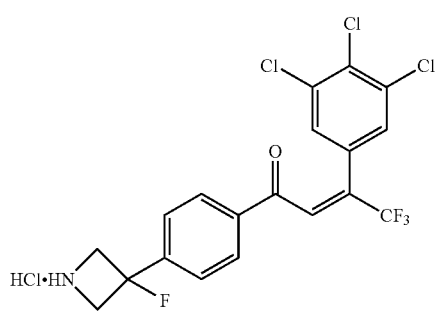

To 3-fluoro-3-{4-[(Z)-4,4,4-trifluoro-3-(3,4,5-trichloro-phenyl)-but-2-enoyl]-phenyl}-azetidine-1-carboxylic acid tert-butyl ester (1.9 g, 3.437 mmol, 1 eq.) was added methanolic HCl (20 mL) at 0° C. Resulting reaction mixture was stirred for 16 hours at room temperature. After consumption of starting material, reaction mixture was concentrated under reduced pressure to get yellow sticky mass. Yellow sticky mass was dissolved in chloroform (20 mL) and concentrated, this procedure was repeated twice to afford pale yellow solid (1.46 g, 94.87%). LC-MS (m/z): 451.9 (M+H).

Step 2: Preparation of (E/Z)-4,4,4-trifluoro-1-[4-(3-fluoro-1-isobutyryl-azetidin-3-yl)-phenyl]-3-(3,4,5-trichloro-phenyl)-but-2-en-1-one

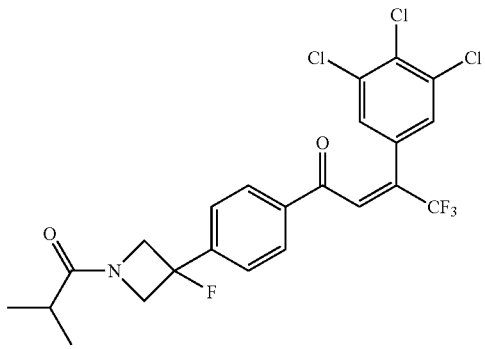 [SMILES: CC(C)C(=O)N1CC(F)(c2ccc(C(=O)/C=C(\c3cc(Cl)c(Cl)c(Cl)c3)C(F)(F)F)cc2)C1]

To the stirred solution of hydrochloride salt of (E/Z)-4,4,4-trifluoro-1-[4-(3-fluoro-azetidin-3-yl)-phenyl]-3-(3,4,5-trichloro-phenyl)-but-2-en-1 (1.4 g, 2.863 mmol, 1 eq) in DMF (15 mL) was added Et₃N (1.991 mL, 14.315 mmol, 5 eq) followed by addition of isobutyric acid (0.545 mL, 5.726 mmol. 2 eq), HOBt (0.387 g, 2.863 mmol, 1 eq) and EDC.HCl (0.82 g, 4.294 mmol, 1.5 eq) at room temperature. Resulting reaction mixture was stirred at room temperature for 16 hours. After consumption of starting material, reaction mixture was quenched with water (30 mL) and extracted with ethyl acetate (3×15 mL). Combined organic layers were washed with aq. sodium bicarbonate (2×25 mL), aqueous LiCl solution (2×25 mL) and brine (25 mL) and dried over sodium sulfate. Organic layer was concentrated in vacuo to get brown semi solid (Crude). Crude was purified by column chromatography using silica gel (100-200 mesh). Compound was eluted in 30% ethyl acetate in n-Hexane to get yellow sticky solid (0.5 g, 33.33%). ¹H NMR (400 MHz, CDCl₃, Mixture of E/Z isomer) δ: 1.15 (d, J=5.16 Hz, 6H), 2.46-2.53 (m, 1H), 4.29-4.51 (m, 3H), 4.58-4.66 (m, 1H), 7.28 (s, 2H), 7.41 (d, J=1.32 Hz, 1H), 7.54-7.57 (m, 2H), 7.88 (d, J=8.32 Hz, 2H), LC-MS (m/z): 523.7 (M+H).

Step 3: Preparation of 1-(3-fluoro-3-{4-[5-(3,4,5-trichloro-phenyl)-5-trifluoromethyl-4,5-dihydro-1H-pyrazol-3-yl]-phenyl}-azetidin-1-yl)-2-methyl-propan-1-one

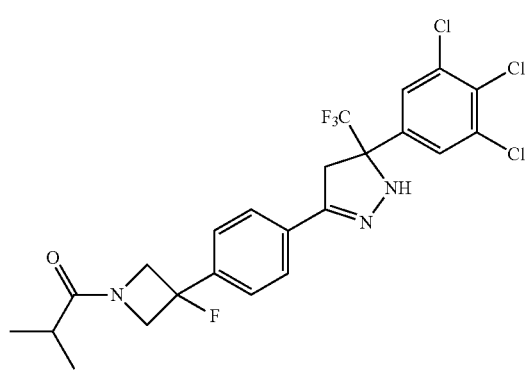

To the stirred solution of (E/Z)-4,4,4-trifluoro-1-[4-(3-fluoro-1-isobutyryl-azetidin-3-yl)-phenyl]-3-(3,4,5- trichloro-phenyl)-but-2-en-1-one (500 mg, 0.956 mmol, 1 eq) in ethanol (5 mL) was added hydrazine hydrate (0.056 mL, 1.148 mmol, 1.2 eq). Resulting reaction mixture was refluxed for 3 hours. After consumption of starting material, reaction mixture was concentrated to get crude compound, which was diluted with ethyl acetate (20 mL) and organic layer was washed with water (2×10 mL) and brine (20 mL). Organic layer was dried over sodium sulphate and evaporated to get title compound as yellow solid (500 mg, crude). Crude compound used as such for next step. LC-MS (m/z): 536.0 (M−H).

Step 4: Preparation of 3-[4-(3-fluoro-1-isobutyryl-azetidin-3-yl)-phenyl]-5-(3,4,5-trichloro-phenyl)-5-trifluoromethyl-4,5-dihydro-pyrazole-1-carboxylic acid tert-butyl ester

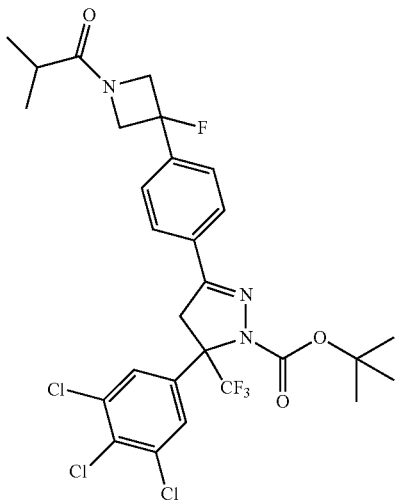 [SMILES: CC(C)C(=O)N1CC(F)(c2ccc(C3=NN(C(=O)OC(C)(C)C)C(c4cc(Cl)c(Cl)c(Cl)c4)(C(F)(F)F)C3)cc2)C1]

To the stirred solution of 1-(3-fluoro-3-{4-[5-(3,4,5-trichloro-phenyl)-5-trifluoromethyl-4,5-dihydro-1H-pyrazol-3-yl]-phenyl}-azetidin-1-yl)-2-methyl-propan-1-one (260 mg, 0.484 mmol, 1 eq) in DCM (3 mL) was added Et$_3$N (0.148 mL, 1.066 mmol, 2.2 eq.) followed by addition of DMAP (29.58 mg, 0.242 mmol, 0.5 eq), Boc.anhydride (0.222 mL, 0.969 mmol, 2 eq). Resulting reaction mixture was stirred for 12 hours at room temperature in nitrogen atmosphere. After consumption of starting material reaction mixture diluted with ethyl acetate (20 mL) and washed with water (2×20 mL) and brine (20 mL). Organic layer dried over sodium sulphate and evaporated to get as yellow solid (crude). Crude compound was purified by column chromatography (100-200 mesh). title compound eluted in 25% ethyl acetate in hexane (0.250 g, 81.04%). $^1$H NMR (400 MHz, CDCl$_3$) δ: 1.13-1.17 (m, 6H), 1.31 (bs, 9H), 2.46-2.53 (m, 1H), 3.55 (d, J=17.56 Hz, 1H), 4.05 (d, J=18.36 Hz, 1H), 4.31-4.50 (m, 3H), 4.50-4.63 (m, 1H), 7.40 (s, 2H), 7.49 (d, J=8.44 Hz, 2H), 7.78 (d, J=8.2 Hz, 2H), LC-MS (m/z): 636.2 (M−H).

Preparation of hydrochloride salt of 1-(3-fluoro-3-{4-[5-(3,4,5-trichloro-phenyl)-5-trifluoromethyl-4,5-dihydro-1H-pyrazol-3-yl]-phenyl}-azetidin-1-yl)-2-methyl-propan-1-one (Example 13)

To the stirred solution of 3-[4-(3-fluoro-1-isobutyryl-azetidin-3-yl)-phenyl]-5-(3,4,5-trichloro-phenyl)-5-trifluorom-ethyl-4,5-dihydro-pyrazole-1-carboxylic acid tert-butyl ester (250 mg, 0.364 mmol, 1 eq) in dioxane (1 mL) was purged HCl gas for 30 minutes at 0° C. and stirred for 30 minutes at room temperature. After consumption of starting material, reaction mixture reaction mixture was concentrated in vacuo to get orange semisolid (150 mg, crude). Crude was triturated with chloroform:hexane (0.5 mL: 4 mL) to afford title compound as off white solid (0.11 g, 56.31%). $^1$H NMR (400 MHz, CDCl$_3$) δ: 1.16 (t, J=6.24 Hz, 6H), 2.51 (bs, 1H), 3.38 (d, J=17.16 Hz, 1H), 3.88 (d, J=17.16 Hz, 1H), 4.42-4.61 (m, 4H), 6.44 (s, 1H), 7.47 (d, J=8.12 Hz, 2H), 7.56 (s, 2H), 7.69 (d, J=8.0 Hz, 2H). LC-MS (m/z): 536.1 (M+H). HPLC Purity: 96.38%.

Example 14

Hydrochloride salt of 1-(3-{4-[5-(3,5-dichloro-4-fluoro-phenyl)-5-trifluoromethyl-4,5-dihydro-1H-pyrazol-3-yl]-phenyl}-3-fluoro-azetidin-1-yl)-2-methyl-propan-1-one

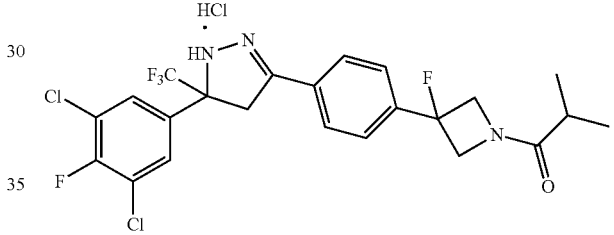

Step 1: Preparation of hydrochloride salt of (E/Z)-3-(3,5-dichloro-4-fluoro-phenyl)-4,4,4-trifluoro-1-[4-(3-fluoro-azetidin-3-yl)-phenyl]-but-2-en-1-one

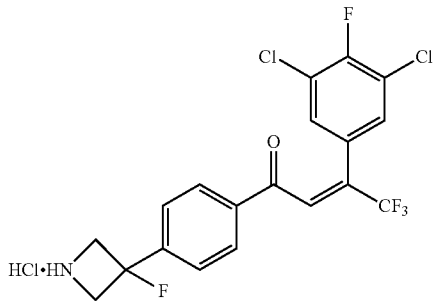

This compound was prepared similarly to Example 13 intermediate procedures except that 3-{4-[(E/Z)-3-(3,5-dichloro-4-fluoro-phenyl)-4,4,4-trifluoro-but-2-enoyl]-phenyl}-3-fluoro-azetidine-1-carboxylic acid tert-butyl ester was used in place of 3-fluoro-3-{4-[(Z)-4,4,4-trifluoro-3-(3,4,5-trichloro-phenyl)-but-2-enoyl]-phenyl}-azetidine-1-carboxylic acid tert-butyl ester. Yield: 4.0 g (Crude). Crude compound was used as such for the next reaction.

Step 2: Preparation of (E/Z)-3-(3,5-dichloro-4-fluoro-phenyl)-4,4,4-trifluoro-1-[4-(3-fluoro-1-isobutyryl-azetidin-3-yl)-phenyl]-but-2-en-1-one

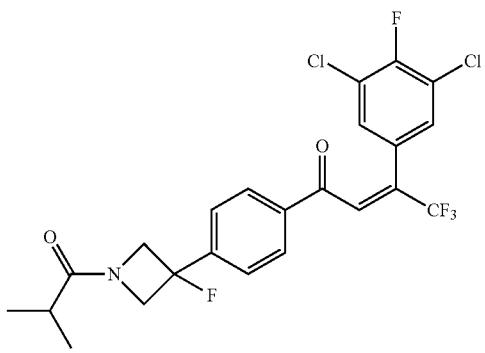

This compound was prepared similarly to Example 13 intermediate procedures except that the hydrochloride salt of (E/Z)-3-(3,5-dichloro-4-fluoro-phenyl)-4,4,4-trifluoro-1-[4-(3-fluoro-azetidin-3-yl)-phenyl]-but-2-en-1-one was used in place of hydrochloride salt of (E/Z)-4,4,4-trifluoro-1-[4-(3-fluoro-azetidin-3-yl)-phenyl]-3-(3,4,5-trichloro-phenyl)-but-2-en-1-one. Yield: 1.4 g (60.34%). $^1$H NMR (400 MHz, CDCl$_3$) δ: 1.15-1.18 (m, 6H), 2.46-2.52 (m, 1H), 4.32-4.48 (m, 3H), 4.58-4.64 (m, 1H), 7.22 (d, J=12 Hz, 2H), 7.40 (d, J=1.16 Hz, 1H), 7.56 (d, J=8.44 Hz, 2H), 7.88 (d, J=8.16 Hz, 2H). LC-MS (m/z): 503.9 (M−H).

Step 3: Preparation of 1-(3-{4-[5-(3,5-dichloro-4-fluoro-phenyl)-5-trifluoromethyl-4,5-dihydro-1H-pyrazol-3-yl]-phenyl}-3-fluoro-azetidin-1-yl)-2-methyl-propan-1-one

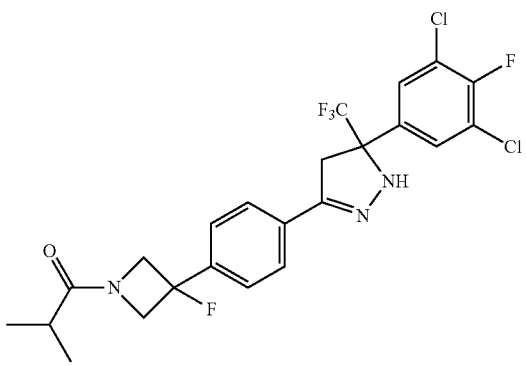 [SMILES: CC(C)C(=O)N1CC(F)(c2ccc(C3=NNC(c4cc(Cl)c(F)c(Cl)c4)(C(F)(F)F)C3)cc2)C1]

This compound was prepared similarly to Example 13 intermediate procedures except that (E/Z)-3-(3,5-dichloro-4-fluoro-phenyl)-4,4,4-trifluoro-1-[4-(3-fluoro-1-isobutyryl-azetidin-3-yl)-phenyl]-but-2-en-1-one was used in place of (E/Z)-4,4,4-trifluoro-1-[4-(3-fluoro-1-isobutyryl-azetidin-3-yl)-phenyl]-3-(3,4,5-trichloro-phenyl)-but-2-en-1-one. Yield: 1.4 g (Crude). Crude compound was used as such for the next reaction. $^1$H NMR (400 MHz, CDCl$_3$) δ: 1.15 (t, J=6.88 Hz, 6H), 2.46-2.51 (m, 1H), 3.38 (d, J=17.04 Hz, 1H), 3.88 (d, J=17.16 Hz, 1H), 4.35-4.46 (m, 3H), 4.56-4.62 (m, 1H), 6.42 (s, 1H), 7.47 (d, J=8.4 Hz, 2H), 7.50 (d, J=6.04 Hz, 2H), 7.69 (d, J=8.12 Hz, 2H), LC-MS (m/z): 518.2 (M−H).

Step 4: Preparation of 5-(3,5-dichloro-4-fluoro-phenyl)-3-[4-(3-fluoro-1-isobutyryl-azetidin-3-yl)-phenyl]-5-trifluoromethyl-4,5-dihydro-pyrazole-1-carboxylic acid tert-butyl ester

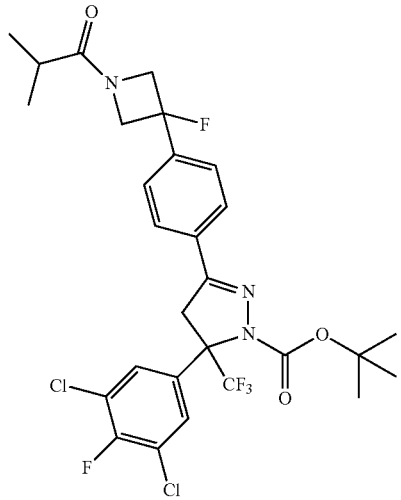 [SMILES: CC(C)C(=O)N1CC(F)(c2ccc(C3=NN(C(=O)OC(C)(C)C)C(c4cc(Cl)c(F)c(Cl)c4)(C(F)(F)F)C3)cc2)C1]

This compound was prepared similarly to Example 13 intermediate procedures except that 1-(3-{4-[5-(3,5-dichloro-4-fluoro-phenyl)-5-trifluoromethyl-4,5-dihydro-1H-pyrazol-3-yl]-phenyl}-3-fluoro-azetidin-1-yl)-2-methyl-propan-1-one was used in place of 1-(3-fluoro-3-{4-[5-(3,4,5-trichloro-phenyl)-5-trifluoromethyl-4,5-dihydro-1H-pyrazol-3-yl]-phenyl}-azetidin-1-yl)-2-methyl-propan-1-one. Yield: 1.4 g (83.83%). LC-MS (m/z): 618.3 (M−H).

Preparation of hydrochloride salt of 1-(3-{4-[5-(3,5-dichloro-4-fluoro-phenyl)-5-trifluoromethyl-4,5-dihydro-1H-pyrazol-3-yl]-phenyl}-3-fluoro-azetidin-1-yl)-2-methyl-propan-1-one (Example 14)

This compound was prepared similarly to that of Example 13 except that 5-(3,5-dichloro-4-fluoro-phenyl)-3-[4-(3-fluoro-1-isobutyryl-azetidin-3-yl)-phenyl]-5-trifluoromethyl-4,5-dihydro-pyrazole-1-carboxylic acid tert-butyl ester was used in place of 3-[4-(3-fluoro-1-isobutyryl-azetidin-3-yl)-phenyl]-5-(3,4,5-trichloro-phenyl)-5-trifluoromethyl-4,5-dihydro-pyrazole-1-carboxylic acid tert-butyl ester. Yield: 0.700 g (59.83%). $^1$H NMR (400 MHz, DMSO) δ: 0.99-1.03 (m, 6H), 2.52-2.57 (m, 1H), 3.76-3.88 (m, 2H), 4.22-4.34 (m, 2H), 4.58-4.69 (m, 2H), 7.55 (d, J=8.32 Hz, 2H), 7.71 (d, J=8.12 Hz, 2H), 7.85 (d, J=6.24 Hz, 2H), 8.93 (s, 1H). LC-MS (m/z): 518.0 (M−H). HPLC Purity: 97.80%.

Example 15

1-(3-fluoro-3-(4-(5-(3,4,5-trichlorophenyl)-5-(trifluoromethyl)-4,5-dihydro-1H-pyrazol-3-yl)phenyl)azetidin-1-yl)-2-(methylsulfonyl)ethanone

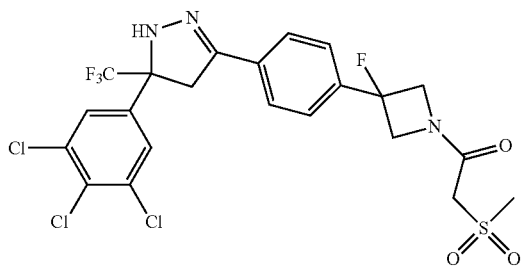 [SMILES: CS(=O)(=O)CC(=O)N1CC(F)(c2ccc(C3=NNC(c4cc(Cl)c(Cl)c(Cl)c4)(C(F)(F)F)C3)cc2)C1]

Step 1: Preparation of 3-(4-acetyl-phenyl)-3-fluoro-azetidine-1-carboxylic acid tert-butyl ester

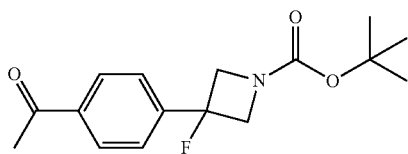 [SMILES: CC(=O)c1ccc(C2(F)CN(C(=O)OC(C)(C)C)C2)cc1]

This intermediate was prepared as described above in Step 1 of Example 1.

Step 2: Preparation of 3-fluoro-3-{4-[(E/Z)-4,4,4-trifluoro-3-(3,4,5-trichloro-phenyl)-but-2-enoyl]-phenyl}-azetidine-1-carboxylic acid tert-butyl ester

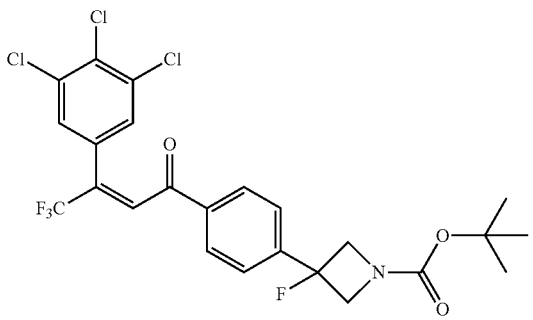

In 100 mL two neck RBF equipped with Dean-stark apparatus, to the stirred solution of 3-(4-acetyl-phenyl)-3-fluoro-azetidine-1-carboxylic acid tert-butyl ester (1.5 g, 5.119 mmol, 1 eq) in toluene (10 mL) and trifluoromethyl benzene (10 mL) was added 1-(3,4,5-trichloro-phenyl)-2,2,2-trifluoro-ethanone (1.562 g, 5.631 mmol, 1.1 eq) and $Cs_2CO_3$ (0.166 g, 0.512 mmol, 0.1 eq) at room temperature. Resulting reaction mixture was stirred at 140° C. for 16 hours. After complete consumption of starting material, reaction mixture cooled to room temperature and was diluted with tert-butyl-methyl ether (50 mL) and filtered through bed of celite. Filtrate was concentrated in vacuo to get crude compound as brown sticky oil (3 g, crude). Crude compound was purified by column chromatography on silica gel using 230-400 mesh. Desired compound was eluted in 7% ethyl acetate in n-hexane to give title compound as light yellow solid (2.4 g, 84.81%). $^1$H NMR (400 MHz, $CDCl_3$) δ:1.47 (s, 9H), 4.15-4.22 (m, 2H), 4.37-4.46 (m, 2H), 7.28 (s, 2H), 7.41 (d, J=1.36 Hz, 1H), 7.56-7.58 (m, 2H), 7.87 (d, J=8.16 Hz, 2H). LC-MS (m/z): 551.7 (M−H).

Step 3: Preparation of hydrochloride salt of (E/Z)-4,4,4-trifluoro-1-[4-(3-fluoro-azetidin-3-yl)-phenyl]-3-(3,4,5-trichloro-phenyl)-but-2-en-1-one

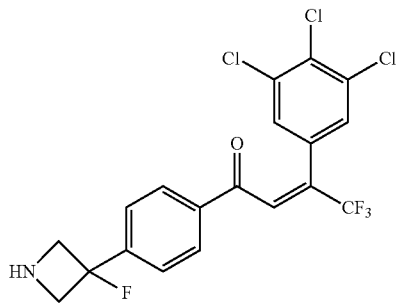 [SMILES: O=C(/C=C(\c1cc(Cl)c(Cl)c(Cl)c1)C(F)(F)F)c1ccc(C2(F)CNC2)cc1]

To the stirred solution of 3-fluoro-3-{4-[(E/Z)-4,4,4-trifluoro-3-(3,4,5-trichloro-phenyl)-but-2-enoyl]-phenyl}-azetidine-1-carboxylic acid tert-butyl ester (2.4 g, 4.633 mmol, 1 eq) in methanolic HCl (25 mL) at 0° C. Resulting reaction mixture was stirred at room temperature for 16 hours. Reaction was monitored by TLC. After consumption of starting material, reaction mixture was concentrated to get yellow sticky mass, which was redissolved in chloroform (50 mL) and chloroform was stripped out. This procedure was repeated twice to get title compound as pale yellow solid (2.4 g, Crude). Crude compound was used as such for next reaction. LC-MS (m/z): 453.9 (M+H).

Step 4: Preparation of (E/Z)-4,4,4-trifluoro-1-{4-[3-fluoro-1-(2-methanesulfonyl-acetyl)-azetidin-3-yl]-phenyl}-3-(3,4,5-trichloro-phenyl)-but-2-en-1-one

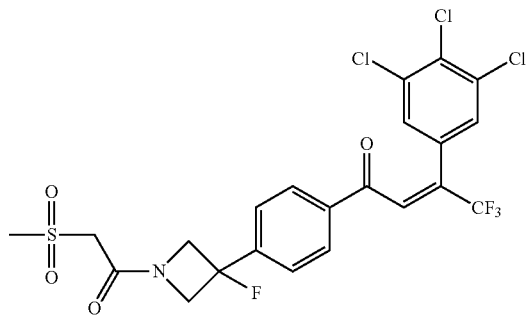

To the stirred solution of hydrochloride salt of (E/Z)-4,4,4-trifluoro-1-[4-(3-fluoro-azetidin-3-yl)-phenyl]-3-(3,4,5-trichloro-phenyl)-but-2-en-1-one (2.4 g, 5.302 mmol, 1 eq) in DMF (25 mL) was added $Et_3N$ (3.688 mL, 26.509 mmol, 5 eq) followed by addition of methanesulfonyl-acetic acid (1.463 g, 10.604 mmol, 2 eq), HOBt (0.716 g, 5.302 mmol, 1 eq) and EDC.HCl (1.29 g, 7.953 mmol, 1.5 eq) at room temperature. Resulting reaction mixture was stirred at room temperature for 16 hours. After consumption of starting material, reaction mixture was quenched with water (30 mL) and extracted with ethyl acetate (3×25 mL). Combined organic layers were washed with aq. sodium bicarbonate (2×25 mL), aq. LiCl solution (2×25 mL) and brine (25 mL) and dried over sodium sulfate. Organic layer was concentrated in vacuo to get brown sticky oil (Crude). Purification was done by Combiflash chromatography using 40 g Redisep column. Compound was eluted in 40% ethyl acetate in n-Hexane to get title compound as brown sticky oil (0.720 g, 23.68%). LC-MS (m/z): 569.9 (M−H).

Preparation of 1-(3-fluoro-3-{4-[5-(3,4,5-trichloro-phenyl)-5-trifluoromethyl-4,5-dihydro-1H-pyrazol-3-yl]-phenyl}-azetidin-1-yl)-2-methane sulfonyl-ethanone (Example 15)

To the stirred solution of (E/Z)-4,4,4-trifluoro-1-{4-[3-fluoro-1-(2-methanesulfonyl-acetyl)-azetidin-3-yl]-phenyl}-3-(3,4,5-trichloro-phenyl)-but-2-en-1-one (0.5 g, 0.874 mmol, 1 eq) in ethanol (5 mL) was added hydrazine (1.0 M solution in THF, 1.31 mL, 1.311 mmol, 1.5 eq). Resulting reaction mixture was refluxed for 2 hours under nitrogen atmosphere. After consumption of starting material, the reaction mixture was concentrated to get crude compound, dissolved in ethyl acetate (1 mL) and adsorb on 100-200 mesh silica. Crude compound purified by Combiflash chromatography using 40 g Redisep column.

Desired compound was eluted in 55% ethyl acetate in hexane to afford title compound as off white solid (0.170 g, 33.14%). $^1$H NMR (400 MHz, DMSO-d6) δ: 3.12 (s, 3H), 3.77-3.90 (m, 2H), 4.26 (s, 2H), 4.36-4.42 (m, 2H), 4.75 (d, J=21.52 Hz, 2H), 7.55 (d, J=8.24 Hz, 2H), 7.72 (d, J=8.04 Hz, 2H), 7.89 (s, 2H), 8.96 (s, 1H), LC-MS (m/z): 585.8 (M−H). HPLC purity: 93.27%.

Example 16

1-(3-(4-(5-(3,5-dichlorophenyl)-5-(trifluoromethyl)-4,5-dihydro-1H-pyrazol-3-yl)phenyl)-3-fluoroazetidin-1-yl)-2-(methylsulfonyl)ethanone

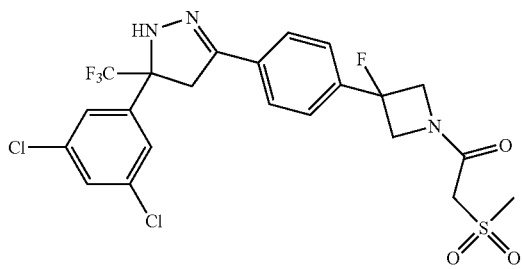 [SMILES: CS(=O)(=O)CC(=O)N1CC(F)(c2ccc(C3=NNC(c4cc(Cl)cc(Cl)c4)(C(F)(F)F)C3)cc2)C1]

Step 1: Preparation of 3-{4-[(E/Z)-3-(3,5-dichloro-phenyl)-4,4,4-trifluoro-but-2-enoyl]-phenyl}-3-fluoro-azetidine-1-carboxylic acid tert-butyl ester

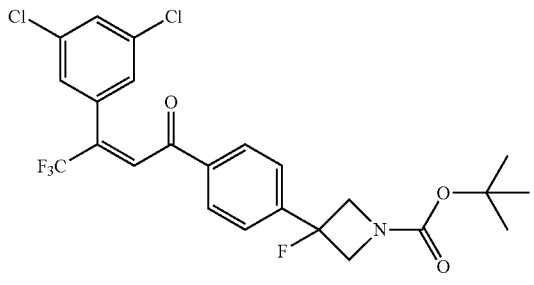 [SMILES: CC(C)(C)OC(=O)N1CC(F)(c2ccc(C(=O)/C=C(\c3cc(Cl)cc(Cl)c3)C(F)(F)F)cc2)C1]

This compound was prepared similarly to that in Example 15 except that 1-(3,5-dichloro-phenyl)-2,2,2-trifluoro-ethanone was used in place of 1-(3,4,5-trichloro-phenyl)-2,2,2-trifluoro-ethanone. Yield: 3.6 g (67.92%). $^1$H NMR (400 MHz, CDCl$_3$) δ: 1.47 (s, 9H), 4.14-4.22 (m, 2H), 4.37-4.45 (m, 2H), 7.14 (d, J=1.68 Hz, 2H), 7.31 (t, J=2.82 Hz, 1H), 7.36-7.39 (m, 1H), 7.56 (d, J=14.72 Hz, 2H), 7.86 (d, J=1.36 Hz, 2H), LC-MS (m/z): 516.1 (M−H).

Step 2: Preparation of hydrochloride salt of (E/Z)-3-(3,5-dichloro-phenyl)-4,4,4-trifluoro-1-[4-(3-fluoro-azetidin-3-yl)-phenyl]-but-2-en-1-one

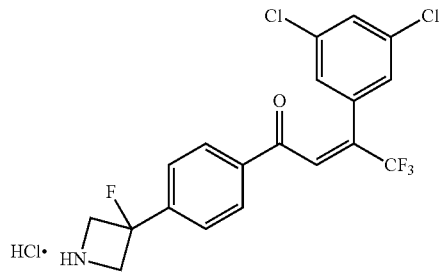 [SMILES: O=C(/C=C(\c1cc(Cl)cc(Cl)c1)C(F)(F)F)c1ccc(C2(F)CNC2)cc1]

This compound was prepared similarly to that in Example 15 except that 3-{4-[(E/Z)-3-(3,5-dichloro-phenyl)-4,4,4-trifluoro-but-2-enoyl]-phenyl}-3-fluoro-azetidine-1-carboxylic acid tert-butyl ester was used in place of 3-fluoro-3-{4-[(E/Z)-4,4,4-trifluoro-3-(3,4,5-trichloro-phenyl)-but-2-enoyl]-phenyl}-azetidine-1-carboxylic acid tert-butyl ester. Yield: 3.6 g (Crude). Crude compound was used as such for the next reaction. LC-MS (m/z): 417.7 (M+H).

Step 3: Preparation of (E/Z)-3-(3,5-dichloro-phenyl)-4,4,4-trifluoro-1-{4-[3-fluoro-1-(2-methanesulfonyl-acetyl)azetidin-3-yl]-phenyl}-but-2-en-1-one

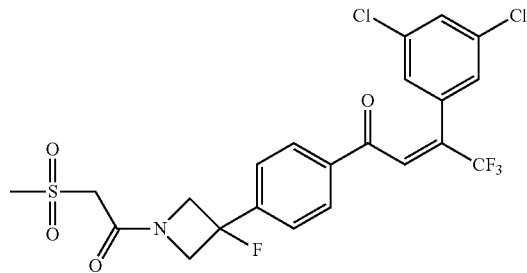 [SMILES: CS(=O)(=O)CC(=O)N1CC(F)(c2ccc(C(=O)/C=C(\c3cc(Cl)cc(Cl)c3)C(F)(F)F)cc2)C1]

This compound was prepared similarly to that in Example 15 except that the hydrochloride salt of (E/Z)-3-(3,5- dichloro-phenyl)-4,4,4-trifluoro-1-[4-(3-fluoro-azetidin-3-yl)-phenyl]-but-2-en-1-one was used in place of hydrochloride salt of (E/Z)-4,4,4-trifluoro-1-[4-(3-fluoro-azetidin-3-yl)-phenyl]-3-(3,4,5-trichloro-phenyl)-but-2-en-1-one. Yield: 1 g (43.1%). $^1$H NMR (400 MHz, CDCl$_3$) δ: 3.17 (s, 3H), 3.88 (s, 2H), 4.32-4.44 (m, 1H), 4.47-4.59 (m, 1H), 4.73-4.86 (m, 2H), 7.14 (d, J=1.56 Hz, 1H), 7.32 (t, J=2.7 Hz, 1H), 7.38 (d, J=1.2 Hz, 1H), 7.59 (d, J=8.4 Hz, 2H), 7.89 (d, J=8.32 Hz, 2H), LC-MS (m/z): 535.8 (M−H).

Preparation of 1-(3-{4-[5-(3,5-dichloro-phenyl)-5-trifluoromethyl-4,5-dihydro-1H-pyrazol-3-yl]-phenyl}-3-fluoro-azetidin-1-yl)-2-methanesulfonyl-ethanone (Example 16)

This compound was prepared similarly to that in Example 15 except that (E/Z)-3-(3,5-dichloro-phenyl)-4,4,4-trifluoro-1-{4-[3-fluoro-1-(2-methanesulfonyl-acetyl)-azetidin-3-yl]-phenyl}-but-2-en-1-one was used in place of (E/Z)-4,4,4-trifluoro-1-{4-[3-fluoro-1-(2-methanesulfonyl-acetyl)-azetidin-3-yl]-phenyl}-3-(3,4,5-trichloro-phenyl)-but-2-en-1-one. Yield: 0.150 g (60.87%). $^1$H NMR (400 MHz, DMSO) δ: 3.12 (s, 3H), 3.74-3.90 (m, 2H), 4.26 (s, 2H), 4.33-4.42 (m, 2H), 4.74 (d, J=21.52 Hz, 2H), 7.55 (d, J=8.24 Hz, 1H), 7.67 (d, J=1.52 Hz, 1H), 7.71-7.74 (m, 3H), 8.95 (s, 1H), LC-MS (m/z): 549.7 (M−H), HPLC purity: 98.71%.

Example 17

1-(3-(4-(5-(3,5-dichlorophenyl)-5-(trifluoromethyl)-4,5-dihydro-1H-pyrazol-3-yl)phenyl)-3-fluoroazetidin-1-yl)-2-methylpropan-1-one

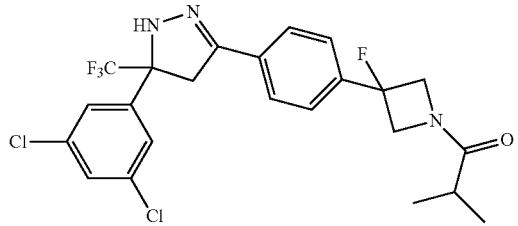 [SMILES: CC(C)C(=O)N1CC(F)(c2ccc(C3=NNC(c4cc(Cl)cc(Cl)c4)(C(F)(F)F)C3)cc2)C1]

Step 1: Preparation of (E/Z)-3-(3,5-dichloro-phenyl)-4,4,4-trifluoro-1-[4-(3-fluoro-1-isobutyryl-azetidin-3-yl)-phenyl]-but-2-en-1-one

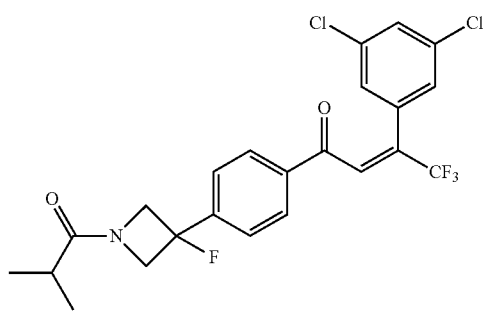 [SMILES: CC(C)C(=O)N1CC(F)(c2ccc(C(=O)/C=C(\c3cc(Cl)cc(Cl)c3)C(F)(F)F)cc2)C1]

This compound was prepared similarly to that in Example 16 except that isobutyric acid was used in place of methane-sulfonyl-acetic acid. Yield: 1.0 g (47.62%). $^1$H NMR (400 MHz, CDCl$_3$) δ: 1.15-1.19 (m, 6H), 2.46-2.52 (m, 1H), 4.27-4.45 (m, 3H), 4.46-4.58 (m, 1H), 7.14 (d, J=1.56 Hz, 2H), 7.30-7.32 (m, 1H), 7.38 (d, J=1.12 Hz, 1H), 7.55 (d, J=8.4 Hz, 2H), 7.88 (d, J=8.48 Hz, 2H), LC-MS (m/z): 485.7 (M−H).

Preparation of 1-(3-{4-[5-(3,5-dichloro-phenyl)-5-trifluoromethyl-4,5-dihydro-1H-pyrazol-3-yl]-phenyl}-3-fluoro-azetidin-1-yl)-2-methyl-propan-1-one (Example 17)

This compound was prepared similarly to Example 16 except that (E/Z)-3-(3,5-dichloro-phenyl)-4,4,4-trifluoro-1-[4-(3-fluoro-1-isobutyryl-azetidin-3-yl)-phenyl]-but-2-en-1-one was used in place of (E/Z)-3-(3,5-dichloro-phenyl)-4,4,4-trifluoro-1-{4-[3-fluoro-1-(2-methanesulfonyl-acetyl)-azetidin-3-yl]-phenyl}-but-2-en-1-one. Yield: 0.290 g (70.43%). $^1$H NMR (400 MHz, DMSO) δ: 0.99-1.03 (m, 6H), 2.52-2.56 (m, 1H), 3.75 (d, J=17.84 Hz, 1H), 3.87 (d, J=17.8 Hz, 1H), 4.74 (d, J=21.52 Hz, 2H), 4.25-4.31 (m, 2H), 4.61-4.67 (m, 2H), 7.55 (d, J=8.16 Hz, 2H), 7.67 (d, J=1.6 Hz, 2H), 7.71-7.73 (m, 3H), 8.94 (s, 1H), LC-MS (m/z): 499.8 (M−H), HPLC purity: 98.98%.

Example 18

1-(3-(4-(5-(3,5-dichloro-4-fluorophenyl)-5-(trifluoromethyl)-4,5-dihydro-1H-pyrazol-3-yl)phenyl)-3-fluoroazetidin-1-yl)-2-(methylsulfonyl)ethanone

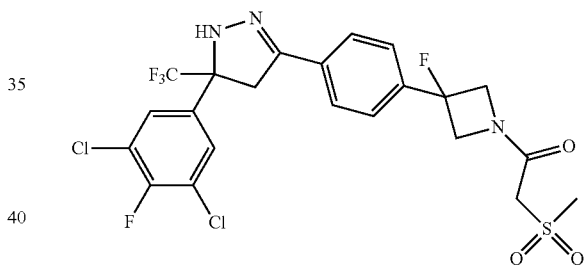

Step 1: Preparation of 3-{4-[(E/Z)-3-(3,5-dichloro-4-fluoro-phenyl)-4,4,4-trifluoro-but-2-enoyl]-phenyl}-3-fluoro-azetidine-1-carboxylic acid tert-butyl ester

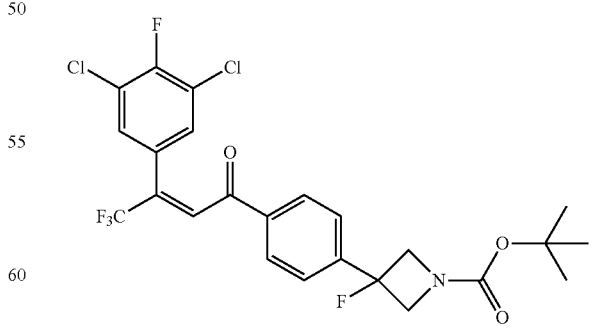

This compound was prepared similarly to that in Example 15 except that 1-(3,5-dichloro-4-fluoro-phenyl)-2,2,2-trifluoro-ethanone was used in place of 1-(3,4,5-trichloro-phenyl)-2,2,2-trifluoro-ethanone. Yield: 3.2 g (87.43%). $^1$H NMR (400 MHz, CDCl$_3$) δ: 1.46 (s, 9H), 4.15-4.25 (m, 2H), 4.37-4.48 (m, 2H), 7.23 (d, J=6.12 Hz, 2H), 7.40 (d, J=1.36 Hz, 1H), 7.57 (d, J=8.4 Hz, 2H), 7.87 (d, J=8.16 Hz, 2H). LC-MS (m/z): 533.9 (M–H).

Step 2: Preparation of hydrochloride salt of (E/Z)-3-(3,5-dichloro-4-fluoro-phenyl)-4,4,4-trifluoro-1-[4-(3-fluoro-azetidin-3-yl)-phenyl]-but-2-en-1-one

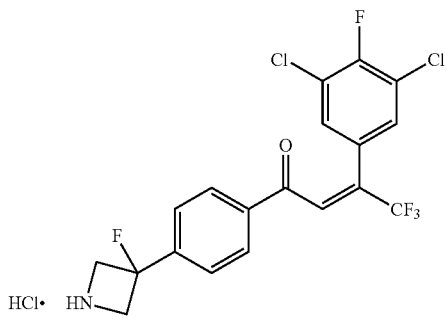 [SMILES: O=C(/C=C(\c1cc(Cl)c(F)c(Cl)c1)C(F)(F)F)c1ccc(C2(F)CNC2)cc1]

This compound was prepared similarly to that in Example 15 except that 3-{4-[(E/Z)-3-(3,5-dichloro-4-fluoro-phenyl)-4,4,4-trifluoro-but-2-enoyl]-phenyl}-3-fluoro-azetidine-1-carboxylic acid tert-butyl ester was used in place of 3-fluoro-3-{4-[(E/Z)-4,4,4-trifluoro-3-(3,4,5-trichloro-phenyl)-but-2-enoyl]-phenyl}-azetidine-1-carboxylic acid tert-butyl ester. Yield: 3.2 g (Crude). Crude compound was used as such for the next reaction. LC-MS (m/z): 435.6 (M+H).

Step 3: Preparation of (E/Z)-3-(3,5-dichloro-4-fluoro-phenyl)-4,4,4-trifluoro-1-{4-[3-fluoro-1-(2-methanesulfonyl-acetyl)-azetidin-3-yl]-phenyl}-but-2-en-1-one

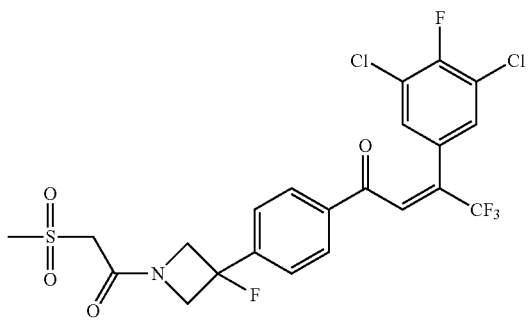 [SMILES: CS(=O)(=O)CC(=O)N1CC(F)(c2ccc(C(=O)/C=C(\c3cc(Cl)c(F)c(Cl)c3)C(F)(F)F)cc2)C1]

This compound was prepared similarly to that in Example 15 except that the hydrochloride salt of (E/Z)-3-(3,5-dichloro-4-fluoro-phenyl)-4,4,4-trifluoro-1-[4-(3-fluoro-azetidin-3-yl)-phenyl]-but-2-en-1-one was used in place of hydrochloride salt of (E/Z)-4,4,4-trifluoro-1-[4-(3-fluoro-azetidin-3-yl)-phenyl]-3-(3,4,5-trichloro-phenyl)-but-2-en-1-one. Yield: 1 g (31.35%). $^1$H NMR (400 MHz, CDCl$_3$) δ: 3.17 (s, 3H), 3.87 (s, 2H), 4.35-4.43 (m, 1H), 4.51-4.59 (m, 1H), 4.75-4.83 (m, 1H), 7.23 (d, J=6.08 Hz, 2H), 7.40 (d, J=1.36 Hz, 1H), 7.61 (d, J=8.48 Hz, 2H), 7.90 (d, J=8.16 Hz, 2H). LC-MS (m/z): 553.8 (M–H).

Preparation of 1-(3-{4-[5-(3,5-dichloro-4-fluoro-phenyl)-5-trifluoromethyl-4,5-dihydro-1H-pyrazol-3-yl]-phenyl}-3-fluoro-azetidin-1-yl)-2-methanesulfonyl-ethanone (Example 18)

This compound was prepared similarly to that of Example 15 except that (E/Z)-3-(3,5-dichloro-4-fluoro-phenyl)-4,4,4-trifluoro-1-{4-[3-fluoro-1-(2-methanesulfonyl-acetyl)-azetidin-3-yl]-phenyl}-but-2-en-1-one was used in place of (E/Z)-4,4,4-trifluoro-1-{4-[3-fluoro-1-(2-methanesulfonyl-acetyl)-azetidin-3-yl]-phenyl}-3-(3,4,5-trichloro-phenyl)-but-2-en-1-one. Yield: 0.090 g (39.81%). $^1$H NMR (400 MHz, DMSO-d6) δ: 3.12 (s, 3H), 3.81-3.84 (m, 2H), 4.26 (s, 2H), 4.39 (d, J=21.4 Hz, 2H), 4.74 (d, J=21.72 Hz, 2H), 7.55 (d, J=6.88 Hz, 2H), 7.71 (d, J=7.12 Hz, 2H), 7.85 (bs, 2H), 8.94 (s, 1H). LC-MS (m/z): 569.8 (M+H). HPLC purity: 97.69%.

In addition to the previously prepared examples, the additional Examples as described in Table 1 (A1-A139), Table 2 (B1-B139), and Table 3 (C1-C139) can all be prepared from each of Formula (2d1), (2e1), (2f1), (3d1), (3e1), (3f1), (4d1), (4e1), (4f1), (5d1), (5e1), (5f1), (6d1), (6e1), and (6f1), shown below, according to the schemes and procedures presented herein. For example, a compound of Formula (2d1), Table 1, Example A1, is the compound 1-(3-fluoro-3-(4-(3-(3,4,5-trichlorophenyl)-3-(trifluoromethyl)-3,4-dihydro-2H-pyrrol-5-yl)phenyl)azetidin-1-yl)ethanone; similarly the compound of Formula (5e1), Table 1, Example A62, is the compound 2-cyclopropyl-1-(3-(5-(5-(3,5-dichloro-4-fluorophenyl)-5-(trifluoromethyl)-1,4,2-dioxazol-3-yl)pyridin-2-yl)-3-fluoroazetidin-1-yl)ethanone; similarly the compound of Formula (2d1), Table 1, Example A99, is the compound 1-(3-(4-(3-(3-chloro-5-(trifluoromethyl)phenyl)-3-(trifluoromethyl)-3,4-dihydro-2H-pyrrol-5-yl)phenyl)-3-fluoroazetidin-1-yl)-2-(methylsulfonyl)ethanone; similarly the compound of (5e1), Table 2, Example B33, is the compound 2-cyclopropyl-1-(3-(5-(5-(3,5-dichlorophenyl)-5-(trifluoromethyl)-1,4,2-dioxazol-3-yl)pyridin-2-yl)-3-hydroxyazetidin-1-yl)ethanone; similarly the compound of Formula (2f1), Table 2, Example B96, is the compound 1-(3-(4-(3-(3-chloro-5-(trifluoromethyl)phenyl)-3-(trifluoromethyl)-3,4-dihydro-2H-pyrrol-5-yl)naphthalen-1-yl)-3-hydroxyazetidin-1-yl)-2-methoxyethanone; similarly, the compound of Formula (2e1), Table 3, Example C41, is the compound 3-(5-(3-(3,5-dichlorophenyl)-3-(trifluoromethyl)-3,4-dihydro-2H-pyrrol-5-yl)pyridin-2-yl)-1-(3,3,3-trifluoropropanoyl)azetidine-3-carbonitrile; similarly the compound of Formula (2d1), Table 3, Example C123, is the compound 3-(4-(3-(3,4-dichloro-5-(trifluoromethyl)phenyl)-3-(trifluoromethyl)-3,4-dihydro-2H-pyrrol-5-yl)phenyl)-1-(2-(methylthio)acetyl)azetidine-3-carbonitrile, and so forth.

Further, it is also contemplated that Formula 6d1-6f1 compounds comprising the $R^8$ substituent are substituted with $R^8$ as defined herein, and more particularly, $R^8$ is hydrogen, $C_1$-$C_6$ alkyl, $C_1$-$C_6$ haloalkyl, or cyano. For example, the compound of Formula (6e1), Table 2, Example B90, wherein $R^8$ is H, the compound is 1-(3-(5-(5-(3-chloro-5-(trifluoromethyl)phenyl)-5-(trifluoromethyl)-4,5-dihydro-1H-pyrazol-3-yl)pyridin-2-yl)-3-hydroxyazetidin-1-yl)-2-cyclopropylethanone; similarly the compound of Formula (6f1), Table 2, Example B79, wherein $R^8$ is methyl, the compound is 1-(3-(4-(5-(3,5-dichloro-4-fluorophenyl)-1-methyl-5-(trifluoromethyl)-4,5-dihydro-1H-pyrazol-3-yl)naphthalen-1-yl)-3-hydroxyazetidin-1-yl)-2-(thietan-3-yl)ethanone, and so forth.

(2d1)
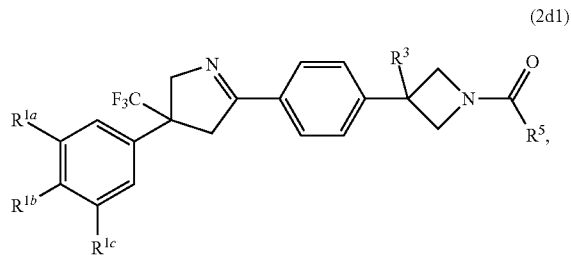
(2e1)
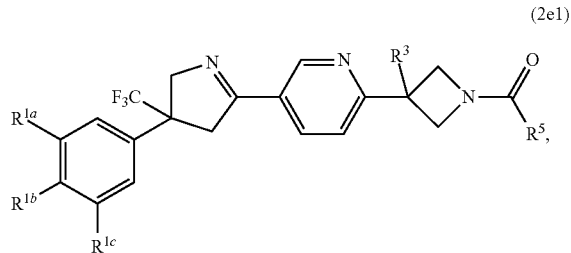
(2f1)
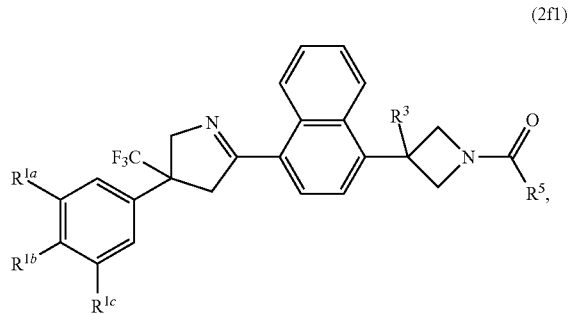
(3d1)
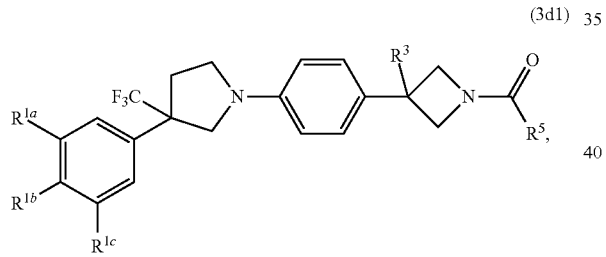
(3e1)
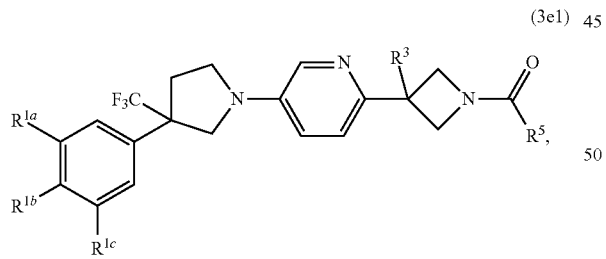
(3f1)
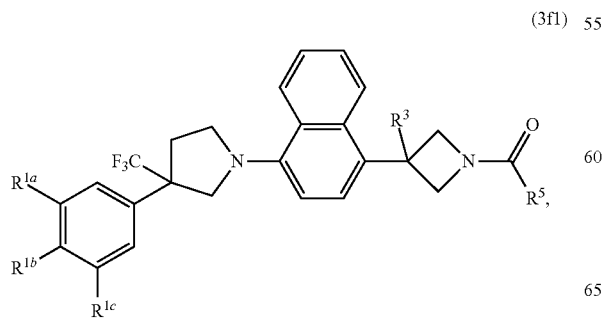
(4d1)
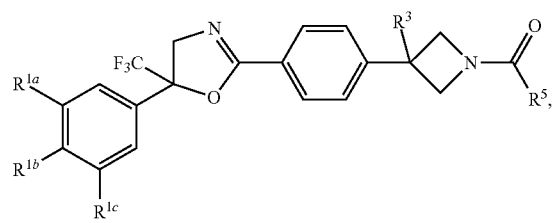
(4e1)
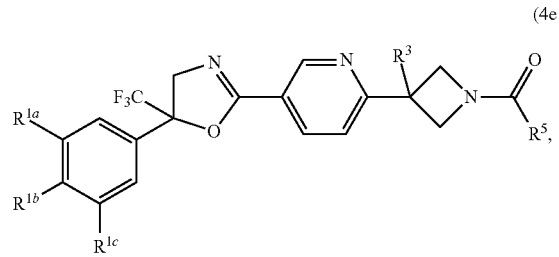
(4f1)
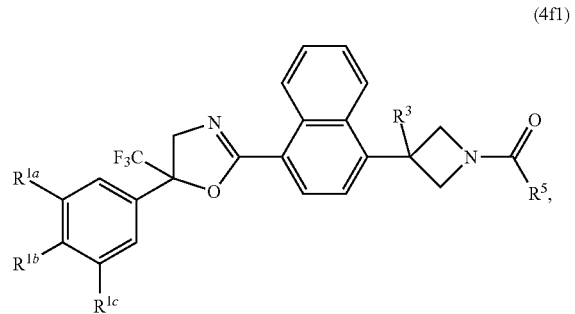
(5d1)
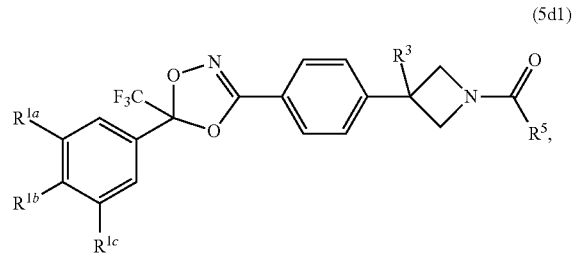
(5e1)
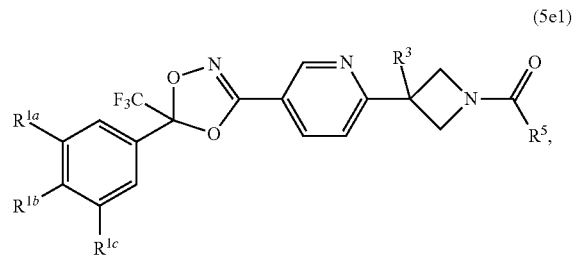
(5f1)
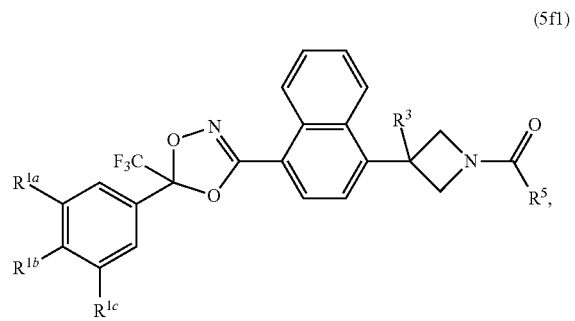

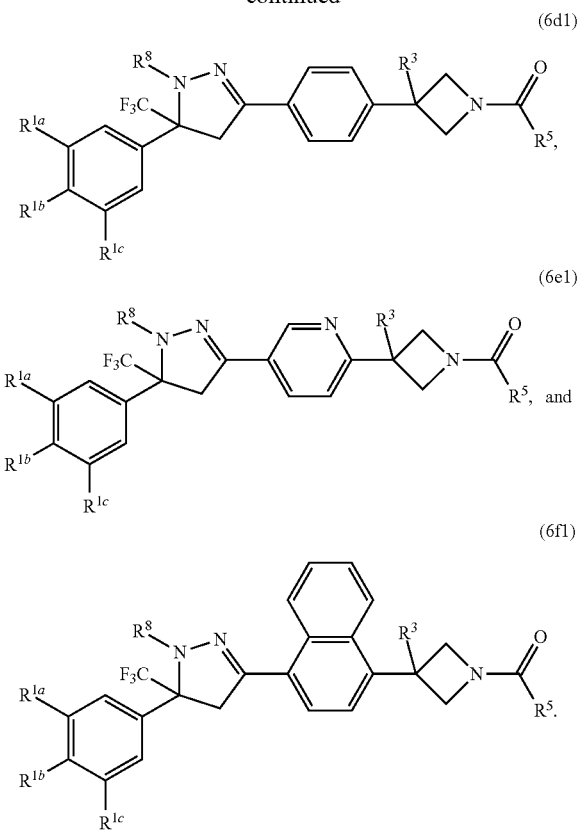

TABLE 1

Examples for Formula (2d1), (2e1), (2f1), (3d1), (3e1), (3f1), (4d1), (4e1), (4f1), (5d1), (5e1), (5f1), (6d1), (6e1), and (6f1)

| Example # | $R^{1a}$ | $R^{1b}$ | $R^{1c}$ | $R^3$ | $R^5$ |
|---|---|---|---|---|---|
| A1 | Cl | Cl | Cl | F | methyl |
| A2 | Cl | Cl | Cl | F | cyclopropyl |
| A3 | Cl | Cl | Cl | F | —NHCH$_3$ |
| A4 | Cl | Cl | Cl | F | —NHCH$_2$CH$_3$ |
| A5 | Cl | Cl | Cl | F | —NH-cyclopropyl |
| A6 | Cl | Cl | Cl | F | —CH$_2$-cyclopropyl |
| A7 | Cl | Cl | Cl | F | isopropyl |
| A8 | Cl | Cl | Cl | F | ethyl |
| A9 | Cl | Cl | Cl | F | propyl |
| A10 | Cl | Cl | Cl | F | —CH$_2$CN |
| A11 | Cl | Cl | Cl | F | —CH$_2$SCH$_3$ |
| A12 | Cl | Cl | Cl | F | —CH$_2$OCH$_3$ |
| A13 | Cl | Cl | Cl | F | cyclobutyl |
| A14 | Cl | Cl | Cl | F | —CH$_2$CF$_3$ |
| A15 | Cl | Cl | Cl | F | —NH$_2$ |
| A16 | Cl | Cl | Cl | F | —CH$_2$S(O)CH$_3$ |
| A17 | Cl | Cl | Cl | F | —CH$_2$S(O)$_2$CH$_3$ |
| A18 | Cl | Cl | Cl | F | —S(O)$_2$CH$_3$ |
| A19 | Cl | Cl | Cl | F | —CH$_2$OH |
| A20 | Cl | Cl | Cl | F | n-butyl |
| A21 | Cl | Cl | Cl | F | (thietanyl) |
| A22 | Cl | Cl | Cl | F | (thietanyl S=O) |
| A23 | Cl | Cl | Cl | F | (thietanyl S(=O)$_2$) |
| A24 | Cl | Cl | Cl | F | (CH$_2$-thietanyl) |
| A25 | Cl | Cl | Cl | F | (CH$_2$-thietanyl S=O) |
| A26 | Cl | Cl | Cl | F | (CH$_2$-thietanyl S(=O)$_2$) |
| A27 | Cl | Cl | Cl | F | (CH$_2$-2-pyridyl) |
| A28 | Cl | H | Cl | F | methyl |
| A29 | Cl | H | Cl | F | cyclopropyl |
| A30 | Cl | H | Cl | F | —NHCH$_3$ |
| A31 | Cl | H | Cl | F | —NHCH$_2$CH$_3$ |
| A32 | Cl | H | Cl | F | —NH-cyclopropyl |
| A33 | Cl | H | Cl | F | —CH$_2$-cyclopropyl |
| A34 | Cl | H | Cl | F | isopropyl |
| A35 | Cl | H | Cl | F | ethyl |
| A36 | Cl | H | Cl | F | propyl |
| A37 | Cl | H | Cl | F | —CH$_2$CN |
| A38 | Cl | H | Cl | F | —CH$_2$SCH$_3$ |
| A39 | Cl | H | Cl | F | —CH$_2$OCH$_3$ |
| A40 | Cl | H | Cl | F | cyclopropyl |
| A41 | Cl | H | Cl | F | —CH$_2$CF$_3$ |
| A42 | Cl | H | Cl | F | —NH$_2$ |
| A43 | Cl | H | Cl | F | —CH$_2$S(O)CH$_3$ |
| A44 | Cl | H | Cl | F | —CH$_2$S(O)$_2$CH$_3$ |
| A45 | Cl | H | Cl | F | —S(O)$_2$CH$_3$ |
| A46 | Cl | H | Cl | F | —CH$_2$OH |
| A47 | Cl | H | Cl | F | n-butyl |
| A48 | Cl | H | Cl | F | (thietanyl) |
| A49 | Cl | H | Cl | F | (thietanyl S=O) |
| A50 | Cl | H | Cl | F | (thietanyl S(=O)$_2$) |
| A51 | Cl | H | Cl | F | (CH$_2$-thietanyl) |

TABLE 1-continued

Examples for Formula (2d1), (2e1), (2f1), (3d1), (3e1), (3f1), (4d1), (4e1), (4f1), (5d1), (5e1), (5f1), (6d1), (6e1), and (6f1)

| Example # | $R^{1a}$ | $R^{1b}$ | $R^{1c}$ | $R^3$ | $R^5$ |
|---|---|---|---|---|---|
| A52 | Cl | H | Cl | F | (3-oxo-thietanyl)methyl |
| A53 | Cl | H | Cl | F | (3,3-dioxo-thietanyl)methyl |
| A54 | Cl | H | Cl | F | 2-pyridyl (methyl-substituted) |
| A55 | Cl | H | Cl | F | (2-pyridyl)methyl |
| A56 | Cl | F | Cl | F | —NH$_2$ |
| A57 | Cl | F | Cl | F | methyl |
| A58 | Cl | F | Cl | F | cyclopropyl |
| A59 | Cl | F | Cl | F | —NHCH$_3$ |
| A60 | Cl | F | Cl | F | —NHCH$_2$CH$_3$ |
| A61 | Cl | F | Cl | F | —NH-cyclopropyl |
| A62 | Cl | F | Cl | F | CH$_2$-cyclopropyl |
| A63 | Cl | F | Cl | F | isopropyl |
| A64 | Cl | F | Cl | F | ethyl |
| A65 | Cl | F | Cl | F | propyl |
| A66 | Cl | F | Cl | F | —CH$_2$CN |
| A67 | Cl | F | Cl | F | —CH$_2$SCH$_3$ |
| A68 | Cl | F | Cl | F | —CH$_2$OCH$_3$ |
| A69 | Cl | F | Cl | F | cyclobutyl |
| A70 | Cl | F | Cl | F | —CH$_2$CF$_3$ |
| A71 | Cl | F | Cl | F | —CH$_2$S(O)CH$_3$ |
| A72 | Cl | F | Cl | F | —CH$_2$S(O)$_2$CH$_3$ |
| A73 | Cl | F | Cl | F | —S(O)$_2$CH$_3$ |
| A74 | Cl | F | Cl | F | —CH$_2$OH |
| A75 | Cl | F | Cl | F | n-butyl |
| A76 | Cl | F | Cl | F | thietanyl |
| A77 | Cl | F | Cl | F | 3-oxo-thietanyl |
| A78 | Cl | F | Cl | F | 3,3-dioxo-thietanyl |
| A79 | Cl | F | Cl | F | (thietanyl)methyl |
| A80 | Cl | F | Cl | F | (3-oxo-thietanyl)methyl |
| A81 | Cl | F | Cl | F | (3,3-dioxo-thietanyl)methyl |
| A82 | Cl | F | Cl | F | 2-pyridyl |
| A83 | Cl | F | Cl | F | (2-pyridyl)methyl |
| A84 | Cl | H | CF$_3$ | F | —NH$_2$ |
| A85 | Cl | H | CF$_3$ | F | methyl |
| A86 | Cl | H | CF$_3$ | F | cyclopropyl |
| A87 | Cl | H | CF$_3$ | F | —NHCH$_3$ |
| A88 | Cl | H | CF$_3$ | F | —NHCH$_2$CH$_3$ |
| A89 | Cl | H | CF$_3$ | F | —NH-cyclopropyl |
| A90 | Cl | H | CF$_3$ | F | CH$_2$-cyclopropyl |
| A91 | Cl | H | CF$_3$ | F | isopropyl |
| A92 | Cl | H | CF$_3$ | F | ethyl |
| A93 | Cl | H | CF$_3$ | F | propyl |
| A94 | Cl | H | CF$_3$ | F | —CH$_2$CN |
| A95 | Cl | H | CF$_3$ | F | —CH$_2$SCH$_3$ |
| A96 | Cl | H | CF$_3$ | F | —CH$_2$OCH$_3$ |
| A97 | Cl | H | CF$_3$ | F | cyclobutyl |
| A98 | Cl | H | CF$_3$ | F | —CH$_2$CF$_3$ |
| A99 | Cl | H | CF$_3$ | F | —CH$_2$S(O)CH$_3$ |
| A100 | Cl | H | CF$_3$ | F | —CH$_2$S(O)$_2$CH$_3$ |
| A101 | Cl | H | CF$_3$ | F | —S(O)$_2$CH$_3$ |
| A102 | Cl | H | CF$_3$ | F | —CH$_2$OH |
| A103 | Cl | H | CF$_3$ | F | thietanyl |
| A104 | Cl | H | CF$_3$ | F | 3-oxo-thietanyl |
| A105 | Cl | H | CF$_3$ | F | 3,3-dioxo-thietanyl |
| A106 | Cl | H | CF$_3$ | F | (thietanyl)methyl |
| A107 | Cl | H | CF$_3$ | F | (3-oxo-thietanyl)methyl |
| A108 | Cl | H | CF$_3$ | F | (3,3-dioxo-thietanyl)methyl |

TABLE 1-continued

Examples for Formula (2d1), (2e1), (2f1), (3d1), (3e1), (3f1), (4d1), (4e1), (4f1), (5d1), (5e1), (5f1), (6d1), (6e1), and (6f1)

| Example # | R$^{1a}$ | R$^{1b}$ | R$^{1c}$ | R$^3$ | R$^5$ |
|---|---|---|---|---|---|
| A109 | Cl | H | CF$_3$ | F | 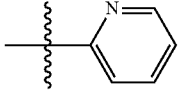 |
| A110 | Cl | H | CF$_3$ | F | 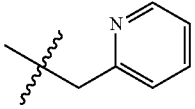 [SMILES: *Cc1ccccn1] |
| A111 | Cl | H | Cl | F | n-butyl |
| A112 | Cl | Cl | CF$_3$ | F | —NH$_2$ |
| A113 | Cl | Cl | CF$_3$ | F | methyl |
| A114 | Cl | Cl | CF$_3$ | F | cyclopropyl |
| A115 | Cl | Cl | CF$_3$ | F | —NHCH$_3$ |
| A116 | Cl | Cl | CF$_3$ | F | —NHCH$_2$CH$_3$ |
| A117 | Cl | Cl | CF$_3$ | F | —NH-cyclopropyl |
| A118 | Cl | Cl | CF$_3$ | F | CH$_2$-cyclopropyl |
| A119 | Cl | Cl | CF$_3$ | F | isopropyl |
| A120 | Cl | Cl | CF$_3$ | F | ethyl |
| A121 | Cl | Cl | CF$_3$ | F | propyl |
| A122 | Cl | Cl | CF$_3$ | F | —CH$_2$CN |
| A123 | Cl | Cl | CF$_3$ | F | —CH$_2$SCH$_3$ |
| A124 | Cl | Cl | CF$_3$ | F | —CH$_2$OCH$_3$ |
| A125 | Cl | Cl | CF$_3$ | F | cyclobutyl |
| A126 | Cl | Cl | CF$_3$ | F | —CH$_2$CF$_3$ |
| A127 | Cl | Cl | CF$_3$ | F | —CH$_2$S(O)CH$_3$ |
| A128 | Cl | Cl | CF$_3$ | F | —CH$_2$S(O)$_2$CH$_3$ |
| A129 | Cl | Cl | CF$_3$ | F | —S(O)$_2$CH$_3$ |
| A130 | Cl | Cl | CF$_3$ | F | —CH$_2$OH |
| A131 | Cl | Cl | CF$_3$ | F | n-butyl |
| A132 | Cl | Cl | CF$_3$ | F | 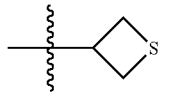 |
| A133 | Cl | Cl | CF$_3$ | F | 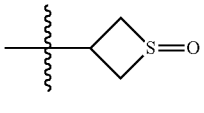 [SMILES: *C1CS(=O)C1] |
| A134 | Cl | Cl | CF$_3$ | F | 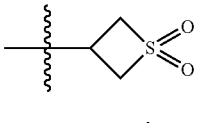 |
| A135 | Cl | Cl | CF$_3$ | F |  |
| A136 | Cl | Cl | CF$_3$ | F | 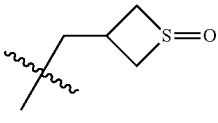 [SMILES: *CC1CS(=O)C1] |
| A137 | Cl | Cl | CF$_3$ | F | 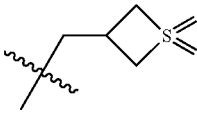 |
| A138 | Cl | Cl | CF$_3$ | F | 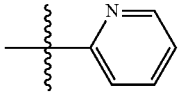 [SMILES: *c1ccccn1] |
| A139 | Cl | Cl | CF$_3$ | F | 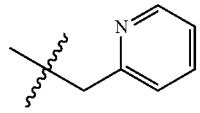 [SMILES: *Cc1ccccn1] |

TABLE 2

Examples for Formula (2d1), (2e1), (2f1), (3d1), (3e1), (3f1), (4d1), (4e1), (4f1), (5d1), (5e1), (5f1), (6d1), (6e1), and (6f1)

| Example # | R$^{1a}$ | R$^{1b}$ | R$^{1c}$ | R$^3$ | R$^5$ |
|---|---|---|---|---|---|
| B1 | Cl | Cl | Cl | OH | methyl |
| B2 | Cl | Cl | Cl | OH | cyclopropyl |
| B3 | Cl | Cl | Cl | OH | —NHCH$_3$ |
| B4 | Cl | Cl | Cl | OH | —NHCH$_2$CH$_3$ |
| B5 | Cl | Cl | Cl | OH | —NH-cyclopropyl |
| B6 | Cl | Cl | Cl | OH | —CH$_2$-cyclopropyl |
| B7 | Cl | Cl | Cl | OH | isopropyl |
| B8 | Cl | Cl | Cl | OH | ethyl |
| B9 | Cl | Cl | Cl | OH | propyl |
| B10 | Cl | Cl | Cl | OH | —CH$_2$CN |
| B11 | Cl | Cl | Cl | OH | —CH$_2$SCH$_3$ |
| B12 | Cl | Cl | Cl | OH | —CH$_2$OCH$_3$ |
| B13 | Cl | Cl | Cl | OH | cyclobutyl |
| B14 | Cl | Cl | Cl | OH | —CH$_2$CF$_3$ |
| B15 | Cl | Cl | Cl | OH | —NH$_2$ |
| B16 | Cl | Cl | Cl | OH | —CH$_2$S(O)CH$_3$ |
| B17 | Cl | Cl | Cl | OH | —CH$_2$S(O)$_2$CH$_3$ |
| B18 | Cl | Cl | Cl | OH | —S(O)$_2$CH$_3$ |
| B19 | Cl | Cl | Cl | OH | —CH$_2$OH |
| B20 | Cl | Cl | Cl | OH | n-butyl |
| B21 | Cl | Cl | Cl | OH | 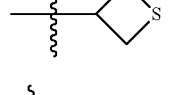 |
| B22 | Cl | Cl | Cl | OH |  |
| B23 | Cl | Cl | Cl | OH |  |
| B24 | Cl | Cl | Cl | OH |  |
| B25 | Cl | Cl | Cl | OH |  |
| B26 | Cl | Cl | Cl | OH |  |

TABLE 2-continued

Examples for Formula (2d1), (2e1), (2f1), (3d1), (3e1), (3f1), (4d1), (4e1), (4f1), (5d1), (5e1), (5f1), (6d1), (6e1), and (6f1)

| Example # | $R^{1a}$ | $R^{1b}$ | $R^{1c}$ | $R^3$ | $R^5$ |
|---|---|---|---|---|---|
| B27 | Cl | Cl | Cl | OH | 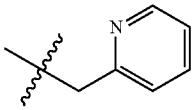 [SMILES: *Cc1ccccn1] |
| B28 | Cl | H | Cl | OH | methyl |
| B29 | Cl | H | Cl | OH | cyclopropyl |
| B30 | Cl | H | Cl | OH | —NHCH$_3$ |
| B31 | Cl | H | Cl | OH | —NHCH$_2$CH$_3$ |
| B32 | Cl | H | Cl | OH | —NH-cyclopropyl |
| B33 | Cl | H | Cl | OH | —CH$_2$-cyclopropyl |
| B34 | Cl | H | Cl | OH | isopropyl |
| B35 | Cl | H | Cl | OH | ethyl |
| B36 | Cl | H | Cl | OH | propyl |
| B37 | Cl | H | Cl | OH | —CH$_2$CN |
| B38 | Cl | H | Cl | OH | —CH$_2$SCH$_3$ |
| B39 | Cl | H | Cl | OH | —CH$_2$OCH$_3$ |
| B40 | Cl | H | Cl | OH | cyclobutyl |
| B41 | Cl | H | Cl | OH | —CH$_2$CF$_3$ |
| B42 | Cl | H | Cl | OH | —NH$_2$ |
| B43 | Cl | H | Cl | OH | —CH$_2$S(O)CH$_3$ |
| B44 | Cl | H | Cl | OH | —CH$_2$S(O)$_2$CH$_3$ |
| B45 | Cl | H | Cl | OH | —S(O)$_2$CH$_3$ |
| B46 | Cl | H | Cl | OH | —CH$_2$OH |
| B47 | Cl | H | Cl | OH | n-butyl |
| B48 | Cl | H | Cl | OH | 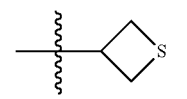 |
| B49 | Cl | H | Cl | OH | 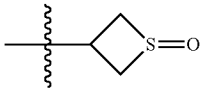 |
| B50 | Cl | H | Cl | OH | 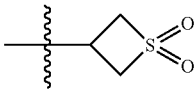 [SMILES: *C1CS(=O)(=O)C1] |
| B51 | Cl | H | Cl | OH | 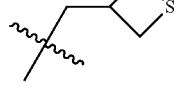 |
| B52 | Cl | H | Cl | OH | 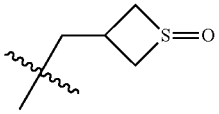 [SMILES: *CC1CS(=O)C1] |
| B53 | Cl | H | Cl | OH | 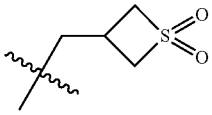 [SMILES: *CC1CS(=O)(=O)C1] |
| B54 | Cl | H | Cl | OH | 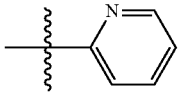 [SMILES: *c1ccccn1] |
| B55 | Cl | H | Cl | OH | 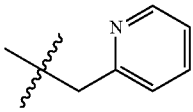 [SMILES: *Cc1ccccn1] |
| B56 | Cl | F | Cl | OH | —NH$_2$ |
| B57 | Cl | F | Cl | OH | methyl |
| B58 | Cl | F | Cl | OH | cyclopropyl |
| B59 | Cl | F | Cl | OH | —NHCH$_3$ |
| B60 | Cl | F | Cl | OH | —NHCH$_2$CH$_3$ |
| B61 | Cl | F | Cl | OH | —NH-cyclopropyl |
| B62 | Cl | F | Cl | OH | CH$_2$-cyclopropyl |
| B63 | Cl | F | Cl | OH | isopropyl |
| B64 | Cl | F | Cl | OH | ethyl |
| B65 | Cl | F | Cl | OH | propyl |
| B66 | Cl | F | Cl | OH | —CH$_2$CN |
| B67 | Cl | F | Cl | OH | —CH$_2$SCH$_3$ |
| B68 | Cl | F | Cl | OH | —CH$_2$OCH$_3$ |
| B69 | Cl | F | Cl | OH | cyclobutyl |
| B70 | Cl | F | Cl | OH | —CH$_2$CF$_3$ |
| B71 | Cl | F | Cl | OH | —CH$_2$S(O)CH$_3$ |
| B72 | Cl | F | Cl | OH | —CH$_2$S(O)$_2$CH$_3$ |
| B73 | Cl | F | Cl | OH | —S(O)$_2$CH$_3$ |
| B74 | Cl | F | Cl | OH | —CH$_2$OH |
| B75 | Cl | F | Cl | OH | n-butyl |
| B76 | Cl | F | Cl | OH | 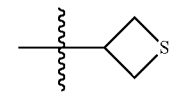 [SMILES: *C1CSC1] |
| B77 | Cl | F | Cl | OH | 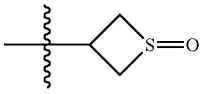 [SMILES: *C1CS(=O)C1] |
| B78 | Cl | F | Cl | OH | 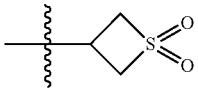 [SMILES: *C1CS(=O)(=O)C1] |
| B79 | Cl | F | Cl | OH |  |
| B80 | Cl | F | Cl | OH | 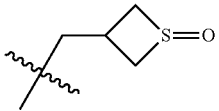 [SMILES: *CC1CS(=O)C1] |
| B81 | Cl | F | Cl | OH | 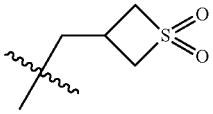 [SMILES: *CC1CS(=O)(=O)C1] |
| B82 | Cl | F | Cl | OH | 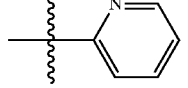 |
| B83 | Cl | F | Cl | OH | 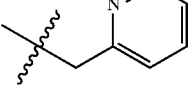 |
| B84 | Cl | H | CF$_3$ | OH | —NH$_2$ |
| B85 | Cl | H | CF$_3$ | OH | methyl |
| B86 | Cl | H | CF$_3$ | OH | cyclopropyl |
| B87 | Cl | H | CF$_3$ | OH | —NHCH$_3$ |
| B88 | Cl | H | CF$_3$ | OH | —NHCH$_2$CH$_3$ |
| B89 | Cl | H | CF$_3$ | OH | —NH-cyclopropyl |
| B90 | Cl | H | CF$_3$ | OH | CH$_2$-cyclopropyl |
| B91 | Cl | H | CF$_3$ | OH | isopropyl |

TABLE 2-continued

Examples for Formula (2d1), (2e1), (2f1), (3d1), (3e1), (3f1), (4d1), (4e1), (4f1), (5d1), (5e1), (5f1), (6d1), (6e1), and (6f1)

| Example # | R$^{1a}$ | R$^{1b}$ | R$^{1c}$ | R$^3$ | R$^5$ |
|---|---|---|---|---|---|
| B92 | Cl | H | CF$_3$ | OH | ethyl |
| B93 | Cl | H | CF$_3$ | OH | propyl |
| B94 | Cl | H | CF$_3$ | OH | —CH$_2$CN |
| B95 | Cl | H | CF$_3$ | OH | —CH$_2$SCH$_3$ |
| B96 | Cl | H | CF$_3$ | OH | —CH$_2$OCH$_3$ |
| B97 | Cl | H | CF$_3$ | OH | cyclobutyl |
| B98 | Cl | H | CF$_3$ | OH | —CH$_2$CF$_3$ |
| B99 | Cl | H | CF$_3$ | OH | —CH$_2$S(O)CH$_3$ |
| B100 | Cl | H | CF$_3$ | OH | —CH$_2$S(O)$_2$CH$_3$ |
| B101 | Cl | H | CF$_3$ | OH | —S(O)$_2$CH$_3$ |
| B102 | Cl | H | CF$_3$ | OH | —CH$_2$OH |
| B103 | Cl | H | CF$_3$ | OH | 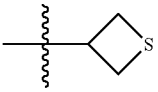 |
| B104 | Cl | H | CF$_3$ | OH | 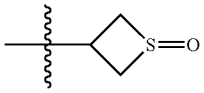 [SMILES: *C1CS(=O)C1] |
| B105 | Cl | H | CF$_3$ | OH | 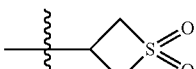 |
| B106 | Cl | H | CF$_3$ | OH | 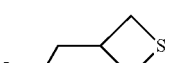 |
| B107 | Cl | H | CF$_3$ | OH | 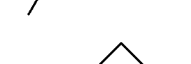 |
| B108 | Cl | H | CF$_3$ | OH |  |
| B109 | Cl | H | CF$_3$ | OH | 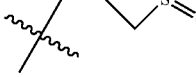 |
| B110 | Cl | H | CF$_3$ | OH | 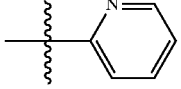 |
| B111 | Cl | H | Cl | OH | n-butyl |
| B112 | Cl | Cl | CF$_3$ | OH | —NH$_2$ |
| B113 | Cl | Cl | CF$_3$ | OH | methyl |
| B114 | Cl | Cl | CF$_3$ | OH | cyclopropyl |
| B115 | Cl | Cl | CF$_3$ | OH | —NHCH$_3$ |
| B116 | Cl | Cl | CF$_3$ | OH | —NHCH$_2$CH$_3$ |
| B117 | Cl | Cl | CF$_3$ | OH | —NH-cyclopropyl |
| B118 | Cl | Cl | CF$_3$ | OH | CH$_2$-cyclopropyl |
| B119 | Cl | Cl | CF$_3$ | OH | isopropyl |
| B120 | Cl | Cl | CF$_3$ | OH | ethyl |
| B121 | Cl | Cl | CF$_3$ | OH | Propyl |
| B122 | Cl | Cl | CF$_3$ | OH | —CH$_2$CN |
| B123 | Cl | Cl | CF$_3$ | OH | —CH$_2$SCH$_3$ |
| B124 | Cl | Cl | CF$_3$ | OH | —CH$_2$OCH$_3$ |
| B125 | Cl | Cl | CF$_3$ | OH | cyclobutyl |
| B126 | Cl | Cl | CF$_3$ | OH | —CH$_2$CF$_3$ |
| B127 | Cl | Cl | CF$_3$ | OH | —CH$_2$S(O)CH$_3$ |
| B128 | Cl | Cl | CF$_3$ | OH | —CH$_2$S(O)$_2$CH$_3$ |
| B129 | Cl | Cl | CF$_3$ | OH | —S(O)$_2$CH$_3$ |
| B130 | Cl | Cl | CF$_3$ | OH | —CH$_2$OH |
| B131 | Cl | Cl | CF$_3$ | OH | n-butyl |
| B132 | Cl | Cl | CF$_3$ | OH | 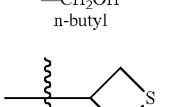 |
| B133 | Cl | Cl | CF$_3$ | OH | 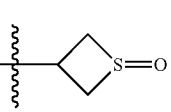 |
| B134 | Cl | Cl | CF$_3$ | OH | 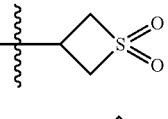 |
| B135 | Cl | Cl | CF$_3$ | OH |  |
| B136 | Cl | Cl | CF$_3$ | OH |  |
| B137 | Cl | Cl | CF$_3$ | OH | 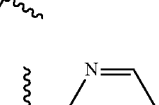 |
| B138 | Cl | Cl | CF$_3$ | OH | 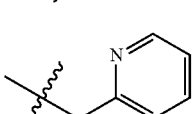 |
| B139 | Cl | Cl | CF$_3$ | OH | 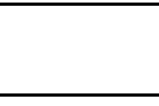 |

TABLE 3

Examples for Formula (2d1), (2e1), (2f1), (3d1), (3e1), (3f1), (4d1), (4e1), (4f1), (5d1), (5e1), (5f1), (6d1), (6e1), and (6f1)

| Example # | R$^{1a}$ | R$^{1b}$ | R$^{1c}$ | R$^3$ | R$^5$ |
|---|---|---|---|---|---|
| C1 | Cl | Cl | Cl | CN | methyl |
| C2 | Cl | Cl | Cl | CN | cyclopropyl |
| C3 | Cl | Cl | Cl | CN | —NHCH$_3$ |
| C4 | Cl | Cl | Cl | CN | —NHCH$_2$CH$_3$ |
| C5 | Cl | Cl | Cl | CN | —NH-cyclopropyl |
| C6 | Cl | Cl | Cl | CN | —CH$_2$-cyclopropyl |
| C7 | Cl | Cl | Cl | CN | isopropyl |
| C8 | Cl | Cl | Cl | CN | ethyl |
| C9 | Cl | Cl | Cl | CN | propyl |
| C10 | Cl | Cl | Cl | CN | —CH$_2$CN |
| C11 | Cl | Cl | Cl | CN | —CH$_2$SCH$_3$ |
| C12 | Cl | Cl | Cl | CN | —CH$_2$OCH$_3$ |
| C13 | Cl | Cl | Cl | CN | cyclobutyl |

TABLE 3-continued

Examples for Formula (2d1), (2e1), (2f1), (3d1), (3e1), (3f1), (4d1), (4e1), (4f1), (5d1), (5e1), (5f1), (6d1), (6e1), and (6f1)

| Example # | $R^{1a}$ | $R^{1b}$ | $R^{1c}$ | $R^3$ | $R^5$ |
|---|---|---|---|---|---|
| C14 | Cl | Cl | Cl | CN | —CH$_2$CF$_3$ |
| C15 | Cl | Cl | Cl | CN | —NH$_2$ |
| C16 | Cl | Cl | Cl | CN | —CH$_2$S(O)CH$_3$ |
| C17 | Cl | Cl | Cl | CN | —CH$_2$S(O)$_2$CH$_3$ |
| C18 | Cl | Cl | Cl | CN | —S(O)$_2$CH$_3$ |
| C19 | Cl | Cl | Cl | CN | —CH$_2$OH |
| C20 | Cl | Cl | Cl | CN | n-butyl |
| C21 | Cl | Cl | Cl | CN | thietanyl |
| C22 | Cl | Cl | Cl | CN | thietanyl S-oxide |
| C23 | Cl | Cl | Cl | CN | thietanyl S,S-dioxide |
| C24 | Cl | Cl | Cl | CN | CH$_2$-thietanyl |
| C25 | Cl | Cl | Cl | CN | CH$_2$-thietanyl S-oxide |
| C26 | Cl | Cl | Cl | CN | CH$_2$-thietanyl S,S-dioxide |
| C27 | Cl | Cl | Cl | CN | CH$_2$-pyridin-2-yl |
| C28 | Cl | H | Cl | CN | methyl |
| C29 | Cl | H | Cl | CN | cyclopropyl |
| C30 | Cl | H | Cl | CN | —NHCH$_3$ |
| C31 | Cl | H | Cl | CN | —NHCH$_2$CH$_3$ |
| C32 | Cl | H | Cl | CN | —NH-cyclopropyl |
| C33 | Cl | H | Cl | CN | —CH$_2$-cyclopropyl |
| C34 | Cl | H | Cl | CN | isopropyl |
| C35 | Cl | H | Cl | CN | ethyl |
| C36 | Cl | H | Cl | CN | propyl |
| C37 | Cl | H | Cl | CN | —CH$_2$CN |
| C38 | Cl | H | Cl | CN | —CH$_2$SCH$_3$ |
| C39 | Cl | H | Cl | CN | —CH$_2$OCH$_3$ |
| C40 | Cl | H | Cl | CN | cyclobutyl |
| C41 | Cl | H | Cl | CN | —CH$_2$CF$_3$ |
| C42 | Cl | H | Cl | CN | —NH$_2$ |
| C43 | Cl | H | Cl | CN | —CH$_2$S(O)CH$_3$ |
| C44 | Cl | H | Cl | CN | —CH$_2$S(O)$_2$CH$_3$ |
| C45 | Cl | H | Cl | CN | —S(O)$_2$CH$_3$ |
| C46 | Cl | H | Cl | CN | —CH$_2$OH |
| C47 | Cl | H | Cl | CN | n-butyl |
| C48 | Cl | H | Cl | CN | thietanyl |
| C49 | Cl | H | Cl | CN | thietanyl S-oxide |
| C50 | Cl | H | Cl | CN | thietanyl S,S-dioxide |
| C51 | Cl | H | Cl | CN | CH$_2$-thietanyl |
| C52 | Cl | H | Cl | CN | CH$_2$-thietanyl S-oxide |
| C53 | Cl | H | Cl | CN | CH$_2$-thietanyl S,S-dioxide |
| C54 | Cl | H | Cl | CN | pyridin-2-yl |
| C55 | Cl | H | Cl | CN | CH$_2$-pyridin-2-yl |
| C56 | Cl | F | Cl | CN | —NH$_2$ |
| C57 | Cl | F | Cl | CN | methyl |
| C58 | Cl | F | Cl | CN | cyclopropyl |
| C59 | Cl | F | Cl | CN | —NHCH$_3$ |
| C60 | Cl | F | Cl | CN | —NHCH$_2$CH$_3$ |
| C61 | Cl | F | Cl | CN | —NH-cyclopropyl |
| C62 | Cl | F | Cl | CN | CH$_2$-cyclopropyl |
| C63 | Cl | F | Cl | CN | isopropyl |
| C64 | Cl | F | Cl | CN | ethyl |
| C65 | Cl | F | Cl | CN | propyl |
| C66 | Cl | F | Cl | CN | —CH$_2$CN |
| C67 | Cl | F | Cl | CN | —CH$_2$SCH$_3$ |
| C68 | Cl | F | Cl | CN | —CH$_2$OCH$_3$ |
| C69 | Cl | F | Cl | CN | cyclobutyl |
| C70 | Cl | F | Cl | CN | —CH$_2$CF$_3$ |
| C71 | Cl | F | Cl | CN | —CH$_2$S(O)CH$_3$ |
| C72 | Cl | F | Cl | CN | —CH$_2$S(O)$_2$CH$_3$ |
| C73 | Cl | F | Cl | CN | —S(O)$_2$CH$_3$ |
| C74 | Cl | F | Cl | CN | —CH$_2$OH |
| C75 | Cl | F | Cl | CN | n-butyl |
| C76 | Cl | F | Cl | CN | thietanyl |
| C77 | Cl | F | Cl | CN | thietanyl S-oxide |

TABLE 3-continued

Examples for Formula (2d1), (2e1), (2f1), (3d1), (3e1), (3f1), (4d1), (4e1), (4f1), (5d1), (5e1), (5f1), (6d1), (6e1), and (6f1)

| Example # | R$^{1a}$ | R$^{1b}$ | R$^{1c}$ | R$^3$ | R$^5$ |
|---|---|---|---|---|---|
| C78 | Cl | F | Cl | CN | 3-(1,1-dioxo-thietanyl) |
| C79 | Cl | F | Cl | CN | CH$_2$-(3-thietanyl) |
| C80 | Cl | F | Cl | CN | 3-(1-oxo-thietanyl) |
| C81 | Cl | F | Cl | CN | 3-(1,1-dioxo-thietanyl) |
| C82 | Cl | F | Cl | CN | 2-pyridyl |
| C83 | Cl | F | Cl | CN | CH$_2$-(2-pyridyl) |
| C84 | Cl | H | CF$_3$ | CN | —NH$_2$ |
| C85 | Cl | H | CF$_3$ | CN | methyl |
| C86 | Cl | H | CF$_3$ | CN | cyclopropyl |
| C87 | Cl | H | CF$_3$ | CN | —NHCH$_3$ |
| C88 | Cl | H | CF$_3$ | CN | —NHCH$_2$CH$_3$ |
| C89 | Cl | H | CF$_3$ | CN | —NH-cyclopropyl |
| C90 | Cl | H | CF$_3$ | CN | CH$_2$-cyclopropyl |
| C91 | Cl | H | CF$_3$ | CN | isopropyl |
| C92 | Cl | H | CF$_3$ | CN | ethyl |
| C93 | Cl | H | CF$_3$ | CN | propyl |
| C94 | Cl | H | CF$_3$ | CN | —CH$_2$CN |
| C95 | Cl | H | CF$_3$ | CN | —CH$_2$SCH$_3$ |
| C96 | Cl | H | CF$_3$ | CN | —CH$_2$OCH$_3$ |
| C97 | Cl | H | CF$_3$ | CN | cyclobutyl |
| C98 | Cl | H | CF$_3$ | CN | —CH$_2$CF$_3$ |
| C99 | Cl | H | CF$_3$ | CN | —CH$_2$S(O)CH$_3$ |
| C100 | Cl | H | CF$_3$ | CN | —CH$_2$S(O)$_2$CH$_3$ |
| C101 | Cl | H | CF$_3$ | CN | —S(O)$_2$CH$_3$ |
| C102 | Cl | H | CF$_3$ | CN | —CH$_2$OH |
| C103 | Cl | H | CF$_3$ | CN | 3-thietanyl |
| C104 | Cl | H | CF$_3$ | CN | 3-(1-oxo-thietanyl) |
| C105 | Cl | H | CF$_3$ | CN | 3-(1,1-dioxo-thietanyl) |
| C106 | Cl | H | CF$_3$ | CN | CH$_2$-(3-thietanyl) |
| C107 | Cl | H | CF$_3$ | CN | CH$_2$-(3-(1-oxo-thietanyl)) |
| C108 | Cl | H | CF$_3$ | CN | CH$_2$-(3-(1,1-dioxo-thietanyl)) |
| C109 | Cl | H | CF$_3$ | CN | 2-pyridyl |
| C110 | Cl | H | CF$_3$ | CN | CH$_2$-(2-pyridyl) |
| C111 | Cl | H | Cl | CN | n-butyl |
| C112 | Cl | Cl | CF$_3$ | CN | —NH$_2$ |
| C113 | Cl | Cl | CF$_3$ | CN | methyl |
| C114 | Cl | Cl | CF$_3$ | CN | cyclopropyl |
| C115 | Cl | Cl | CF$_3$ | CN | —NHCH$_3$ |
| C116 | Cl | Cl | CF$_3$ | CN | —NHCH$_2$CH$_3$ |
| C117 | Cl | Cl | CF$_3$ | CN | —NH-cyclopropyl |
| C118 | Cl | Cl | CF$_3$ | CN | CH$_2$-cyclopropyl |
| C119 | Cl | Cl | CF$_3$ | CN | isopropyl |
| C120 | Cl | Cl | CF$_3$ | CN | ethyl |
| C121 | Cl | Cl | CF$_3$ | CN | propyl |
| C122 | Cl | Cl | CF$_3$ | CN | —CH$_2$CN |
| C123 | Cl | Cl | CF$_3$ | CN | —CH$_2$SCH$_3$ |
| C124 | Cl | Cl | CF$_3$ | CN | —CH$_2$OCH$_3$ |
| C125 | Cl | Cl | CF$_3$ | CN | cyclobutyl |
| C126 | Cl | Cl | CF$_3$ | CN | —CH$_2$CF$_3$ |
| C127 | Cl | Cl | CF$_3$ | CN | —CH$_2$S(O)CH$_3$ |
| C128 | Cl | Cl | CF$_3$ | CN | —CH$_2$S(O)$_2$CH$_3$ |
| C129 | Cl | Cl | CF$_3$ | CN | —S(O)$_2$CH$_3$ |
| C130 | Cl | Cl | CF$_3$ | CN | —CH$_2$OH |
| C131 | Cl | Cl | CF$_3$ | CN | n-butyl |
| C132 | Cl | Cl | CF$_3$ | CN | 3-thietanyl |
| C133 | Cl | Cl | CF$_3$ | CN | 3-(1-oxo-thietanyl) |
| C134 | Cl | Cl | CF$_3$ | CN | 3-(1,1-dioxo-thietanyl) |
| C135 | Cl | Cl | CF$_3$ | CN | CH$_2$-(3-thietanyl) |

TABLE 3-continued

Examples for Formula (2d1), (2e1), (2f1), (3d1), (3e1), (3f1), (4d1), (4e1), (4f1), (5d1), (5e1), (5f1), (6d1), (6e1), and (6f1)

| Example # | $R^{1a}$ | $R^{1b}$ | $R^{1c}$ | $R^3$ | $R^5$ |
|---|---|---|---|---|---|
| C136 | Cl | Cl | $CF_3$ | CN | ![structure] |
| C137 | Cl | Cl | $CF_3$ | CN | ![structure] |
| C138 | Cl | Cl | $CF_3$ | CN | ![structure] |
| C139 | Cl | Cl | $CF_3$ | CN | ![structure] |

BIOLOGICAL ASSAYS

The biological activity of the compounds of the present invention can be tested against fleas, ticks, flies, and or sea lice using the test methods described below.

Horn Fly (*Haematobia irritans*) Feed Assay

Formula (1) compounds can be dissolved in DMSO and aliquots added to citrated bovine blood in a membrane covered Petri dish. Approximately ten horn flies can be placed onto each Petri dish and covered. The flies are allowed to feed on the treated blood cell. Flies are held at approximately 80° F. with a minimum of approximately 50% relative humidity. Flies are examined for knockdown and mortality at approximately 2 and 24 hours. Endpoint data is recorded as a lethal dose 90% ($LD^{90}$) in µg/mL.

Stable Fly (*Stomoxys calcitrans*) Topical Assay

Formula (1) compounds can be dissolved in acetone, and 1 µL of the solution placed on the thorax of an anesthetized fly (n=10). The flies are allowed to recover, and are incubated for 24 hours at room temperature. Flies are examined for knockdown and mortality at 2 and 24 hours. Endpoint data is recorded as lethal dose 90% ($LD^{90}$) in µg/fly.

Flea (*Ctenocephalides felis*) Membrane Feed Assay-Adult

Formula (1) compounds were dissolved in DMSO and aliquots added to citrated bovine blood in a membrane covered Petri dish pre-warmed to 37° C. Feeding tubes containing approximately 30-35 adult fleas were placed onto the Petri dishes. The fleas fed for approximately 2 hours. Fleas were observed for knockdown and/or death at approximately 2 and 24 hours. Endpoint data is recorded as a lethal dose 80% ($LD^{80}$) in µg/mL. In this assay, Example 2 and 5 had an $LD^{80}$ of 0.3 and 1 in µg/mL, respectively. Example 3 and 6 had an ($LD^{80}$) of 3 µg/mL. Further, the results can be assessed at 24 hours based on minimum effective concentration (MEC) in µM with a 10-flea sample. In this assay, Examples 2, 3, 4, and 5, had an MEC of 1 µM. Example 1 had an MEC of 3 µM, and Examples 8, 14-16, and 18 had an MEC of 30 µM.

Soft Tick (*Ornithidorus turicata*) Blood Feed Assay

Formula (1) compounds were dissolved in dimethylsulfoxide (DMSO) and aliquots added to citrated bovine blood in a membrane covered Petri dish. The Petri dish was placed on a warming tray. Approximately 5 nymph stage ticks are placed onto the membrane, covered, and left to feed. Fed ticks are removed and placed into a Petri dish with sand. Fed ticks are observed at approximately 24, 48 and 72 hours for paralysis and/or death. Endpoint data is recorded as a lethal dose 100% ($LD^{100}$) in µg/mL. In this assay, Example 6 and Example 14 had an $LD^{100}$ of <0.03 µg/mL; Examples 2-4 had an $LD^{100}$ of 0.1 µg/mL; Examples 1 and 5 had an $LD^{100}$ of 0.3 µg/mL; and Examples 8, 10, 12, 15, 16, and 18 had an $LD^{100}$ of >0.3 µg/mL.

Copepod (*Lepeophtheirus salmonis*) BioAssay

Formula (1) compounds can dissolved in sea water. Ten pre-adult/adult salmon lice are exposed for 24 hours. Lice are monitored for motility and endpoint data is recorded as an Effective Concentration 100%) ($Ec^{100}$) based on immotility.

We claim:

1. A compound of Formula (1)

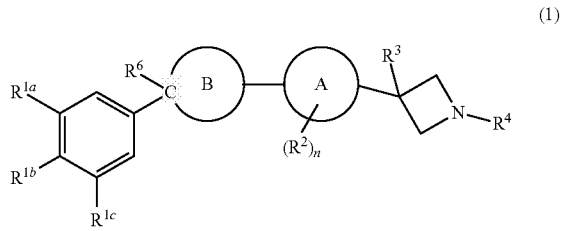

(1)

wherein

A is phenyl, naphthyl, or heteroaryl where said heteroaryl contains 1 to 4 heteroatoms each independently selected from N, O and S;

B is

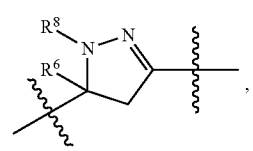

B1

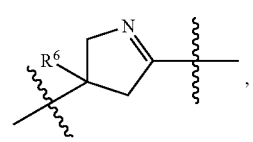

B2

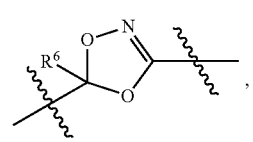

B3

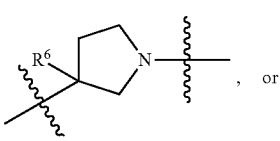

B4

, or

-continued

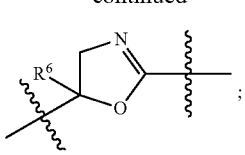

B5 where in "~~~" represents the point of attachment;

$R^{1a}$, $R^{1b}$, and $R^{1c}$ are each independently hydrogen, halo, hydroxyl, cyano, nitro, $C_1$-$C_6$alkyl, $C_1$-$C_6$haloalkyl, $C_1$-$C_6$alkoxy, $C_0$-$C_3$alkyl$C_3$-$C_6$cycloalkyl, $C_1$-$C_6$haloalkoxy, —C(O)NH$_2$, —SF$_5$, or —S(O)$_p$R;

$R^2$ is halo, cyano, $C_1$-$C_6$alkyl, $C_1$-$C_6$haloalkyl, nitro, hydroxyl, —C(O)NR$^a$R$^b$, $C_2$-$C_6$alkenyl, $C_2$-$C_6$alkynyl, —S(O)$_p$R, or —OR;

$R^3$ is hydrogen, halo, hydroxyl, cyano, $C_1$-$C_6$alkyl, $C_1$-$C_6$haloalkyl, $C_0$-$C_3$alkyl$C_3$-$C_6$cycloalkyl, —C(O)NH$_2$, nitro, —SC(O)R, —C(O)NR$^a$R$^b$, $C_0$-$C_3$alkylNR$^a$R$^4$, —NR$^a$NR$^b$R$^4$, —NR$^a$OR$^b$, —ONR$^a$R$^b$, N$_3$, —NHR$^4$, —OR, or —S(O)$_p$R;

$R^4$ is hydrogen, $C_1$-$C_6$alkyl, $C_0$-$C_6$alkyl$C_3$-$C_6$cycloalkyl, —C(O)R$^5$, —C(S)R$^5$, —C(O)NR$^a$R$^5$, —C(O)C(O)NR$^a$R$^5$, —S(O)$_p$R$^c$, —S(O)$_2$NR$^a$R$^5$, —C(NR$^7$)R$^5$, —C(NR$^7$)NR$^a$R$^5$, $C_0$-$C_6$alkylphenyl, $C_0$-$C_6$alkylheteroaryl, or $C_0$-$C_6$alkylheterocycle;

$R^5$ is hydrogen, $C_1$-$C_6$alkyl, $C_2$-$C_6$alkenyl, $C_0$-$C_6$alkyl$C_3$-$C_6$cycloalkyl, $C_0$-$C_6$alkylphenyl, $C_0$-$C_6$alkylheteroaryl, or $C_0$-$C_6$alkylheterocycle;

$R^6$ is cyano, $C_1$-$C_6$alkyl, $C_1$-$C_6$haloalkyl, —C(O)NR$^a$R$^b$, $C_2$-$C_6$alkenyl, $C_2$-$C_6$alkynyl, $C_2$-$C_6$haloalkenyl, or $C_2$-$C_6$haloalkynyl;

$R^7$ is hydrogen, $C_1$-$C_6$alkyl, hydroxyl, cyano, nitro, —S(O)$_p$R$^c$, or $C_1$-$C_6$alkoxy;

$R^8$ is hydrogen, $C_1$-$C_6$alkyl, hydroxyl, cyano, —S(O)$_p$R$^c$, or $C_1$-$C_6$alkoxy;

R is $C_1$-$C_6$alkyl or $C_3$-$C_6$cycloalkyl each optionally substituted by at least one halo;

R$^a$ is hydrogen, $C_1$-$C_6$alkyl, or $C_0$-$C_3$alkyl$C_3$-$C_6$cycloalkyl; wherein the alkyl and alkylcycloalkyl is optionally substituted by cyano or at least one halo substituent;

R$^b$ is hydrogen, $C_1$-$C_6$alkyl, $C_3$-$C_6$cycloalkyl, $C_0$-$C_3$alkylphenyl, $C_0$-$C_3$alkylheteroaryl, or $C_0$-$C_3$alkylheterocycle, each optionally substituted, where chemically possible, with at least one substituent selected from hydroxyl, cyano, halo, or —S(O)$_p$R;

R$^c$ is $C_1$-$C_6$alkyl, $C_1$-$C_6$haloalkyl, $C_1$-$C_6$haloalkyl$C_3$-$C_6$cycloalkyl, $C_0$-$C_3$alkyl$C_3$-$C_6$cycloalkyl, $C_0$-$C_3$alkylphenyl, $C_0$-$C_3$alkylheteroaryl, or $C_0$-$C_3$alkylheterocycle each optionally substituted with at least one substituent selected from cyano, halo, hydroxyl, oxo, $C_1$-$C_6$alkyl, $C_1$-$C_6$alkoxy, $C_1$-$C_6$haloalkoxy, $C_1$-$C_6$haloalkyl, —S(O)$_p$R, —SH, —S(O)$_p$NR$^a$R$^b$, —NR$^a$R$^b$, —NR$^a$C(O)R$^b$, —SC(O)R$^b$, —SCN, or —C(O)NR$^a$R$^b$;

each of R$^4$ and R$^5$ $C_1$-$C_6$alkyl or $C_0$-$C_6$alkyl$C_3$-$C_6$cycloalkyl can be optionally and independently substituted by at least one substituent selected from $C_1$-$C_6$alkyl, cyano, halo, hydroxyl, $C_1$-$C_6$hydroxyalkyl, oxo, $C_1$-$C_6$alkoxy, $C_1$-$C_6$haloalkoxy, $C_1$-$C_6$alkyl, $C_1$-$C_6$haloalkyl, —S(O)$_p$R$^c$, —SH, —S(O)$_p$NR$^a$R$^b$, —NR$^a$R$^b$, —NR$^a$C(O)R$^b$, —SC(O)R$^c$, —SCN, or —C(O)NR$^a$R$^b$; and wherein R$^4$ and R$^5$ $C_0$-$C_6$alkylphenyl, $C_0$-$C_6$alkylheteroaryl, or $C_0$-$C_6$alkylheterocycle moiety can be further optionally substituted with at least one substituent selected from $C_1$-$C_6$alkyl, cyano, halo, oxo, =S, =NR$^7$, hydroxyl, $C_1$-$C_6$hydroxyalkyl, $C_1$-$C_6$alkoxy, $C_1$-$C_6$alkyl, $C_1$-$C_6$haloalkyl, —SH, —S(O)$_p$R, and $C_1$-$C_6$haloalkoxy;

n is the integer 0, 1, or 2, and when n is 2, each $R^2$ may be identical or different from each other; and p is the integer 0, 1, or 2, stereoisomers thereof, and pharmaceutically or veterinarily acceptable salts thereof.

2. The compound of claim 1 having Formula (2)

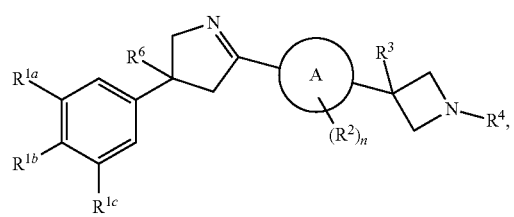

(2)

stereoisomers thereof, and pharmaceutically or veterinarily acceptable salts thereof.

3. The compound of claim 2 wherein A is phenyl, naphthyl, or pyridinyl;

$R^{1a}$, $R^{1b}$, and $R^{1c}$ are each independently selected from hydrogen, halo, hydroxyl, and $C_1$-$C_6$ haloalkyl;

$R^2$ is halo, cyano, hydroxyl, $C_1$-$C_6$alkyl, $C_1$-$C_6$haloalkyl, —C(O)NR$^a$R$^b$, or —OR; and wherein n is the integer 0, 1, or 2;

$R^3$ is hydrogen, halo, hydroxyl, N$_3$, or cyano;

$R^4$ is —C(O)R$^5$; and $R^6$ is $C_1$-$C_6$haloalkyl, stereoisomers thereof, and pharmaceutically or veterinarily acceptable salts thereof.

4. The compound of claim 3 wherein A is phenyl;

$R^{1a}$, $R^{1b}$, and $R^{1c}$ are each independently selected from hydrogen, halo, and CF$_3$;

$R^3$ is hydrogen, halo or hydroxyl;

$R^6$ is CF$_3$; and n is the integer 0, stereoisomers thereof, and pharmaceutically or veterinarily acceptable salts thereof.

5. The compound of claim 1 having Formula (5)

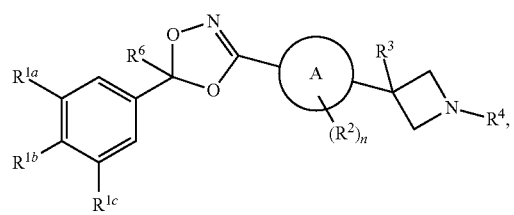

(5)

stereoisomers thereof, and pharmaceutically or veterinarily acceptable salts thereof.

6. The compound of claim 5 wherein A is phenyl, naphthyl, or pyridinyl;

$R^{1a}$, $R^{1b}$, and $R^{1c}$ are each independently selected from hydrogen, halo, hydroxyl, and $C_1$-$C_6$haloalkyl;

$R^2$ is halo, cyano, hydroxyl, $C_1$-$C_6$alkyl, $C_1$-$C_6$haloalkyl, —C(O)NR$^a$R$^b$, or —OR; and wherein n is the integer 0, 1, or 2;
$R^3$ is hydrogen, halo, hydroxyl, $N_3$, or cyano;
$R^4$ is —C(O)R$^5$; and
$R^6$ is $C_1$-$C_6$haloalkyl,
stereoisomers thereof, and pharmaceutically or veterinarily acceptable salts thereof.

7. The compound of claim 6 wherein A is phenyl;
$R^{1a}$, $R^{1b}$, and $R^{1c}$ are each independently selected from hydrogen, halo, and $CF_3$;
$R^3$ is hydrogen, halo or hydroxyl;
$R^6$ is $CF_3$; and
n is the integer 0,
stereoisomers thereof, and pharmaceutically or veterinarily acceptable salts thereof.

8. The compound of claim 1 having Formula (6)

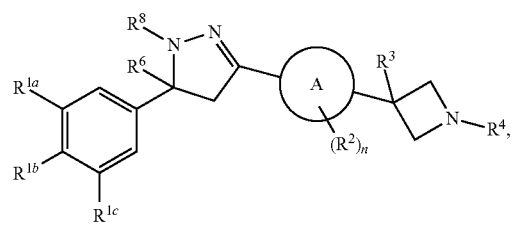

(6)

stereoisomers thereof, and pharmaceutically or veterinarily acceptable salts thereof.

9. The compound of claim 8 wherein A is phenyl, naphthyl, or pyridinyl;
$R^{1a}$, $R^{1b}$, and $R^{1c}$ are each independently selected from hydrogen, halo, hydroxyl, and $C_1$-$C_6$ haloalkyl;
$R^2$ is halo, cyano, hydroxyl, $C_1$-$C_6$alkyl, $C_1$-$C_6$haloalkyl, —C(O)NR$^a$R$^b$, or —OR; and wherein n is the integer 0, 1, or 2;
$R^3$ is hydrogen, halo, hydroxyl, $N_3$, or cyano;
$R^4$ is —C(O)R$^5$; and
$R^6$ is $C_1$-$C_6$haloalkyl,
stereoisomers thereof, and pharmaceutically or veterinarily acceptable salts thereof.

10. The compound of claim 9 wherein A is phenyl;
$R^{1a}$, $R^{1b}$, and $R^{1c}$ are each independently selected from hydrogen, halo, and $CF_3$;
$R^3$ is hydrogen, halo or hydroxyl;
$R^6$ is $CF_3$; and
n is the integer 0,
stereoisomers thereof, and pharmaceutically or veterinarily acceptable salts thereof.

11. The compound of claim 1 having Formula (3) or Formula (4)

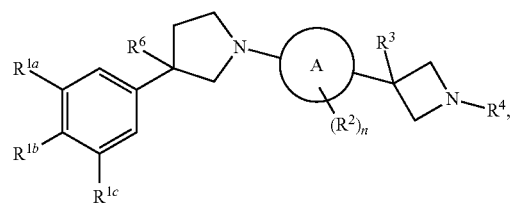

(3)

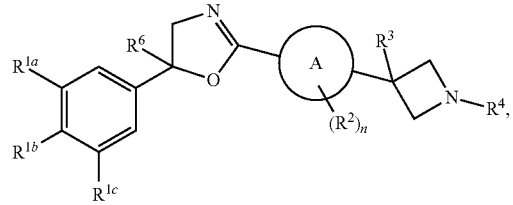

(4)

$R^{1a}$, $R^{1b}$, and $R^{1c}$ are each independently selected from hydrogen, halo, hydroxyl, and $C_1$-$C_6$ haloalkyl;
$R^2$ is halo, cyano, hydroxyl, $C_1$-$C_6$alkyl, $C_1$-$C_6$haloalkyl, —C(O)NR$^a$R$^b$, or —OR; and wherein n is the integer 0, 1, or 2;
$R^3$ is hydrogen, halo, hydroxyl, $N_3$, or cyano;
$R^4$ is —C(O)R$^5$; and
$R^6$ is $C_1$-$C_6$haloalkyl,
stereoisomers thereof, and pharmaceutically or veterinarily acceptable salts thereof.

12. A compound of claim 1 selected from the group consisting of:
1-(3-{4-[4-(3,5-dichloro-phenyl)-4-trifluoromethyl-4,5-dihydro-3H-pyrrol-2-yl]-phenyl}-3-fluoro-azetidin-1-yl)-2-methanesulfonyl-ethanone;
1-(3-{4-[4-(3,5-dichloro-phenyl)-4-trifluoromethyl-4,5-dihydro-3H-pyrrol-2-yl]-phenyl}-3-fluoro-azetidin-1-yl)-2-methyl-propan-1-one;
3-(3,5-dichloro-4-fluorophenyl)-5-(4-{3-fluoro-1-[(methylsulfonyl)-acetyl]azetidin-3-yl}phenyl)-3-(trifluoromethyl)-3,4-dihydro-2H-pyrrole;
3-(3,5-dichloro-4-fluorophenyl)-5-[4-(3-fluoro-1-isobutyrylazetidin-3-yl)phenyl]-3-(trifluoromethyl)-3,4-dihydro-2H-pyrrole;
1-(3-fluoro-3-{4-[4-(3,4,5-trichloro-phenyl)-4-trifluoromethyl-4,5-dihydro-3H-pyrrol-2-yl]-phenyl}-azetidin-1-yl)-2-methanesulfonyl-ethanone;
5-[4-(3-fluoro-1-isobutyrylazetidin-3-yl)phenyl]-3-(3,4,5-trichloro-phenyl)-3-(trifluoromethyl)-3,4-dihydro-2H-pyrrole;
1-(3-{4-[5-(3,5-dichloro-4-fluoro-phenyl)-5-trifluoromethyl-[1,4,2]dioxazol-3-yl]-phenyl}-3-fluoro-azetidin-1-yl)-2-methanesulfonyl-ethanone;
1-(3-{4-[5-(3,5-dichloro-4-fluoro-phenyl)-5-trifluoromethyl-[1,4,2]dioxazol-3-yl]-phenyl}-3-fluoro-azetidin-1-yl)-2-methyl-propan-1-one;
1-(3-{4-[5-(3,5-dichloro-phenyl)-5-trifluoromethyl-[1,4,2]dioxazol-3-yl]-phenyl}-3-fluoro-azetidin-1-yl)-2-methanesulfonyl-ethanone;
1-(3-{4-[5-(3,5-dichloro-phenyl)-5-trifluoromethyl-[1,4,2]dioxazol-3-yl]-phenyl}-3-fluoro-azetidin-1-yl)-2-methyl-propan-1-one;
1-(3-fluoro-3-{4-[5-(3,4,5-trichloro-phenyl)-5-trifluoromethyl-[1,4,2]dioxazol-3-yl]-phenyl}-azetidin-1-yl)-2-methanesulfonyl-ethanone;
1-(3-fluoro-3-{4-[5-(3,4,5-trichloro-phenyl)-5-trifluoromethyl-[1,4,2]dioxazol-3-yl]-phenyl}-azetidin-1-yl)-2-methyl-propan-1-one;
1-(3-fluoro-3-{4-[5-(3,4,5-trichloro-phenyl)-5-trifluoromethyl-4,5-dihydro-1H-pyrazol-3-yl]-phenyl}-azetidin-1-yl)-2-methyl-propan-1-one;
1-(3-{4-[5-(3,5-dichloro-4-fluoro-phenyl)-5-trifluoromethyl-4,5-dihydro-1H-pyrazol-3-yl]-phenyl}-3-fluoro-azetidin-1-yl)-2-methyl-propan-1-one;

1-(3-fluoro-3-(4-(5-(3,4,5-trichlorophenyl)-5-(trifluoromethyl)-4,5-dihydro-1H-pyrazol-3-yl)phenyl)azetidin-1-yl)-2-(methylsulfonyl)ethanone;

1-(3-(4-(5-(3,5-dichlorophenyl)-5-(trifluoromethyl)-4,5-dihydro-1H-pyrazol-3-yl)phenyl)-3-fluoroazetidin-1-yl)-2-(methylsulfonyl)ethanone;

1-(3-(4-(5-(3,5-dichlorophenyl)-5-(trifluoromethyl)-4,5-dihydro-1H-pyrazol-3-yl)phenyl)-3-fluoroazetidin-1-yl)-2-methylpropan-1-one; and 1-(3-(4-(5-(3,5-dichloro-4-fluorophenyl)-5-(trifluoromethyl)-4,5-dihydro-1H-pyrazol-3-yl)phenyl)-3-fluoroazetidin-1-yl)-2-(methylsulfonyl)ethanone, stereoisomers thereof, and pharmaceutically or veterinarily acceptable salts thereof.

13. A pharmaceutical or veterinary composition comprising a therapeutic amount of a compound of Formula (1)

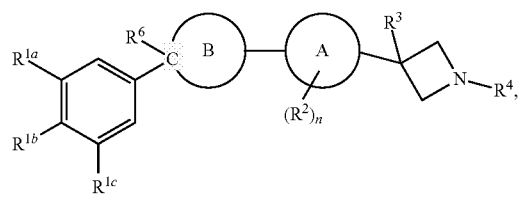

(1)

wherein

A is phenyl, naphthyl, or heteroaryl where said heteroaryl contains 1 to 4 heteroatoms each independently selected from N, O and S;

B is

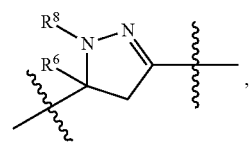 B1

,

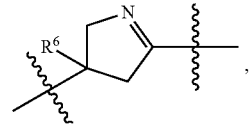 B2

,

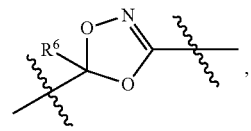 B3

,

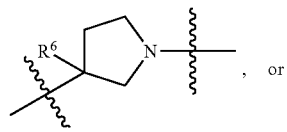 B4

, or

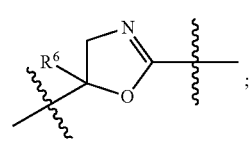 B5

;

where in " ~~~ " represents the point of attachment;

$R^{1a}$, $R^{1b}$, and $R^{1c}$ are each independently hydrogen, halo, hydroxyl, cyano, nitro, $C_1$-$C_6$alkyl, $C_1$-$C_6$haloalkyl, $C_1$-$C_6$alkoxy, $C_0$-$C_3$alkyl$C_3$-$C_6$cycloalkyl, $C_1$-$C_6$haloalkoxy, —C(O)NH$_2$, —SF$_5$, or —S(O)$_p$R;

$R^2$ is halo, cyano, $C_1$-$C_6$alkyl, $C_1$-$C_6$haloalkyl, nitro, hydroxyl, —C(O)NR$^a$R$^b$, $C_2$-$C_6$alkenyl, $C_2$-$C_6$alkynyl, —S(O)$_p$R, or —OR;

$R^3$ is hydrogen, halo, hydroxyl, cyano, $C_1$-$C_6$alkyl, $C_1$-$C_6$haloalkyl, $C_0$-$C_3$alkyl$C_3$-$C_6$cycloalkyl, —C(O)NH$_2$, nitro, —SC(O)R, —C(O)NR$^a$R$^b$, $C_0$-$C_3$alkylNR$^a$R$^4$, —NR$^a$NR$^b$R$^4$, —NR$^a$OR$^b$, —ONR$^a$R$^b$, N$_3$, —NHR$^4$, —OR, or —S(O)$_p$R;

$R^4$ is hydrogen, $C_1$-$C_6$alkyl, $C_0$-$C_6$alkyl$C_3$-$C_6$cycloalkyl, —C(O)R$^5$, —C(S)R$^5$, —C(O)NR$^a$R$^5$, —C(O)C(O)NR$^a$R$^5$, —S(O)$_p$R$^c$, —S(O)$_2$NR$^a$R$^5$, —C(NR$^7$)R$^5$, —C(NR$^7$)NR$^a$R$^5$, $C_0$-$C_6$alkylphenyl, $C_0$-$C_6$alkylheteroaryl, or $C_0$-$C_6$alkylheterocycle;

$R^5$ is hydrogen, $C_1$-$C_6$alkyl, $C_2$-$C_6$alkenyl, $C_0$-$C_6$alkyl$C_3$-$C_6$cycloalkyl, $C_0$-$C_6$alkylphenyl, $C_0$-$C_6$alkylheteroaryl, or $C_0$-$C_6$alkylheterocycle;

$R^6$ is cyano, $C_1$-$C_6$alkyl, $C_1$-$C_6$haloalkyl, —C(O)NR$^a$R$^b$, $C_2$-$C_6$alkenyl, $C_2$-$C_6$alkynyl, $C_2$-$C_6$haloalkenyl, or $C_2$-$C_6$haloalkynyl;

$R^7$ is hydrogen, $C_1$-$C_6$alkyl, hydroxyl, cyano, nitro, —S(O)$_p$R$^c$, or $C_1$-$C_6$alkoxy;

$R^8$ is hydrogen, $C_1$-$C_6$alkyl, hydroxyl, cyano, —S(O)$_p$R$^c$, or $C_1$-$C_6$alkoxy;

R is $C_1$-$C_6$alkyl or $C_3$-$C_6$cycloalkyl each optionally substituted by at least one halo;

$R^a$ is hydrogen, $C_1$-$C_6$alkyl, or $C_0$-$C_3$alkyl$C_3$-$C_6$cycloalkyl; wherein the alkyl and alkylcycloalkyl is optionally substituted by cyano or at least one halo substituent;

$R^b$ is hydrogen, $C_1$-$C_6$alkyl, $C_3$-$C_6$cycloalkyl, $C_0$-$C_3$alkylphenyl, $C_0$-$C_3$alkylheteroaryl, or $C_0$-$C_3$alkylheterocycle, each optionally substituted, where chemically possible, with at least one substituent selected from hydroxyl, cyano, halo, or —S(O)$_p$R;

$R^c$ is $C_1$-$C_6$alkyl, $C_1$-$C_6$haloalkyl, $C_1$-$C_6$haloalkyl$C_3$-$C_6$cycloalkyl, $C_0$-$C_3$alkyl$C_3$-$C_6$cycloalkyl, $C_0$-$C_3$alkylphenyl, $C_0$-$C_3$alkylheteroaryl, or $C_0$-$C_3$alkylheterocycle each optionally substituted with at least one substituent selected from cyano, halo, hydroxyl, oxo, $C_1$-$C_6$alkyl, $C_1$-$C_6$alkoxy, $C_1$-$C_6$haloalkoxy, $C_1$-$C_6$haloalkyl, —S(O)$_p$R, —SH, —S(O)$_p$NR$^a$R$^b$, —NR$^a$R$^b$, —NR$^a$C(O)R$^b$, —SC(O)R$^b$, —SCN, or —C(O)NR$^a$R$^b$;

each of $R^4$ and $R^5$ $C_1$-$C_6$alkyl or $C_0$-$C_6$alkyl$C_3$-$C_6$cycloalkyl can be optionally and independently substituted by at least one substituent selected from $C_1$-$C_6$alkyl, cyano, halo, hydroxyl, $C_1$-$C_6$hydroxyalkyl, oxo, $C_1$-$C_6$alkoxy, $C_1$-$C_6$haloalkoxy, $C_1$-$C_6$alkyl, $C_1$-$C_6$haloalkyl, —S(O)$_p$R$^c$, —SH, —S(O)$_p$NR$^a$R$^b$, —NR$^a$R$^b$, —NR$^a$C(O)R$^b$, —SC(O)R$^b$, —SCN, or —C(O)NR$^a$R$^b$; and wherein $R^4$ and $R^5$ $C_0$-$C_6$alkylphenyl, $C_0$-$C_6$alkylheteroaryl, or $C_0$-$C_6$alkylheterocycle moiety can be further optionally substituted with at least one substituent selected from $C_1$-$C_6$alkyl, cyano, halo, oxo, =S, =NR$^7$, hydroxyl, $C_1$-$C_6$hydroxyalkyl, $C_1$-$C_6$alkoxy, $C_1$-$C_6$alkyl, $C_1$-$C_6$haloalkyl, —SH, —S(O)$_p$R, and $C_1$-$C_6$haloalkoxy;

n is the integer 0, 1, or 2, and when n is 2, each $R^2$ may be identical or different from each other; and p is the integer 0, 1, or 2;

stereoisomers thereof, and pharmaceutically or veterinarily acceptable salts thereof.

14. The pharmaceutical or veterinary composition of claim 13 further comprising a pharmaceutically or veterinarily acceptable excipient, diluent, or carrier, and optionally comprising at least one additional veterinary agent selected from the group consisting of abamectin, ivermectin, avermectin, moxidectin, emamectin, eprinomectin, selamectin, doramectin, nemadectin, albendazole, cambendazole, fenbendazole, flubendazole, mebendazole, oxfenbendazole, oxibendazole, parbendazole, tetramisole, levamisole, pyrantel pamoate, oxantel, morantel, indoxacarb, closantel, triclabendazole, clorsulon, refoxanide, niclosamide, praziquantel, epsiprantel, 2-desoxoparaherquamide, pyripole, pyrafluprole, lufenuron, spiromesifen, tebufenozide, spinosad, spinetoram, imidacloprid, dinotefuran, metaflumizone, thibendiamide, chlorantraniliprole, indoxacarb, pyridalyl, deltamethrin, pyrimidifen, pyrifluquinazon, milbemycin oxime, milbemycin, demiditraz, amitraz, fipronil, S-methoprene, hydroprene, pyriproxyfen, permethrin, and pyrethrin, or mixtures thereof.

15. A method for the treatment of an animal with a parasitic infection or infestation comprising administering to said animal in need thereof an effective amount of a compound of Formula (1)

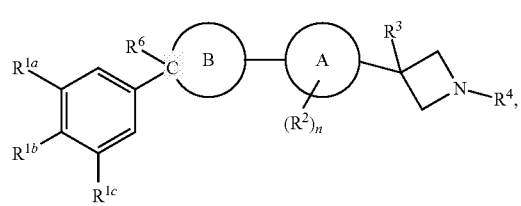

(1)

wherein

A is phenyl, naphthyl, or heteroaryl where said heteroaryl contains 1 to 4 heteroatoms each independently selected from N, O and S;

B is

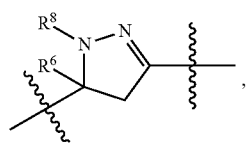

B1

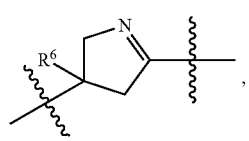

B2

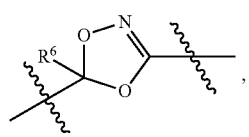

B3

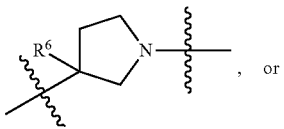

B4

, or

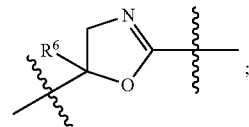

B5

;

where in "∼∼∼" represents the point of attachment, and "*" represents a chiral carbon;

$R^{1a}$, $R^{1b}$, and $R^{1c}$ are each independently hydrogen, halo, hydroxyl, cyano, nitro, $C_1$-$C_6$alkyl, $C_1$-$C_6$haloalkyl, $C_1$-$C_6$alkoxy, $C_0$-$C_3$alkylC$_3$-$C_6$cycloalkyl, $C_1$-$C_6$haloalkoxy, —C(O)NH$_2$, —SF$_5$, or —S(O)$_p$R;

$R^2$ is halo, cyano, $C_1$-$C_6$alkyl, $C_1$-$C_6$haloalkyl, nitro, hydroxyl, —C(O)NR$^a$R$^b$, $C_2$-$C_6$alkenyl, $C_2$-$C_6$alkynyl, —S(O)$_p$R, or —OR;

$R^3$ is hydrogen, halo, hydroxyl, cyano, $C_1$-$C_6$alkyl, $C_1$-$C_6$haloalkyl, $C_0$-$C_3$alkylC$_3$-$C_6$cycloalkyl, —C(O)NH$_2$, nitro, —SC(O)R, —C(O)NR$^a$R$^b$, $C_0$-$C_3$alkylNR$^a$R$^4$, —NR$^a$NR$^b$R$^4$, —NR$^a$OR$^b$, —ONR$^a$R$^b$, N$_3$, —NHR$^4$, —OR, or —S(O)$_p$R;

$R^4$ is hydrogen, $C_1$-$C_6$alkyl, $C_0$-$C_6$alkylC$_3$-$C_6$cycloalkyl, —C(O)R$^5$, —C(S)R$^5$, —C(O)NR$^a$R$^5$, —C(O)C(O)NR$^a$R$^5$, —S(O)$_p$R$^c$, —S(O)$_2$NR$^a$R$^5$, —C(NR$^7$)R$^5$, —C(NR$^7$)NR$^a$R$^5$, $C_0$-$C_6$alkylphenyl, $C_0$-$C_6$alkylheteroaryl, or $C_0$-$C_6$alkylheterocycle;

$R^5$ is hydrogen, $C_1$-$C_6$alkyl, $C_2$-$C_6$alkenyl, $C_0$-$C_6$alkylC$_3$-$C_6$cycloalkyl, $C_0$-$C_6$alkylphenyl, $C_0$-$C_6$alkylheteroaryl, or $C_0$-$C_6$alkylheterocycle;

$R^6$ is cyano, $C_1$-$C_6$alkyl, $C_1$-$C_6$haloalkyl, —C(O)NR$^a$R$^b$, $C_2$-$C_6$alkenyl, $C_2$-$C_6$alkynyl, $C_2$-$C_6$haloalkenyl, or $C_2$-$C_6$haloalkynyl;

$R^7$ is hydrogen, $C_1$-$C_6$alkyl, hydroxyl, cyano, nitro, —S(O)$_p$R$^c$, or $C_1$-$C_6$alkoxy;

$R^8$ is hydrogen, $C_1$-$C_6$alkyl, hydroxyl, cyano, —S(O)$_p$R$^c$, or $C_1$-$C_6$alkoxy;

R is $C_1$-$C_6$alkyl or $C_3$-$C_6$cycloalkyl each optionally substituted by at least one halo;

$R^a$ is hydrogen, $C_1$-$C_6$alkyl, or $C_0$-$C_3$alkylC$_3$-$C_6$cycloalkyl; wherein the alkyl and alkylcycloalkyl is optionally substituted by cyano or at least one halo substituent;

$R^b$ is hydrogen, $C_1$-$C_6$alkyl, $C_3$-$C_6$cycloalkyl, $C_0$-$C_3$alkylphenyl, $C_0$-$C_3$alkylheteroaryl, or $C_0$-$C_3$alkylheterocycle, each optionally substituted, where chemically possible, with at least one substituent selected from hydroxyl, cyano, halo, or —S(O)$_p$R;

$R^c$ is $C_1$-$C_6$alkyl, $C_1$-$C_6$haloalkyl, $C_1$-$C_6$haloalkylC$_3$-$C_6$cycloalkyl, $C_0$-$C_3$alkylC$_3$-$C_6$cycloalkyl, $C_0$-$C_3$alkylphenyl, $C_0$-$C_3$alkylheteroaryl, or $C_0$-$C_3$alkylheterocycle each optionally substituted with at least one substituent selected from cyano, halo, hydroxyl, oxo, $C_1$-$C_6$alkyl, $C_1$-$C_6$alkoxy, $C_1$-$C_6$haloalkoxy, $C_1$-$C_6$haloalkyl, —S(O)$_p$R, —SH, —S(O)$_p$NR$^a$R$^b$, —NR$^a$R$^b$, —NR$^a$C(O)R$^b$, —SC(O)R$^b$, —SCN, or —C(O)NR$^a$R$^b$;

each of $R^4$ and $R^5$ $C_1$-$C_6$alkyl or $C_0$-$C_6$alkylC$_3$-$C_6$cycloalkyl can be optionally and independently substituted by at least one substituent selected from $C_1$-$C_6$alkyl, cyano, halo, hydroxyl, $C_1$-$C_6$hydroxyalkyl, oxo, $C_1$-$C_6$alkoxy, $C_1$-$C_6$haloalkoxy, $C_1$-$C_6$alkyl, $C_1$-$C_6$haloalkyl, —S(O)$_p$R$^c$, —SH, —S(O)$_p$NR$^a$R$^b$, —NR$^a$R$^b$, —NR$^a$C(O)R$^b$, —SC(O)R$^c$, —SCN, or —C(O)NR$^a$R$^b$; and wherein R$^4$ and R$^5$ $C_0$-$C_6$alkylphenyl, $C_0$-$C_6$alkylheteroaryl, or $C_0$-$C_6$alkylheterocycle moiety can be further optionally substituted with at least one substituent selected from $C_1$-$C_6$alkyl, cyano, halo, oxo, =S, =NR$^7$, hydroxyl, $C_1$-$C_6$hydroxyalkyl, $C_1$-$C_6$alkoxy, $C_1$-$C_6$alkyl, $C_1$-$C_6$haloalkyl, —SH, —S(O)$_p$R, and $C_1$-$C_6$haloalkoxy;

n is the integer 0, 1, or 2, and when n is 2, each R$^2$ may be identical or different from each other; and p is the integer 0, 1, or 2;

stereoisomers thereof, and pharmaceutically or veterinarily acceptable salts thereof, and optionally, at least one additional veterinary agent.

* * * * *